US009725402B2

(12) United States Patent
Frost et al.

(10) Patent No.: US 9,725,402 B2
(45) Date of Patent: Aug. 8, 2017

(54) NITROSO COMPOUNDS AS NITROXYL DONORS AND METHODS OF USE THEREOF

(71) Applicant: Cardioxyl Pharmaceuticals, Inc., Chapel Hill, NC (US)

(72) Inventors: Lisa Marie Frost, Abingdon (GB); Stephen Martin Courtney, Abingdon (GB); Frederick Arthur Brookfield, Abingdon (GB); Vincent Jacob Kalish, Annapolis, MD (US)

(73) Assignee: Cardioxyl Pharmaceuticals, Inc., Chapel Hill, NC (US)

( * ) Notice: Subject to any disclaimer, the term of this patent is extended or adjusted under 35 U.S.C. 154(b) by 0 days.

(21) Appl. No.: 14/927,994

(22) Filed: Oct. 30, 2015

(65) Prior Publication Data
US 2016/0052862 A1 Feb. 25, 2016

Related U.S. Application Data

(63) Continuation of application No. 14/444,750, filed on Jul. 28, 2014, which is a continuation of application No. 13/654,937, filed on Oct. 18, 2012, now Pat. No. 8,791,134, which is a continuation of application No. 12/437,512, filed on May 7, 2009, now Pat. No. 8,318,705.

(60) Provisional application No. 61/051,287, filed on May 7, 2008.

(51) Int. Cl.
| | |
|---|---|
| *C07C 207/04* | (2006.01) |
| *C07C 207/00* | (2006.01) |
| *C07D 309/14* | (2006.01) |
| *C07D 407/12* | (2006.01) |
| *C07D 211/44* | (2006.01) |
| *C07D 211/58* | (2006.01) |
| *C07D 333/42* | (2006.01) |
| *C07D 405/12* | (2006.01) |
| *C07D 405/14* | (2006.01) |
| *C07D 451/10* | (2006.01) |
| *C07F 9/117* | (2006.01) |
| *C07F 9/58* | (2006.01) |
| *C07C 255/19* | (2006.01) |
| *C07D 309/10* | (2006.01) |
| *C07F 9/59* | (2006.01) |

(52) U.S. Cl.
CPC .......... *C07C 207/00* (2013.01); *C07C 207/04* (2013.01); *C07C 255/19* (2013.01); *C07D 211/44* (2013.01); *C07D 211/58* (2013.01); *C07D 309/10* (2013.01); *C07D 309/14* (2013.01); *C07D 333/42* (2013.01); *C07D 405/12* (2013.01); *C07D 405/14* (2013.01); *C07D 407/12* (2013.01); *C07D 451/10* (2013.01); *C07F 9/117* (2013.01); *C07F 9/585* (2013.01); *C07F 9/595* (2013.01)

(58) Field of Classification Search
None
See application file for complete search history.

(56) References Cited

U.S. PATENT DOCUMENTS

| | | | |
|---|---|---|---|
| 5,578,610 A | 11/1996 | D'ambra | |
| 5,670,662 A | 9/1997 | Crosby et al. | |
| 6,355,666 B1 | 3/2002 | Lai et al. | |
| 6,787,365 B2 | 9/2004 | Varki et al. | |
| 7,696,373 B2 | 4/2010 | King | |
| 7,989,652 B2 | 8/2011 | King | |
| 8,269,034 B2 | 9/2012 | King | |
| 8,569,536 B2 | 10/2013 | King | |
| 2013/0040919 A1 | 2/2013 | King | |

FOREIGN PATENT DOCUMENTS

WO 2007120839 10/2007

OTHER PUBLICATIONS

Moriarty et al., "Oxidative Cleavage of Ketoximes with Lobodosobenzene Diacetate", Synthetic Communications, 1986, pp. 1247-1254.
Ito et al., "A Medium-Term Rat Liver Bioassy for Rapid In-Vivo Detection of Carcinogenic Potential of Chemicals", Cancer Sci, Jan. 2003, pp. 3-8.
Search Report dated Feb. 7, 2012 in European Application No. 09743703.2.
Search Report dated Jun. 22, 2009 in International Patent Application No. PCT/US09/43203.
King, Bruce S., "Bioisosteres, Conformational Restriction, and Pro-drugs—Case History: An Example of a Conformational Restriction Approach", Medical Chemistry: Principles and Practice, 1994 (month unknown), pp. 206-225.
Kryukov et al., "Phosphoryl Derivatives of Geminal Nitrosohexaflouropropan-2-ol," Doklady Chemistry—Proceedings of the Academy of Sciences of the USSR, Chemistry Section, Jan. 1980, pp. 333-335.
Rehse et al., "New NO-Donors with Antithrombotic and Vasodilating Activities, Part 20: Azodioxides Activated by Electron Acceptors in Geminal or Vicinal Position", Arch. Pharm. Pharm. Med. Chem., Mar. 1998, pp. 104-110.
Sha et al., "Hydrolysis of Acyloxy Nitroso Compounds Yields Nitroxyl (HNO)" J. Am. Chem. Soc., Jan. 2006, pp. 9687-9692.
Nermuth,C.G., "Molecular Variations Based on Isosteric Replacements", The Practice of Medicinal Chemistry, Jan. 1996, pp. 203-237.
Office Action dated Oct. 30, 2015 in Indian Patent Application No. 7557/DELNP/2010.

(Continued)

*Primary Examiner* — Theodore R West
(74) *Attorney, Agent, or Firm* — Byrne Poh LLP; Nina R. Horan

(57) ABSTRACT

The invention relates to nitroso derivatives including carboxylic acid and phosphoric acid esters of hydroxy nitroso compounds that donate nitroxyl (HNO) under physiological conditions. The compounds and compositions of the invention are useful in treating and/or preventing the onset and/or development of diseases or conditions that are responsive to nitroxyl therapy, including heart failure, ischemia/reperfusion injury and cancer.

11 Claims, No Drawings

(56) References Cited

OTHER PUBLICATIONS

Office Action dated Dec. 28, 2015 in Japanese Patent Application No. 2014-235732.
Office Action dated Feb. 8, 2016 in Canadian Patent Application No. 2,723,590.
U.S. Appl. No. 14/043,345, filed Oct. 1, 2013.
Lown, J.W., "The Reaction of Lead Tetra-Acetate with Oximes: Part 1—Alicyclic and Aliphatic Oximes", J. Chem. Soc. B., 1996 (month unknown), pp. 441-446.
Notice of Reasons Rejected dated Nov. 5, 2013 in Japanese Patent Application No. 2011-508684.
Krzhizhevskii et al., "Reactions of Polyfluoronitroalkanes Containing an Active Hydrogen Atom", Izvestiya Akademii Nauk SSSR, Seriya Khimicheskaya, RU, 1974 (month unknown), pp. 2513-2517.
Calvet, G. et al., "2,2-Dimethyl-5-nitroso-1,3-dioxan-5-yl benzoate, 2,2-dimethyl-5-nitroso-1,3-dioxan-5-yl 4-chlorobenzoate and 5-nitroso-1,3-dioxan-5-yl chlorobenzoate", In Acta Crystallographica, Section C: Crystal Structure Communications, vol. C63, May 31, 2007, pp. 365-368.
Calvet, G. et al., "Lewis Acid-Promoted Hetero Diels-Alder Cycloaddition of alpha-Acetoxynitroso Dienophiles", In Organic Letters, vol. 6, No. 14, Jul. 1, 2004, pp. 2449-2451.
Extended European Search Report dated Sep. 21, 2016 in European Patent Application No. 16163363.1.
Kropf, H. and Lambeck, R., "Reactions with Lead Tetracetate, I. About gem. -Nitroso-Acyloxy-alkane and Their Dimers", In European Journal of Organic Chemistry, vol. 700, No. 1, Jan. 23, 1966, pp. 1-17.
Kryukov, L. N. et al., "Phosphoryl Derivatives of Germinal Nitrosohexafluro-2-propanol", In Doklady Akademii Nauk SSSR, Russia, Jul. 1979, vol. 247, No. 1, pp. 115-117.
Kugelman, M. et al., "Semisynthetic Aminoglycoside Antibacterials. Part II. Synthesis of Gentamicin X2 and Related Compounds", In Journal of the American Chemical Society, Perkin Transactions, vol. 1, No. 10, Jan. 1, 1976, pp. 1097-1113.
Office Action dated Jan. 29, 2016 in U.S. Appl. No. 14/444,750.
Office Action dated Jun. 9, 2016 in U.S. Appl. No. 14/444,750.
Office Action dated Jun. 24, 2014 in Chinese Patent Application No. 200980124860.3.
Partial European Search Report dated Jun. 14, 2016 in European Patent Application No. 16163363.1.
Rehse, K. and Herpel, M., "Azodioxides Activated by Electron Acceptors in Geminal or Vicinal Position", In Archiv der Pharmazie, vol. 331, No. 3, Mar. 1998, pp. 104-110.
Office Action dated Nov. 30, 2016 in Chinese Patent Application No. 201510245919.1.
Office Action dated Nov. 28, 2016 in U.S. Appl. No. 14/444,750.

NITROSO COMPOUNDS AS NITROXYL DONORS AND METHODS OF USE THEREOF

CROSS-REFERENCE TO RELATED APPLICATIONS

This application is a continuation of application Ser. No. 14/444,750, filed Jul. 28, 2014, which is a continuation of application Ser. No. of 13/654,937, filed Oct. 18, 2012, now U.S. Pat. No. 8,791,134, which is a continuation of application Ser. No. of 12/437,512, filed May 7, 2009, now U.S. Pat. No. 8,318,705, which claims the benefit under 35 U.S.C. §119(e) of provisional application Ser. No. 61/051,287, filed May 7, 2008, the contents of all of which applications are incorporated by reference.

STATEMENT REGARDING FEDERALLY SPONSORED RESEARCH OR DEVELOPMENT

Not applicable.

BACKGROUND OF THE INVENTION

Heart Failure

Congestive heart failure (CHF) is a generally progressive, life threatening condition in which myocardial contractility is depressed such that the heart is unable to adequately pump the blood returning to it, also referred to as decompensation. Symptoms include breathlessness, fatigue, weakness, leg swelling, and exercise intolerance. On physical examination, patients with heart failure often have elevated heart and respiratory rates (an indication of fluid in the lungs), edema, jugular venous distension, and/or enlarged hearts. The most common cause of CHF is atherosclerosis, which causes blockages in the coronary arteries that provide blood flow to the heart muscle. Ultimately, such blockages may cause myocardial infarction with subsequent decline in heart function and resultant heart failure. Other causes of CHF include valvular heart disease, hypertension, viral infections of the heart, alcohol consumption, and diabetes. Some cases of CHF occur without clear etiology and are called idiopathic. The effects of CHF on a subject experiencing the condition can be fatal.

There are several types of CHF. Two types of CHF are identified according to which phase of the cardiac pumping cycle is more affected. Systolic heart failure occurs when the heart's ability to contract decreases. The heart cannot pump with enough force to push a sufficient amount of blood into the circulation leading to a reduced left ventricular ejection fraction. Lung congestion is a typical symptom of systolic heart failure. Diastolic heart failure refers to the heart's inability to relax between contractions and allow enough blood to enter the ventricles. Higher filling pressures are required to maintain cardiac output, but contractility as measured by left ventricular ejection fraction is typically normal. Swelling (edema) in the abdomen and legs is a typical symptom of diastolic heart failure. Often, an individual experiencing heart failure will have some degree of both systolic heart failure and diastolic heart failure.

CHF is also classified according to its severity. The New York Heart Association classifies CHF into four classes: Class I involves no obvious symptoms, with no limitations on physical activity; Class II involves some symptoms during or after normal activity, with mild physical activity limitations; Class III involves symptoms with less than ordinary activity, with moderate to significant physical activity limitations; and Class IV involves significant symptoms at rest, with severe to total physical activity limitations. Typically, an individual progresses through the classes as they live with the condition.

Although CHF is generally thought of as a chronic, progressive condition, it can also develop suddenly. This type of CHF is called acute CHF, and it is a medical emergency. Acute CHF can be caused by acute myocardial injury that affects either myocardial performance, such as myocardial infarction, or valvular/chamber integrity, such as mitral regurgitation or ventricular septal rupture, which leads to an acute rise in left ventricular and diastolic pressure resulting in pulmonary edema and dyspnea.

Common treatment agents for CHF include vasodilators (drugs that dilate blood vessels), positive inotropes (drugs that increase the heart's ability to contract), and diuretics (drugs to reduce fluid). Additionally, beta-antagonists (drugs that antagonize beta-adrenergic receptors) have become standard agents for treating mild to moderate heart failure. Lowes et al. *Clin. Cardiol.*, 23:III1 1-6 (2000).

Positive inotropic agents include beta-adrenergic agonists, such as dopamine, dobutamine, dopexamine, and isoproterenol. However, use of a beta-agonist has potential complications, such as arrhythmogenesis and increased oxygen demand by the heart. Additionally, the initial short-lived improvement of myocardial contractility afforded by these drugs is followed by an accelerated mortality rate resulting largely from a greater frequency of sudden death. Katz, HEART FAILURE: PATHOPHYSIOLOGY, MOLECULAR BIOLOGY AND CLINICAL MANAGEMENT, Lippincott, Williams & Wilkins (1999).

Beta-antagonists antagonize beta-adrenergic receptor function. While initially contra-indicated in heart failure, they have been found to provide a marked reduction in mortality and morbidity in clinical trials. Bouzamondo et al., *Fundam. Clin. Pharmacol.*, 15: 95-109 (2001). Accordingly, they have become an established therapy for heart failure. However, even subjects that improve under beta-antagonist therapy may subsequently decompensate and require acute treatment with a positive inotropic agent. Unfortunately, as their name suggests, beta-antagonists block the mechanism of action of the positive inotropic beta-agonists that are used in emergency care centers. Bristow et al., *J. Card. Fail.*, 7: 8-12 (2001).

Vasodilators, such as nitroglycerin, have been used for a long period of time to treat heart failure. However, the cause of nitroglycerin's therapeutic effect was not known until late in the last century when it was discovered that the nitric oxide molecule (NO) was responsible for nitroglycerin's beneficial effects. In some subjects experiencing heart failure, a nitric oxide donor is administered in combination with a positive inotropic agent to both cause vasodilation and to increase myocardial contractility. However, this combined administration can impair the effectiveness of positive inotropic treatment agents. For example, Hart et al, *Am. J. Physiol. Heart Circ. Physiol.*, 281:146-54 (2001) reported that administration of the nitric oxide donor sodium nitroprusside, in combination with the positive inotropic, beta-adrenergic agonist dobutamine, impaired the positive inotropic effect of dobutamine. Hare et al., *Circulation*, 92:2198-203 (1995) also disclosed the inhibitory effect of nitric oxide on the effectiveness of dobutamine.

As described in U.S. Pat. No. 6,936,639, compounds that donate nitroxyl (HNO) under physiological conditions have both positive inotropic and lusotropic effects and offer significant advantages over existing treatments for failing hearts. Due to their concomitant positive inotropic/lusotropic action and unloading effects, nitroxyl donors were reported as helpful in treating cardiovascular diseases characterized by high resistive load and poor contractile performance. In particular, nitroxyl-donating compounds were reported as useful in the treatment of heart failure, including heart failure in individuals receiving beta-antagonist therapy.

Ischemia

Ischemia is a condition characterized by an interruption or inadequate supply of blood to tissue, which causes oxygen deprivation in the affected tissue. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. Further, upon reperfusion with subsequent reoxygenation of the tissue, when the blood is able to flow again or the oxygen demand of the tissue subsides, additional injury can be caused by oxidative stress.

Ischemia/reperfusion injury refers to tissue damage caused by oxygen deprivation followed by reoxygenation. The effects of ischemia/reperfusion injury in a subject experiencing the condition can be fatal, particularly when the injury occurs in a critical organ such as the heart or brain.

Accordingly, compounds and compositions effective in preventing or protecting against ischemia/reperfusion injury would be useful pharmaceuticals. Compounds such as nitroglycerin have been used for a long period of time to help control vascular tone and protect against myocardial ischemia/reperfusion injury. It was discovered that the nitric oxide molecule was responsible for nitroglycerin's beneficial effects. This discovery prompted interest in medical uses for nitric oxide and investigations into related species such as nitroxyl. As reported in U.S. patent application Ser. No. 10/463,084 (U.S. Publication No. 2004/0038947) administration of a compound that donates nitroxyl under physiological conditions, prior to ischemia, can attenuate ischemia/reperfusion injury to tissues, for example, myocardial tissues. This beneficial effect was reported as a surprising result given that nitroxyl was previously reported to increase ischemia/reperfusion injury (See, Ma et al., "Opposite Effects of Nitric Oxide and Nitroxyl on Postischemic Myocardial Injury," *Proc. Nat'l Acad. Sci.,* 96(25): 14617-14622 (1999), reporting that administration of Angeli's salt (a nitroxyl donor under physiological conditions) to anesthetized rabbits during ischemia and 5 minutes prior to reperfusion increased myocardial ischemia/reperfusion injury and Takahira et al., "Dexamethasone Attenuates Neutrophil Infiltration in the Rat Kidney in Ischemia/Reperfusion Injury: The Possible Role of Nitroxyl," *Free Radical Biology & Medicine,* 31(6):809-815 (2001) reporting that administration of Angeli's salt during ischemia and 5 minutes before reperfusion of rat renal tissue contributed to neutrophil infiltration into the tissue, which is believed to mediate ischemia/reperfusion injury). In particular, pre-ischemic administration of Angeli's salt and isopropylamine/NO has been reported to prevent or reduce ischemia/reperfusion injury.

Cancer

One of the challenges in developing anti-cancer drugs is to discover compounds that are selectively toxic to tumor cells over normal cells. It has been found that tumor tissues have an acidic microenvironment with a pH from 6.0 to 7.0, while the extra- and intracellular milieu of normal cells has a pH of 7.4. Angeli's salt has been reported to exhibit strong cytotoxicity to cancer cells in weakly acidic solutions, whereas no toxicity was observed at pH 7.4 (Stoyanovsky, D. A. et al. *J. Med. Chem.* 2004, 47, 210-217; and WO 03/020221). In a subcutaneous xenograft model of pheochromocytoma, Angeli's salt was found to inhibit tumor growth at a dose that was nontoxic to nude mice. Nitroxyl derivatives that are not known to release HNO, such as ruboxyl, a nitroxyl analogue of daunorubicin, have been shown to be active against hepatic metastases from colorectal carcinoma (Sirovich, I. et al *Tumor Biol.* 1999; 20:270-276).

Norris A. J. et al (*Intl. J. Cancer* 2008, 122, 1905-1910) reported that Angeli's salt inhibits the proliferation of cultured breast cancer cells and decreases tumor mass in a mouse xenograft model. Norris A. J. et al proposed that HNO released from Angeli's salt blocks glycolysis in cancer cells by inhibiting the enzyme glyceraldehyde 3-phosphate dehydrogenase (GAPDH), resulting in decreased levels of HIF-1α (hypoxia-inducible factor) protein and activity, lower VEGF (vascular endothelial growth factor) production, decreased tumor angiogenesis and an increase in apoptotic cells.

Nitroxyl Donors

Due to its inherent reactivity, HNO must be generated in situ from donor compounds. To date, the vast majority of studies of the biological effect of HNO have used the donor sodium α-oxyhyponitrite ("Angeli's salt" or "AS"). However, the chemical stability of AS has made it unsuitable to develop as a therapeutic agent. Angeli's salt also releases nitrite, which possesses its own biological profile. N-hydroxybenzenesulfonamide ("Piloty's acid" or "PA") has previously been shown to be a nitroxyl donor only at high pH (>9) (Bonner, F. T.; Ko, Y. *Inorg. Chem.* 1992, 31, 2514-2519). Under physiological conditions, PA has been shown to be a nitric oxide donor via an oxidative pathway (Zamora, R.; Grzesiok, A.; Weber, H.; Feelisch, M. *Biochem. J.* 1995, 312, 333-339). International Patent Application Publication WO 2007/109175 describes N-hydroxylsulfonamide derivatives that donate nitroxyl under physiological conditions.

Acyloxy nitroso compounds have been reported to yield nitroxyl in situ when reacted with nucleophiles (Sha, X. et al *J. Am. Chem. Soc.* 2006, 128, 9687-9692). Although Rehse and Herpel (*Arch. Pharm. Med. Chem.* 1998, 331, 104-110) showed acyloxy nitroso compounds inhibit platelet aggregation and thrombus formation (indicative of NO release), they generate only small amounts (<1%) of NO and HNO under neutral conditions. International Patent Application Publication WO 2007/120839 describes conjugates of acyloxy nitroso compounds with non-steroidal anti-inflammatory drugs (NSAID) as nitroxyl donors for treating congestive heart failure.

Significant Medical Need

Despite efforts towards the development of new therapies for the treatment of diseases and conditions such as heart failure, ischemia/reperfusion injury and cancer, there remains a significant interest in and need for additional or alternative compounds that treat or prevent the onset or severity of these and related diseases or conditions. In particular, there remains a significant medical need for alternative or additional therapies for the treatment of diseases or conditions that are responsive to nitroxyl therapy. New compounds that donate nitroxyl under physiological conditions and methods of using compounds that donate nitroxyl under physiological conditions may thus find use as therapies for treating, preventing and/or delaying the onset and/or development of diseases or conditions responsive to nitroxyl therapy, including heart disease, ischemia/reperfusion injury and cancer. Preferably, the therapeutic agents can improve the quality of life and/or prolong the survival time for patients with the disease or condition.

BRIEF SUMMARY OF THE INVENTION

The invention provides nitroxyl donor compounds and compositions that are useful in treating and/or preventing the onset and/or development of diseases or conditions that are responsive to nitroxyl therapy, such as heart failure, ischemia/reperfusion injury and cancer.

In one aspect, the invention provides compounds of the formula (I):

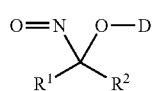

(I)

where each $R^1$ and $R^2$ is independently a substituted or unsubstituted $C_1$-$C_8$ alkyl, substituted or unsubstituted $C_2$-$C_8$ alkenyl, substituted or unsubstituted $C_2$-$C_8$ alkynyl, or $R^1$ and $R^2$ are taken together to form an unsubstituted or substituted 6 or 7-membered carbocyclic moiety or an unsubstituted or substituted 5, 6 or 7-membered heterocyclic moiety; and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$; provided that the compound is other than 1-nitrosocycloheptyl acetate, 1-nitrosocycloheptyl benzoate, 9-nitrosobicyclo[3.3.1]nonan-9-yl acetate or 8-methyl-3-nitroso-8-azabicyclo[3.2.1]octan-3-yl acetate; and (i) when $R^1$ or $R^2$ is an unsubstituted $C_1$-$C_8$ alkyl, the $R^1$ or $R^2$ that is an unsubstituted $C_1$-$C_8$ alkyl is other than methyl or propyl and D is other than an NSAID moiety; (ii) when $R^1$ and $R^2$ are taken together to form an unsubstituted 6-membered carbocyclic moiety, D is other than n-alkyl-C(O)—, ClCH$_2$—C(O)—, CCl$_3$—C(O)—, CF$_3$—C(O)—, (CH$_3$)$_3$C—C(O)—, alkenyl-C(O)—, substituted alkenyl-C(O)—, unsubstituted aryl-C(O)—, mono-substituted aryl-C(O)— or an NSAID moiety; (iii) when $R^1$ and $R^2$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iv) when $R^1$ and $R^2$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyan, or salts or solvates thereof.

In one variation, the invention provides a method of treating a disease or condition that is responsive to nitroxyl therapy, such as treating an individual who has heart failure, ischemia/reperfusion injury or cancer by administering to the individual a therapeutically effective amount of a compound of formula (I), where each $R^1$ and $R^2$ is independently a substituted or unsubstituted $C_1$-$C_8$ alkyl, substituted or unsubstituted $C_2$-$C_8$ alkenyl, substituted or unsubstituted $C_2$-$C_8$ alkynyl, or $R^1$ and $R^2$ are taken together to form an unsubstituted or substituted 6 or 7-membered carbocyclic moiety or an unsubstituted or substituted 5, 6 or 7-membered heterocyclic moiety; and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$.

In one embodiment, the invention embraces compounds of the formula (II):

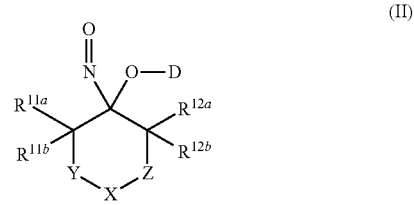

(II)

where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$; X is O, NR$^4$, CR$^5$R$^6$, S, S(O) or S(O)$_2$; Y is CR$^5$R$^6$ or CR$^5$R$^6$—CR$^7$R$^8$; Z is CR$^5$R$^6$ or a bond, provided that when X is CR$^5$R$^6$, Z is CR$^5$R$^6$; R$^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl; and each R$^5$, R$^6$, R$^7$, R$^8$, R$^{11a}$, R$^{11b}$, R$^{12a}$, and R$^{12b}$ is independently H, substituted or unsubstituted $C_1$-$C_8$ alkyl, halo, hydroxyl, alkoxy, cyano, nitro, or is taken together with a geminal R group to form a carbonyl moiety, or is taken together with a vicinal R group to form a bond, or is taken together with another R group to form a ring; provided that the compound is other than 1-nitrosocycloheptyl acetate, 1-nitrosocycloheptyl benzoate, 9-nitrosobicyclo[3.3.1]nonan-9-yl acetate or 8-methyl-3-nitroso-8-azabicyclo[3.2.1]octan-3-yl acetate; and (i) when X, Y, Z, R$^{11a}$, R$^{11b}$, R$^{12a}$, and R$^{12b}$ are taken together to form an unsubstituted 6-membered carbocyclic moiety, D is other than n-alkyl-C(O)—, ClCH$_2$—C(O)—, CCl$_3$—C(O)—, CF$_3$—C(O)—, (CH$_3$)$_3$C—C(O)—, alkenyl-C(O)—, substituted alkenyl-C(O)—, unsubstituted aryl-C(O)—, mono-substituted aryl-C(O)— or an NSAID moiety; (ii) when X, Y, Z, R$^{11a}$, R$^{11b}$, R$^{12a}$, and R$^{12b}$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iii) when X, Y, Z, R$^{11a}$, R$^{11b}$, R$^{12a}$, and R$^{12b}$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyran; or salts or solvates thereof. In one variation, the compound is of formula (II) where X is O, NR$^4$, S, S(O) or S(O)$_2$.

In one variation, the invention provides a method of treating a disease or condition that is responsive to nitroxyl therapy, such as treating an individual who has heart failure, ischemia/reperfusion injury or cancer by administering to the individual a therapeutically effective amount of a compound of formula (II), where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$; X is O, NR$^4$, CR$^5$R$^6$, S, S(O) or S(O)$_2$; Y is CR$^5$R$^6$ or CR$^5$R$^6$—CR$^7$R$^8$; Z is CR$^5$R$^6$ or a bond, provided that when X is CR$^5$R$^6$, Z is CR$^5$R$^6$; R$^4$ is H, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted acyl, alkoxycarbonyl, substituted or unsubstituted heterocyclyl, substituted or unsubstituted aryl, substituted or R$^5$, R$^6$, R$^7$, R$^8$, R$^{11a}$, R$^{11b}$, R$^{12a}$, and R$^{12b}$ unsubstituted aralkyl, or sulfonyl; and each R$^5$, R$^6$ is independently H, substituted or unsubstituted C$_1$-C$_8$ alkyl, halo, hydroxyl, alkoxy, cyano, nitro, or is taken together with a geminal R group to form a carbonyl moiety, or is taken together with a vicinal R group to form a bond, or is taken together with another R group to form a ring.

In another aspect, the invention provides a pharmaceutical composition comprising a compound of the invention and a pharmaceutically acceptable carrier. In one embodiment, the pharmaceutical composition is suitable for parenteral administration, e.g., aqueous or non-aqueous sterile injection solutions. In one variation, the pharmaceutical composition is acidic, e.g. an aqueous composition having a pH of about 5.5 to about 7.

In yet another aspect, the invention provides a method of treating a disease or condition that is responsive to nitroxyl therapy comprising administering to an individual having a disease or condition that is responsive to nitroxyl therapy a therapeutically effective amount of a compound of the invention or a pharmaceutically acceptable salt thereof. This invention embraces methods of delivering a therapeutically effective amount of nitroxyl administering a compound of the invention in a suitable dose. In one embodiment, the condition is heart failure. In another embodiment, the condition is ischemia/reperfusion injury. In one embodiment, the invention provides a method for treating a patient having a cancerous disease comprising administering to the patient a therapeutically effective amount of a compound of the invention or a pharmaceutically acceptable salt thereof. In another embodiment, the cancerous disease is a breast cancer, a pancreatic cancer, a prostate cancer or a colorectal cancer.

DETAILED DESCRIPTION OF THE INVENTION

Definitions

Unless clearly indicated otherwise, the following terms as used herein have the meanings indicated below.

Use of the terms "a", "an" and the like refers to one or more.

"Alkyl" intends a linear saturated hydrocarbon structure having 1 to 20 carbon atoms, preferably 1 to 12 carbon atoms and more preferably 1 to 8 carbon atoms or 1 to 4 carbon atoms. "Alkyl" also intends a branched or cyclic hydrocarbon structure having 3 to 20 carbon atoms, preferably 3 to 12 carbon atoms and more preferably 3 to 8 carbon atoms. For any use of the term "alkyl," unless clearly indicated otherwise, it is intended to embrace all variations of alkyl groups disclosed herein, as measured by the number of carbon atoms, the same as if each and every alkyl group was explicitly and individually listed for each usage of the term. When the alkyl group is cyclic, it may also be referred to as a cycloalkyl group and have e.g., 3 to 20 annular carbon atoms, preferably 3 to 12 annular carbon atoms and more preferably 3 to 8 annular carbon atoms. When an alkyl residue having a specific number of carbons is named, all geometric isomers having that number of carbons are intended to be encompassed; thus, for example, "butyl" is meant to include n-butyl, sec-butyl, iso-butyl and t-butyl; "propyl" includes n-propyl and iso-propyl. Examples of alkyl groups include methyl, ethyl, n-propyl, i-propyl, t-butyl, n-heptyl, octyl, cyclopentyl, cyclopropyl, cyclobutyl, norbornyl, and the like. Alkyl is also used herein to denote an alkyl residue as part of a larger functional group and when so used, is taken together with other atoms to form another functional group. For instance, reference to —C(O)O-alkyl intends an ester functional group, where the alkyl portion of the moiety may be any alkyl group, and provide by way of example only, the functional group —C(O)OCH$_3$, —C(O)OCH(CH$_3$)$_2$ and the like. Another example of an alkyl group as part of a larger structure includes the residue —NHC(O)-alkyl-C(O)OH, which e.g., may be —NHC(O)CH$_2$CH$_2$C(O)OH when alkyl is —CH$_2$CH$_2$—.

"Alkenyl" is understood to refer to a group of 2 or more carbon atoms, such as 2 to 10 carbon atoms and more preferably 2 to 6 carbon atoms and having at least one and preferably from one to two double bonds. Examples of an alkenyl group include —C=CH$_2$, —CH$_2$CH=CHCH$_3$ and —CH$_2$CH=CH—CH=CH$_2$.

"Alkynyl" refers to alkynyl group preferably having from 2 to 10 carbon atoms and more preferably 3 to 6 carbon atoms and having at least one triple bond, such as the moiety —C≡CH.

"Substituted alkyl" refers to an alkyl group having from 1 to 5 substituents. For instance, an alkyl group substituted with a group such as halo, nitro, cyano, oxo, aryl, alkoxy, alkoxycarbonyl, acyl, acyloxy, acylamino, amino, hydroxyl, carboxyl, carboxylalkyl, thiol, thioalkyl, heterocyclyl, —OS(O)$_2$-alkyl, and the like is a substituted alkyl. The substituent may be further substituted, for example, by halo, hydroxy, alkyl, alkoxy, aryl, substituted aryl, substituted alkyl, substituted aralkyl, and the like. Likewise, "substituted alkenyl" and "substituted alkynyl" refer to alkenyl or alkynyl groups having 1 to 5 substituents.

"Aryl" intends a monocyclic, bicyclic or tricyclic aromatic hydrocarbon ring system having 6 to 14 carbon atoms. Examples of groups whose radicals are aryl groups include, e.g., benzene, naphthalene, indane and tetralin.

"Heteroaryl" refers to an aromatic ring system having at least one annular heteroatom selected from O, N, or S. An heteroaryl group is preferably a 5- or 6-membered aromatic ring containing 1-3 annular heteroatoms selected from O, N, or S; a bicyclic 9- or 10-membered aromatic ring system (meaning the ring system has 9 or 10 annular atoms) containing 1-3 annular heteroatoms selected from O, N, or S; or a tricyclic 13- or 14-membered aromatic ring system (meaning the ring system has 13 or 14 annular atoms) containing 1-3 annular heteroatoms selected from O, N, or S. Examples of groups whose radicals are heteroaryl groups include e.g., imidazole, pyridine, indole, thiophene, benzopyranone, thiazole, furan, benzimidazole, benzoxazole, benzthiazole, quinoline, isoquinoline, quinoxaline, pyrimidine, pyrazine, tetrazole and pyrazole.

"Substituted aryl" refers to an aryl group having from 1 to 5 substituents. For instance, an aryl group substituted with 1 to 5 groups such as halo, nitro, cyano, oxo, aryl, alkoxy, alkyl, acyl, acylamino, amino, hydroxyl, carboxyl, carboxylalkyl, thiol, thioalkyl, heterocyclyl, —OS(O)$_2$-alkyl, and the like is a substituted aryl. Likewise, "substituted heteroaryl" refers to heteroaryl groups having 1 to 5 substituents.

"Aralkyl" refers to a residue in which an aryl moiety is attached to the parent structure via an alkyl residue. "Aralkenyl" and "aralkynyl" residues refer to aryl moieties attached to the parent structure via an alkenyl or alkynyl residue, respectively. Examples include benzyl (—CH$_2$-Ph), phenethyl (—CH$_2$CH$_2$Ph), phenylvinyl (—CH=CH-Ph), phenylallyl and the like.

"Heterocyclyl" or "heterocyclic" refers to a ring system having at least one annular heteroatom selected from O, N, or S. Examples of heterocycles whose radicals are heterocyclyl groups include tetrahydropyran, morpholine, pyrrolidine, piperidine, thiazolidine, dioxane, tetrahydrofuran, tetrahydrofuranone and the like. A specific example of a heterocyclyl residue is tetrahydropyranyl.

"Substituted heterocyclyl" or "substituted heterocyclic" refers to a heterocyclyl group having from 1 to 5 substituents. For instance, a heterocyclyl group substituted with 1 to 5 groups such as halo, nitro, cyano, oxo, aryl, alkoxy, alkyl, acyl, acylamino, amino, hydroxyl, carboxyl, carboxylalkyl, thiol, thioalkyl, heterocyclyl, —OS(O)$_2$-alkyl, and the like is a substituted heterocyclyl. A particular example of a substituted heterocyclyl is N-methylpiperazinyl.

"Acyl" refers to and includes the groups —C(O)H, —C(O)alkyl, —C(O)substituted alkyl, —C(O)alkenyl, —C(O)substituted alkenyl, —C(O)alkynyl, —C(O)substituted alkynyl, —C(O)cycloalkyl, —C(O)substituted cycloalkyl, —C(O)aryl, —C(O)substituted aryl, —C(O)heteroaryl, —C(O)substituted heteroaryl, —C(O)heterocyclic, and —C(O)substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclyl and substituted heterocyclyl are as defined herein.

"Halo" refers to fluoro, chloro, bromo or iodo.

"Perhaloalkyl" refers to an alkyl group where each H of the hydrocarbon is replaced with halo. Examples of perhaloalkyl groups include —CF$_3$, CF$_2$Cl and —CF$_2$CF$_3$ and the like.

"Alkoxy" refers to an alkyl group that is connected to the parent structure through an oxygen atom (—O-alkyl). When a cycloalkyl group is connected to the parent structure through an oxygen atom, the group may also be referred to as a cycloalkoxy group. Examples include methoxy, ethoxy, propoxy, isopropoxy, cyclopropyloxy, cyclohexyloxy and the like. A "perhaloalkoxy" intends a perhaloalkyl group attached to the parent structure through an oxygen, such as the residue —O—CF$_3$.

"Aryloxy" refers to an aryl group that is connected to the parent structure through an oxygen atom (—O-aryl), which by way of example includes the residues phenoxy, naphthoxy, and the like. "Substituted aryloxy" refers to a substituted aryl group connected to the parent structure through an oxygen atom (—O-substituted aryl).

As used herein the term "substituent" or "substituted" means that a hydrogen radical on a compound or group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom.

Examples of substituents include, but are not limited to, halogen (F, Cl, Br, or I), hydroxyl, amino, alkylamino, arylamino, alkoxycarbonylamino, acylamino, dialkylamino, diarylamino, cyano, nitro, mercapto, oxo (=O), thioxo (=S), or imino (=N-alkyl), formyl, carbamoyl, carboxyl, thioureido, thiocyanato, aminosulfonyl, alkylsulfonyl, arylsulfonyl, alkyl, alkenyl, alkoxy, mercaptoalkoxy, aryl, heteroaryl, cyclyl, heterocyclyl, acyl, acyloxy, alkoxycarbonyl, wherein alkyl, alkenyl, alkoxy, aryl, heteroaryl, cyclyl, and heterocyclyl are optionally substituted with alkyl, aryl, heteroaryl, halogen, hydroxyl, amino, mercapto, cyano, nitro, oxo, thioxo, or imino. In other embodiments, substituents on any group (such as, for example, alkyl, substituted alkyl, alkenyl, substituted alkenyl, alkynyl, substituted alkynyl, aryl, substituted aryl, aralkyl, substituted aralkyl, heteroaryl, substituted heteroaryl, heteroaralkyl, substituted heteroaralkyl, cycloalkyl, substituted cycloalkyl, heterocycloalkyl, substituted heterocycloalkyl, heterocyclyl and substituted heterocyclyl) can be at any atom of that group (such as on a carbon atom of the primary carbon chain of a substituted alkyl group or on a substituent already present on a substituted alkyl group) or at any atom of, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo, carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamoyl, thioureido, thiocyanato, sulfoamido, sulfonylalkyl, sulfonylaryl, or mercaptoalkoxy. Additional suitable substituents on alkyl, alkenyl, alkynyl, aryl, aralkyl, heteroaryl, heteroaralkyl, cycloalkyl, cyclyl, heterocycloalkyl, and heterocyclyl.

"Geminal" refers to the relationship between two moieties that are attached to the same atom. For example, in the residue —CH$_2$—CR'R"—, R' and R" are geminal and R' may be referred to as a geminal R group to R". As an illustrative example, when R' is taken together with a geminal R group, e.g. R" in the residue CR'R" to form a carbonyl moiety, the residue is C=O.

"Vicinal" refers to the relationship between two moieties that are attached to adjacent atoms. For example, in the residue —CHR'—CHR"—, R' and R" are vicinal and R' may be referred to as a vicinal R group to R". As an illustrative example, when R' is taken together with a vicinal R group, e.g. R" in the residue —CHR'—CHR"— to form a bond, the residue is —CH=CH—.

"Pharmaceutically acceptable salt" refers to pharmaceutically acceptable salts of a compound described herein, such as a compound of Formula (I), (II), (III) or (IV) or other nitroxyl donor of the invention, which salts may be derived from organic and inorganic acids, such as hydrochloride, hydrobromide, tartrate, mesylate, acetate, maleate, oxalate and the like; when the molecule contains an acid functionality, salts may be derived from a variety of organic or inorganic counter ions well known in the art and include, by way of example only, sodium, potassium, calcium, magnesium, ammonium, tetraalkylammonium, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt may be prepared from a compound of any one of the formulae disclosed herein having a basic functional group, such as an amino functional group, and a pharmaceutically acceptable inorganic or organic acid. Suitable acids include sulfuric acid, citric acid, acetic acid, hydrochloric acid, hydrogen bromide, hydrogen iodide, nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid. A salt may also be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributylamine; pyridine; N-methyl-N-ethylamine; diethylamine; triethylamine; mono-, bis-, or tris-(2-hydroxy-lower alkyl amines), such as mono-, bis-, or tris(2-hydroxyethyl)amine, or tris-(hydroxymethyl)methylamine, N,N-di-lower alkyl-N-(hydroxy lower alkyl)-amines, such as N,N-dimethyl-N-(2-hydroxyethyl)amine, or N-methyl-D-glucamine; and amino acids such as arginine, lysine, and the like.

Unless clearly indicated otherwise, "an individual" as used herein intends a mammal, including but not limited to a human. For example, an individual may have or is suspected of having a disease or condition that are responsive to nitroxyl therapy, including heart failure, ischemia/reperfusion injury and cancer.

The term "effective amount" intends such amount of a compound or a pharmaceutically acceptable salt thereof, which in combination with its parameters of efficacy and toxicity, as well as based on the knowledge of the practicing specialist should be effective in a given therapeutic form. As is understood in the art, an effective amount may be in one or more doses.

As used herein, "treatment" or "treating" is an approach for obtaining a beneficial or desired result, including clinical results. For purposes of this invention, beneficial or desired results include but are not limited to inhibiting and/or suppressing the onset and/or development of a disease or condition that is responsive to nitroxyl therapy or reducing the severity of such disease or condition, such as reducing the number and/or severity of symptoms associated with the disease or condition, increasing the quality of life of those suffering from the disease or condition, decreasing the dose of other medications required to treat the disease or condition, enhancing the effect of another medication an individual is taking for the disease or condition and prolonging survival of individuals having the disease or condition. The disease or condition may be a cardiovascular disease or condition, which includes, but is not limited to, coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Related symptoms that may be alleviated by the methods herein include shortness of breath, fatigue, swollen ankles or legs, angina, loss of appetite, weight gain or loss, associated with aforementioned diseases or disorders. The disease or condition may involve ischemia/reperfusion injury. The disease or condition may be a cancerous disease or condition, which includes, but is not limited to, breast, prostate, pancreatic or colorectal cancer.

As used herein, "preventing" refers to reducing the probability of developing a disorder or condition in an individual who does not have, but is at risk of developing a disorder or condition.

An individual "at risk" may or may not have a detectable disease or condition, and may or may not have displayed a detectable disease or condition prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). For example, an individual with a family history of heart disease, uncontrolled hypertension (high blood pressure), physical inactivity, obesity (more than 20% over one's ideal body weight) or uncontrolled diabetes may be at risk for heart diseases.

"Nitroxyl" refers to the species HNO.

As used herein, a compound is a "nitroxyl donor" if it donates nitroxyl under physiological conditions. Preferably, the nitroxyl donor is capable of donating an effective amount of nitroxyl in vivo and has a safety profile indicating the compound would be tolerated by an individual in the amount necessary to achieve a therapeutic effect. One of ordinary skill in the art would be able to determine the safety of administering particular compounds and dosages to live subjects. One skilled in the art may also determine whether a compound, is a nitroxyl donor by evaluating whether it releases HNO under physiological conditions. Compounds are easily tested for nitroxyl donation with routine experiments. Although it is impractical to directly measure whether nitroxyl is donated, several tests are accepted for determining whether a compound donates nitroxyl. For example, the compound of interest can be placed in solution, for example in water, in a sealed container. After sufficient time for disassociation has elapsed, such as from several minutes to several hours, the headspace gas is withdrawn and analyzed to determine its composition, such as by gas chromatography and/or mass spectroscopy. If the gas $N_2O$ is formed (which occurs by HNO dimerization, see Smith, P. A. S. and Hein, G. E. *J. Am. Chem. Soc.* 1960, 82, 5731-5740; and Kohout, F. C. and Lampe, F. W. *J. Am. Chem. Soc.* 1965, 87, 5795-5796), the test is positive for nitroxyl donation and the compound is a nitroxyl donor. The level of nitroxyl donating ability may be expressed as a percentage of a compound's theoretical maximum. A compound that donates a "significant level of nitroxyl" intends a compound that donates 40% or more or 50% or more of its theoretical maximum amount of nitroxyl. In one variation, the compounds for use herein donate 60% or more of the theoretical maximum amount of nitroxyl. In another variation, the compounds for use herein donate 70% or more of the theoretical maximum amount of nitroxyl. In another variation, the compounds for use herein donate 80% or more of the theoretical maximum amount of nitroxyl. In another variation, the compounds for use herein donate 90% or more of the theoretical maximum amount of nitroxyl. In yet another variation, the compounds for use herein donate between about 70% and about 90% of the theoretical maximum amount of nitroxyl. In yet another variation, the compounds for use herein donate between about 85% and about 95% of the theoretical maximum amount of nitroxyl. In yet another variation, the compounds for use herein donate between about 90% and about 95% of the theoretical maximum amount of nitroxyl. Compounds that donate less than 40% or less than 50% of their theoretical amount of nitroxyl are still nitroxyl donors and may be used in the invention disclosed herein. A compound that donates less than 50% of the theoretical amount of nitroxyl may be used in the methods described, and may require higher dosing levels as compared to compounds that donate a significant level of nitroxyl. Alternatively, HNO formation from compounds of the invention can be assessed by the ability of the compounds to reductively nitrosylate ferric heme groups yielding the relatively stable ferrous nitrosyl complexes as judged by ultraviolet/visible (UV/Vis) and Electron Paramagnetic Resonance (EPR) spectroscopies (Sha, X. et al *J. Am. Chem. Soc.* 2006, 128, 9687-9692). Nitroxyl donation also can be detected by exposing the test compound to metmyoglobin ($Mb^{3+}$). Nitroxyl reacts with $Mb^{3+}$ to form an $Mb^{2+}$-NO complex, which can be detected by changes in the ultraviolet/visible spectrum or by Electron Paramagnetic Resonance (EPR). The $Mb^{2+}$-NO complex has an EPR signal centered around a g-value of about 2. Nitric oxide, on the other hand, reacts with $Mb^{3+}$ to form an $Mb^{3+}$-NO complex that is EPR silent. Accordingly, if the candidate compound reacts with $Mb^{3+}$ to form a complex detectable by common methods such as ultraviolet/visible or EPR, then the test is positive for nitroxyl donation. Testing for nitroxyl donation may be performed at physiologically relevant pH.

A "positive inotrope" as used herein is an agent that causes an increase in myocardial contractile function. Such an agent includes a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also intended. For example, U.S. Pat. No. 4,663,351 describes a dobutamine prodrug that can be administered orally. One of ordinary skill in the art would be able to determine if a compound is capable of causing positive inotropic effects and also additional beta-agonist compounds. In particular embodiments, the beta-receptor agonist is selective for the beta-1 receptor. However, in other embodiments the beta-agonist is selective for the beta-2 receptor, or is not selective for any particular receptor.

Diseases or conditions that are "responsive to nitroxyl therapy" intends any disease or condition in which administration of a compound that donates an effective amount of nitroxyl under physiological conditions treats and/or prevents the disease or condition, as those terms are defined herein. A disease or condition whose symptoms are suppressed or diminished upon administration of nitroxyl donor is a disease or condition responsive to nitroxyl therapy. Non-limiting examples of diseases or conditions that are responsive to nitroxyl therapy include coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Other cardiovascular diseases or conditions are also intended, as are diseases or conditions that implicate ischemia/reperfusion injury. Cancer is another example of disease or condition that is responsive to nitroxyl therapy.

Nitroxyl Donor Compounds

The compounds disclosed herein are a novel class of nitroxyl donors that release HNO under physiological conditions.

Preferably, a compound of this invention releases efficacious amounts of HNO at a controlled rate under physiological conditions. For example, the rate of HNO release from an acyloxy nitroso compound of this invention may be modulated by varying the nature of the acyloxy group and the structure bearing the nitroso moiety.

In one embodiment, the invention embraces a compound of the formula (I):

where each $R^1$ and $R^2$ is independently a substituted or unsubstituted $C_1$-$C_8$ alkyl, substituted or unsubstituted $C_2$-$C_8$ alkenyl, substituted or unsubstituted $C_2$-$C_8$ alkynyl, or $R^1$ and $R^2$ are taken together to form an unsubstituted or substituted 6 or 7-membered carbocyclic moiety or an unsubstituted or substituted 5, 6 or 7-membered heterocyclic moiety;

D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(O$C_1$-$C_8$alkyl)$_2$;

provided that the compound is other than 1-nitrosocycloheptyl acetate, 1-nitrosocycloheptyl benzoate, 9-nitrosobicyclo[3.3.1]nonan-9-yl acetate or 8-methyl-3-nitroso-8-azabicyclo[3.2.1]octan-3-yl acetate; and (i) when $R^1$ or $R^2$ is an unsubstituted $C_1$-$C_8$ alkyl, the $R^1$ or $R^2$ that is an unsubstituted $C_1$-$C_8$ alkyl is other than methyl or propyl and D is other than an NSAID moiety; (ii) when $R^1$ and $R^2$ are taken together to form an unsubstituted 6-membered carbocyclic moiety, D is other than n-alkyl-C(O)—, ClCH$_2$—C(O)—, CCl$_3$—C(O)—, CF$_3$—C(O)—, (CH$_3$)$_3$C—C(O)—, alkenyl-C(O)—, substituted alkenyl-C(O)—, unsubstituted aryl-C(O)—, mono-substituted aryl-C(O)— or an NSAID moiety; (iii) when $R^1$ and $R^2$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iv) when $R^1$ and $R^2$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyan;

or a salt or solvate thereof.

In another embodiment, the compound is of the formula (I) where each $R^1$ and $R^2$ is independently a substituted $C_1$-$C_8$ alkyl. In one embodiment, the compound is of the formula (I) where each $R^1$ and $R^2$ is independently a moiety of the formula $C_1$-$C_4$alkyl-O—$C_1$-$C_4$alkyl- or acyl-O—$C_1$-$C_4$alkyl-. In one specific embodiment, the compound of the formula (I), where $R^1$ and $R^2$ are each of the formula $CH_3CH_2$—O—$CH_2$— or $CH_3C(O)$—O—$CH_2$—. In a more specific embodiment, the compound of the formula (I), where $R^1$ and $R^2$ are each of the formula $CH_3CH_2$—O—$CH_2$— or $CH_3C(O)$—O—$CH_2$— and D is alkyl-C(O)—, e.g. acetyl.

In one embodiment, the invention embraces a compound of the formula (I), where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—. In one variation, the compound is of formula (I), where D is as described in this paragraph and each $R^1$ and $R^2$ is independently a substituted $C_1$-$C_8$ alkyl. In another variation of this embodiment, each $R^1$ and $R^2$ is independently a moiety of the formula $C_1$-$C_4$alkyl-O—$C_1$-$C_4$alkyl- or acyl-O—$C_1$-$C_4$alkyl-. In one specific variation, $R^1$ and $R^2$ are each of the formula $CH_3CH_2$—O—$CH_2$— or $CH_3C(O)$—O—$CH_2$—.

In one embodiment, the invention embraces a compound of the formula (I), where D is unsubstituted $C_1$-$C_4$alkyl-C(O)—, perhaloalkyl-C(O)—, substituted aryl-C(O)—, substituted aralkyl-C(O)—, or substituted $C_1$-$C_4$alkyl-C(O)— where the substitution is one or more substituents selected from the group consisting of halo, cyano, alkoxy, acyloxy, substituted acyloxy [e.g. $CH_3OCH_2CH_2OCH_2C(O)O$—], acylamino, substituted acylamino, alkylamino, substituted alkylamino, dialkylamino, N-acyl-substituted alkylamino [e.g. $(AcOCH_2)_2CHN(Ac)$—], N-alkyl-substituted alkylamino [e.g. $(AcOCH_2)_2CHN(Me)$-], alkoxycarbonylamino [e.g. t-BuOC(O)NH—], substituted alkoxycarbonylamino [e.g. $PhCH_2OC(O)NH$—], alkoxycarbonyl, heterocyclyl and substituted heterocyclyl. In one variation, D is a di-substituted $C_1$-$C_4$alkyl-C(O)— where the $C_1$-$C_4$alkyl-C(O)— is of the formula

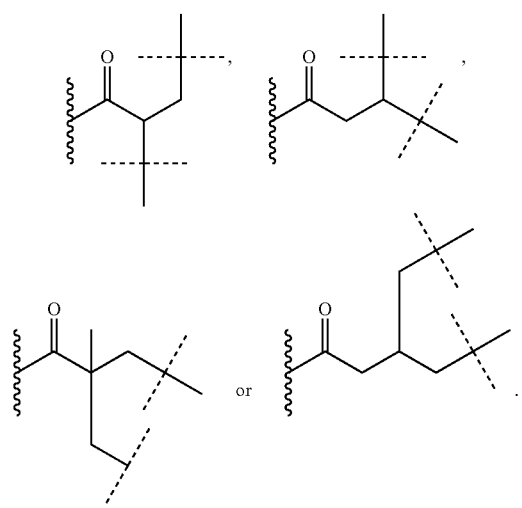

In one variation, the compound is of formula (I), where D is as described in this paragraph and each $R^1$ and $R^2$ is independently a substituted $C_1$-$C_8$ alkyl. In another variation of this embodiment, each $R^1$ and $R^2$ is independently a moiety of the formula $C_1$-$C_4$alkyl-O—$C_1$-$C_4$alkyl- or acyl-O—$C_1$-$C_4$alkyl-. In one specific variation, $R^1$ and $R^2$ are each of the formula $CH_3CH_2$—O—$CH_2$— or $CH_3C(O)$—O—$CH_2$—.

In one embodiment, the invention embraces a compound of the formula (I), where D is $C_1$-$C_8$alkyl-C(O)—. In one variation of this embodiment, each $R^1$ and $R^2$ is independently a substituted $C_1$-$C_8$ alkyl. In another variation of this embodiment, each $R^1$ and $R^2$ is independently a moiety of the formula $C_1$-$C_4$alkyl-O—$C_1$-$C_4$alkyl- or acyl-O—$C_1$-$C_4$alkyl-. In one specific variation, the compound is of formula (I), where D is $C_1$-$C_8$alkyl-C(O)— and $R^1$ and $R^2$ are each of the formula $CH_3CH_2$—O—$CH_2$— or $CH_3C(O)$—O—$CH_2$—.

In one embodiment, the invention embraces a compound of the formula (I), where D is a moiety of the formula:

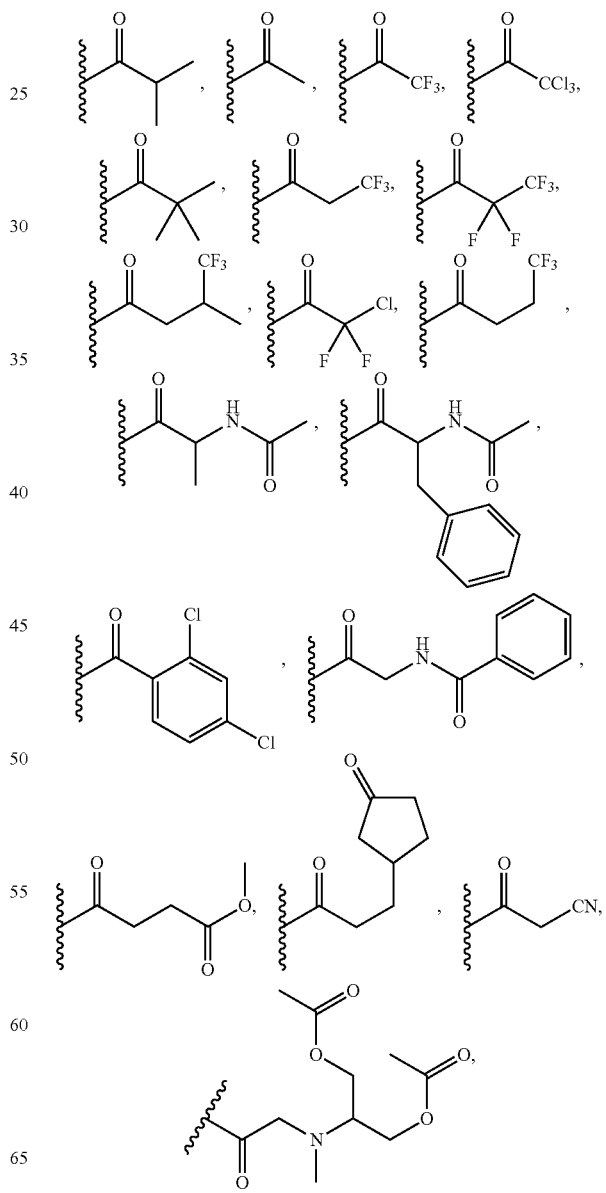

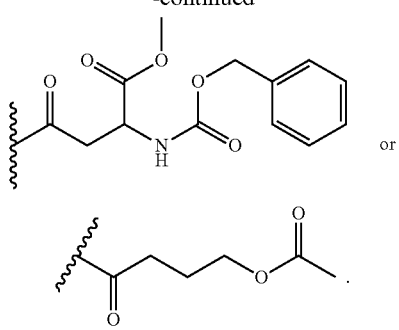
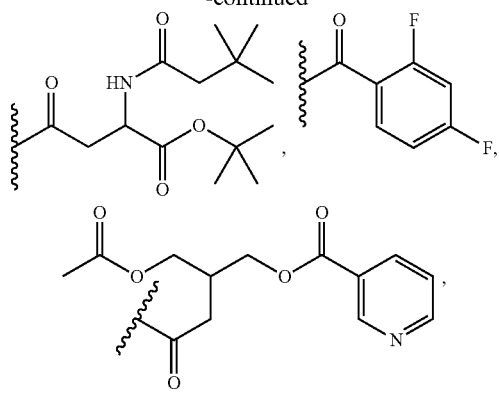
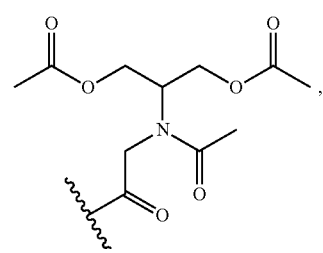
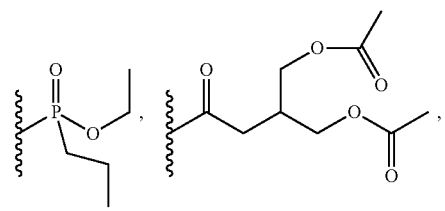
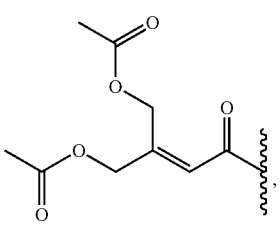
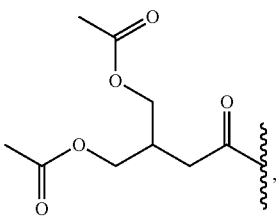
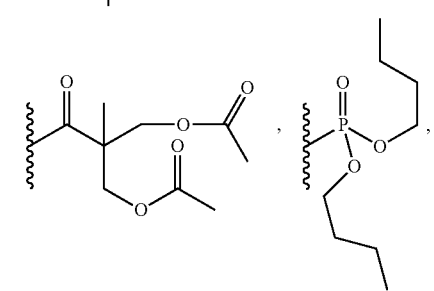
In another embodiment, the compound is of the formula (I), where D is a moiety of the formula:
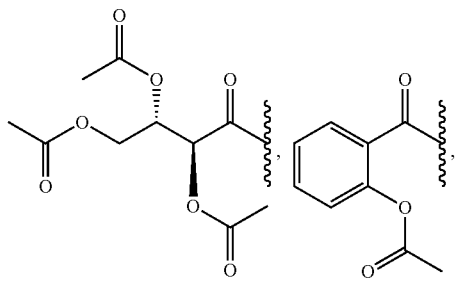
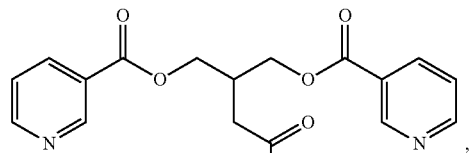
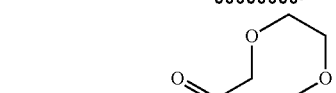
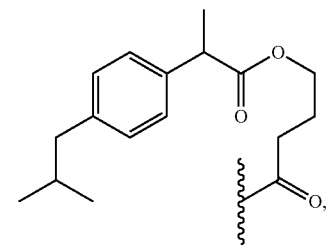
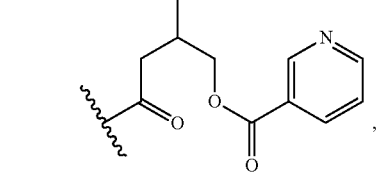
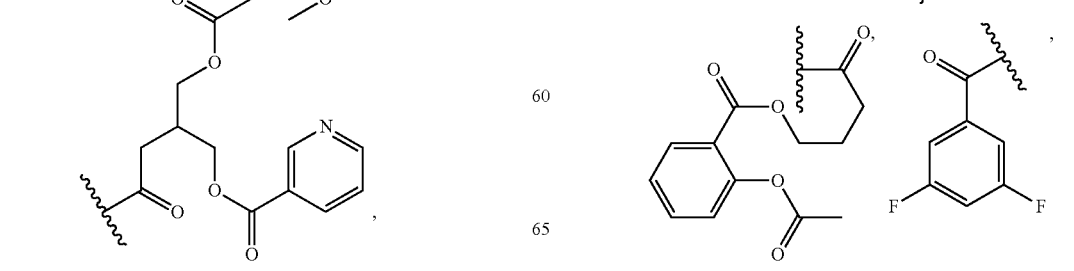
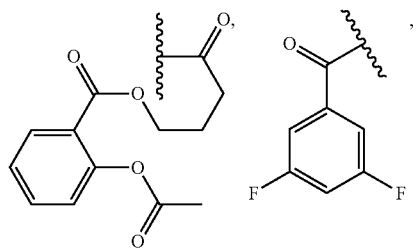

-continued

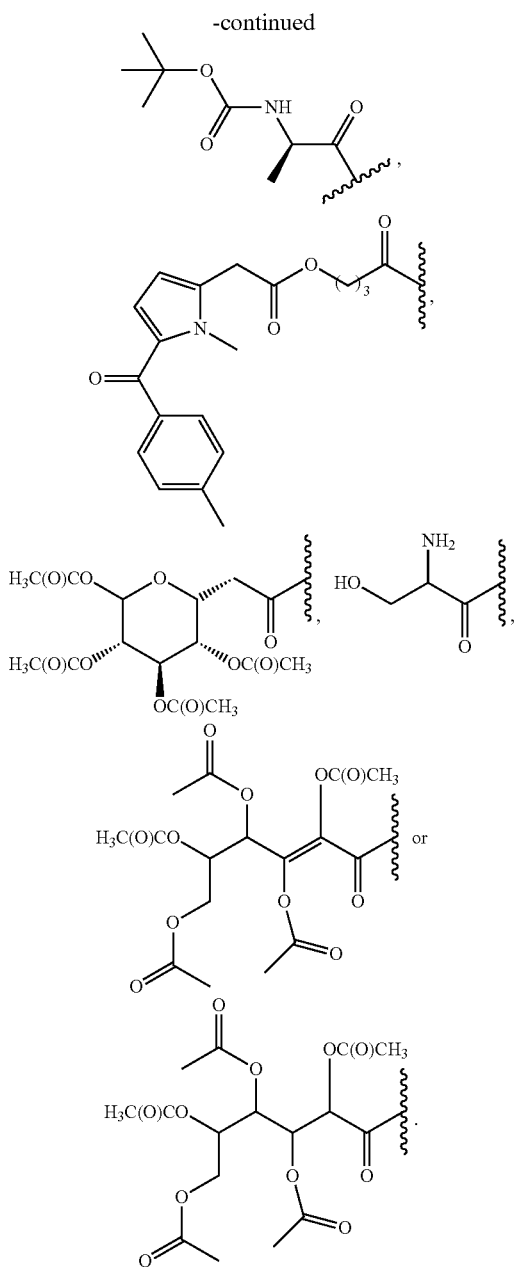

In one embodiment, the invention embraces a compound of the formula (I), where D is CH₃—C(O)—. In another embodiment, the compound is of the formula (I), where D is P(O)(OC₁-C₈alkyl)₂.

In another embodiment, the invention embraces a compound of the formula (Ia):

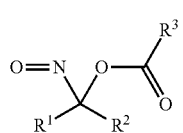

(Ia)

where $R^3$ is unsubstituted or substituted alkyl, perhaloalkyl, unsubstituted or substituted alkenyl, unsubstituted or substituted alkynyl, unsubstituted or substituted aryl, unsubstituted or substituted heteroaryl or heterocyclyl. $R^1$ and $R^2$ of formula (Ia) are as defined for formula (I).

In yet another embodiment, the compound is of the formula (Ia), where $R^3$ is $C_1$-$C_8$alkyl. In one specific embodiment, the compound is of the formula (Ia), where $R^3$ is methyl.

In one embodiment, the invention embraces a compound of the formula (II):

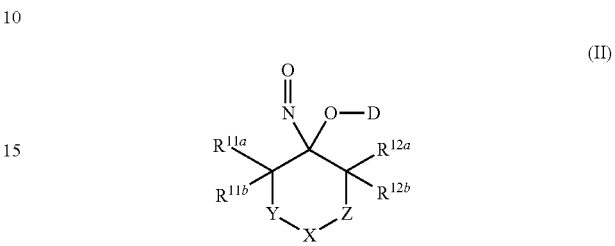

(II)

where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC₁-C₈alkyl)₂;

X is O, $NR^4$, $CR^5R^6$, S, S(O) or $S(O)_2$;

Y is $CR^5R^6$ or $CR^5R^6$—$CR^7R^8$;

Z is $CR^5R^6$ or a bond, provided that when X is $CR^5R^6$, Z is $CR^5R^6$;

$R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl;

each $R^5$, $R^6$, $R^7$, $R^8$, $R^{11a}$, $R^{11b}$, $R^{12a}$, and $R^{12b}$ is independently H, substituted or unsubstituted $C_1$-$C_8$ alkyl, halo, hydroxyl, alkoxy, cyano, nitro, or is taken together with a geminal R group to form a carbonyl moiety, or is taken together with a vicinal R group to form a bond, or is taken together with another R group to form a ring;

provided that the compound is other than 1-nitrosocycloheptyl acetate, 1-nitrosocycloheptyl benzoate, 9-nitrosobicyclo[3.3.1]nonan-9-yl acetate or 8-methyl-3-nitroso-8-azabicyclo[3.2.1]octan-3-yl acetate; and (i) when X, Y, Z, $R^{11a}$, $R^{11b}$, $R^{12a}$, and $R^{12b}$ are taken together to form an unsubstituted 6-membered carbocyclic moiety, D is other than n-alkyl-C(O)—, ClCH₂—C(O)—, CCl₃—C(O)—, CF₃—C(O)—, (CH₃)₃C—C(O)—, alkenyl-C(O)—, substituted alkenyl-C(O)—, unsubstituted aryl-C(O)—, monosubstituted aryl-C(O)— or an NSAID moiety; (ii) when X, Y, Z, $R^{11a}$, $R^{11b}$, $R^{12a}$, and $R^{12b}$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iii) when X, Y, Z, $R^{11a}$, $R^{11b}$, $R^{12a}$, and $R^{12b}$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyran;

or a salt or solvate thereof.

In another embodiment, the compound is of the formula (II), where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—.

In one embodiment, the invention embraces a compound of the formula (II), where D is unsubstituted $C_1$-$C_4$alkyl-C(O)—, perhaloalkyl-C(O)—, substituted aryl-C(O)—, substituted aralkyl-C(O)—, or substituted $C_1$-$C_4$alkyl-C(O)— where the substitution is one or more substituents selected from the group consisting of halo, cyano, alkoxy, acyloxy, substituted acyloxy [e.g. $CH_3OCH_2CH_2OCH_2C(O)O$—], acylamino, substituted acylamino, alkylamino, substituted alkylamino, dialkylamino, N-acyl-substituted alkylamino [e.g. $(AcOCH_2)_2CHN(Ac)$—], N-alkyl-substituted alkylamino [e.g. $(AcOCH_2)_2CHN(Me)$-], alkoxycarbonylamino [e.g. t-BuOC(O)NH—], substituted alkoxycarbonylamino [e.g. $PhCH_2OC(O)NH$—], alkoxycarbonyl, heterocyclyl and substituted heterocyclyl. In one variation, D is a di-substituted $C_1$-$C_4$alkyl-C(O)— where the $C_1$-$C_4$alkyl-C(O)— moiety is of the formula

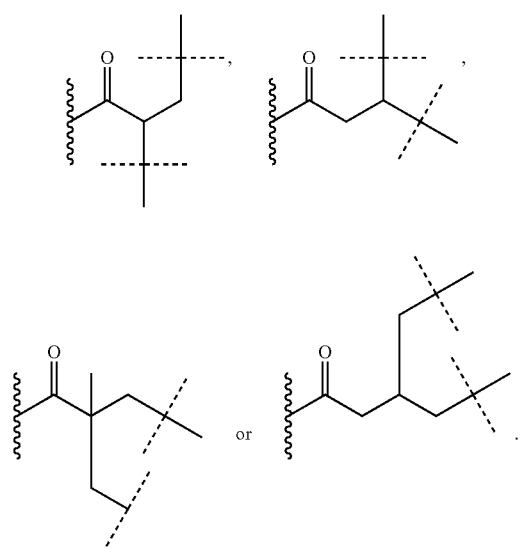

In another embodiment, the invention embraces a compound of the formula (II), where D is a moiety of the formula:

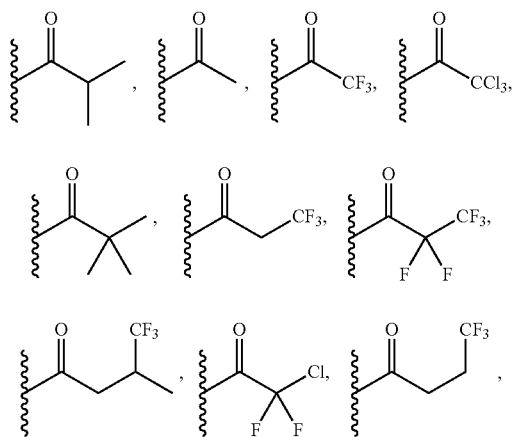

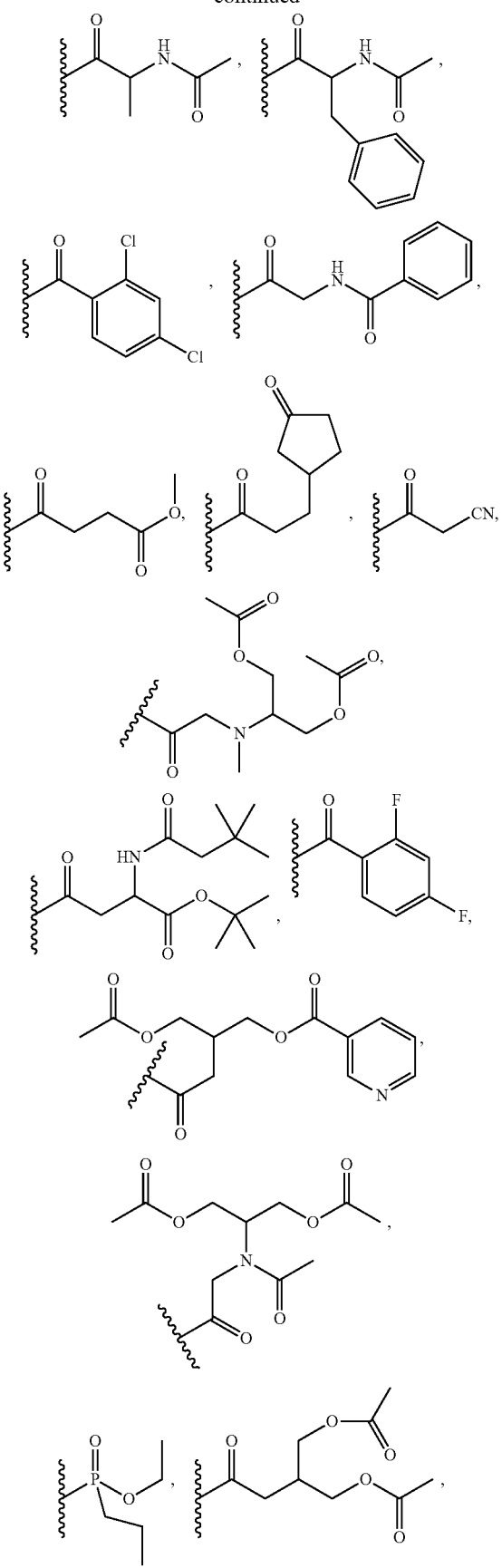

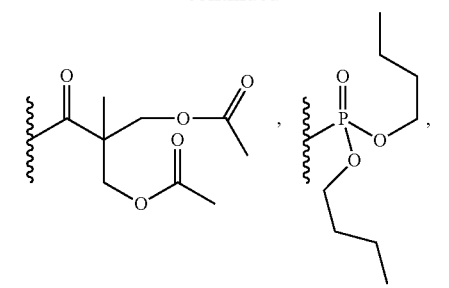 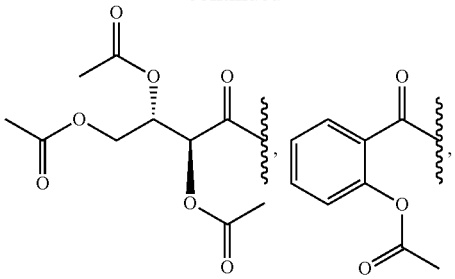
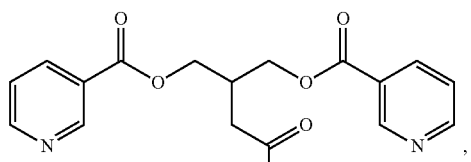
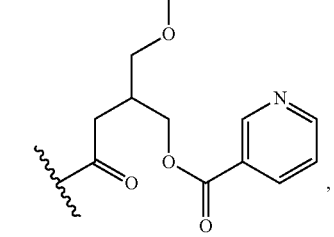
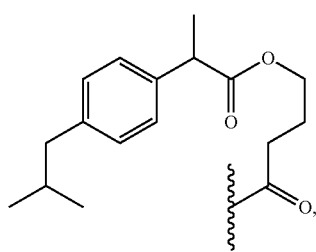
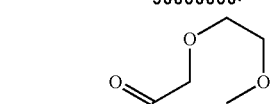
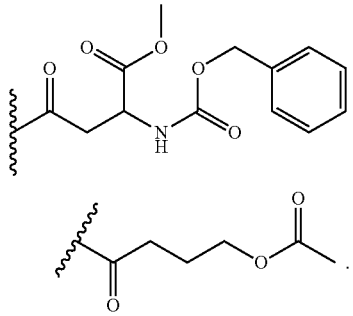
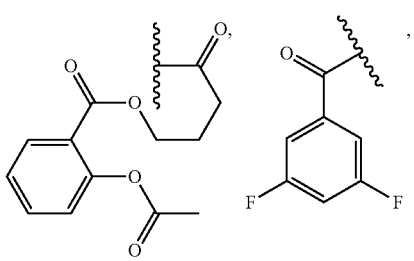
or
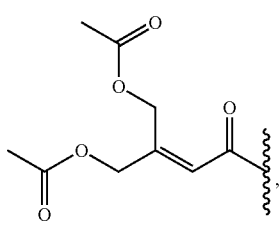
In another embodiment, the compound is of the formula (II), where D is a moiety of the formula:
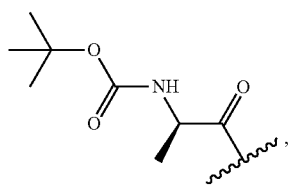
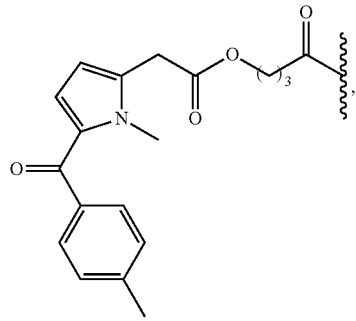
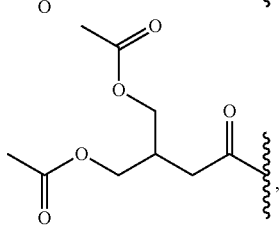
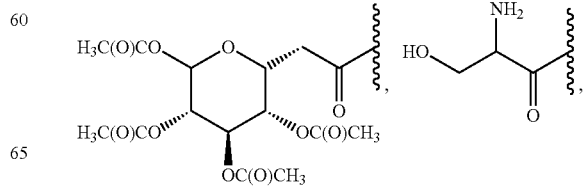

25

-continued

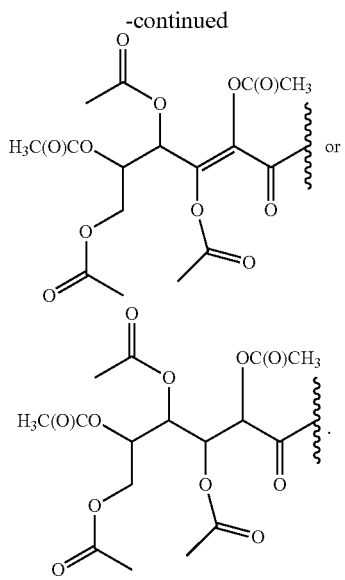

or

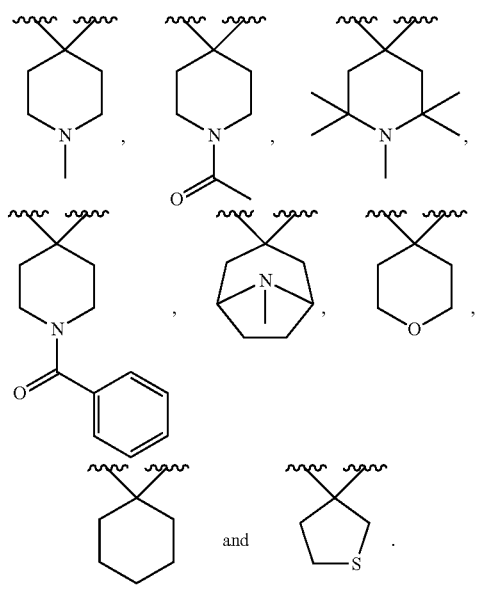

In another embodiment, the compound is of the formula (II), where D is $P(O)(OC_1-C_8alkyl)_2$. In one embodiment, the compound is of the formula (II), where D is selected from $P(O)(OCH_2CH_3)_2$ and $P(O)(OCH_2CH_2CH_2CH_3)_2$.

In some embodiments, the compound is of the formula (II) or any variations described herein, where X, Y, Z, $R^{11a}$, $R^{11b}$, $R^{12a}$, and $R^{12b}$ are taken together to form a moiety of the structure selected from:

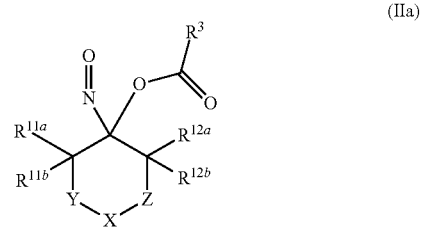

and

In one variation, the compound is of the formula (II) where X is O and Y and Z are each $CR^5R^6$ where each $R^5$ and $R^6$ is independently H, substituted or unsubstituted $C_1-C_8$ alkyl, halo, hydroxyl, alkoxy, cyano, nitro, or is taken together with a geminal R group to form a carbonyl moiety. In one such variation, each Y and Z is $CH_2$. In a specific variation, each Y and Z is $CH_2$ and each $R^{11a}$, $R^{11b}$, $R^{12a}$, and $R^{12b}$ is H. In one specific variation, the compound is of the formula (II), where X is O, each Y and Z is $CH_2$, each $R^{11a}$, $R^{11b}$, $R^{12a}$, and $R^{12b}$ is H, and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)— and heterocyclyl-C(O)—.

26

In another variation, the compound is of the formula (II) where X is $NR^4$, and Y and Z are each $CR^5R^6$ where each $R^5$ and $R^6$ is independently H, substituted or unsubstituted $C_1-C_8$ alkyl, halo, hydroxyl, alkoxy, cyano, nitro, or is taken together with a geminal R group to form a carbonyl moiety. In one such variation, X is $NR^4$ where $R^4$ is substituted or unsubstituted $C_1-C_8$ alkyl (e.g. methyl) or substituted or unsubstituted acyl (e.g. acetyl or benzoyl). In another such variation, each $R^5$ and $R^6$ is independently H, or $C_1-C_8$ alkyl (e.g. methyl). In yet another such variation, each $R^{11a}$, $R^{11b}$, $R^{12a}$, and $R^{12b}$ is H. In one specific variation, the compound is of the formula (II) where X is $NR^4$ where $R^4$ is substituted or unsubstituted $C_1-C_8$ alkyl or substituted or unsubstituted acyl, Y and Z are each $CR^5R^6$ where each $R^5$ and $R^6$ is independently H, or $C_1-C_8$ alkyl, each $R^{11a}$, $R^{11b}$, $R^{12a}$, and $R^{12b}$ is H and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —$P(O)(OC_1-C_8alkyl)_2$.

In another variation, the compound is of the formula (II) where X, Y and Z are each $CR^5R^6$ where each $R^5$ and $R^6$ is independently H, substituted or unsubstituted $C_1-C_8$ alkyl, halo, hydroxyl, alkoxy, cyano, nitro, or is taken together with a geminal R group to form a carbonyl moiety. In one such variation, each $R^5$ and $R^6$ is H. In another such variation, each $R^{11a}$, $R^{11b}$, $R^{12a}$, and $R^{12b}$ is H. In one specific variation, the compound is of the formula (II) where X, Y and Z are each $CH_2$, each $R^{11a}$, $R^{11b}$, $R^{12a}$, and $R^{12b}$ is H and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —$P(O)(OC_1-C_8alkyl)_2$; provided that D is other than n-alkyl-C(O)—, $ClCH_2$—C(O)—, $CCl_3$—C(O)—, $CF_3$—C(O)—, $(CH_3)_3C$—C(O)—, alkenyl-C(O)—, substituted alkenyl-C(O)—, unsubstituted aryl-C(O)—, mono-substituted aryl-C(O)— or an NSAID moiety.

In yet another variation, the compound is of the formula (II) where X is S, S(O) or $S(O)_2$, Z is a bond and Y is $CR^5R^6$ where each $R^5$ and $R^6$ is independently H, substituted or unsubstituted $C_1-C_8$ alkyl, halo, hydroxyl, alkoxy, cyano, nitro, or is taken together with a geminal R group to form a carbonyl moiety. In one such variation, Y is $CH_2$. In another such variation, each $R^{11a}$, $R^{11b}$, $R^{12a}$, and $R^{12b}$ is H. In one specific variation, the compound is of the formula (II) where X is S, Y is $CH_2$, Z is a bond, each $R^{11a}$, $R^{11b}$, $R^{12a}$, and $R^{12b}$ is H and D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —$P(O)(OC_1-C_8alkyl)_2$.

In one embodiment, the invention embraces a compound of the formula (IIa):

(IIa)

where $R^3$ is unsubstituted or substituted alkyl, perhaloalkyl, unsubstituted or substituted alkenyl, unsubstituted or substituted alkynyl, unsubstituted or substituted aryl, unsubstituted or substituted heteroaryl or heterocyclyl;

X is O, $NR^4$, $CR^5R^6$, S, S(O) or $S(O)_2$;

Y is $CR^5R^6$ or $CR^5R^6-CR^7R^8$;

Z is $CR^5R^6$ or a bond, provided that when X is $CR^5R^6$, Z is $CR^5R^6$;

$R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl;

each $R^5$, $R^6$, $R^7$, $R^8$, $R^{11a}$, $R^{11b}$, $R^{12a}$, and $R^{12b}$ is independently H, substituted or unsubstituted $C_1$-$C_8$ alkyl, halo, hydroxyl, alkoxy, cyano, nitro, or is taken together with a geminal R group to form a carbonyl moiety, or is taken together with a vicinal R group to form a bond, or is taken together with another R group to form a ring;

provided that the compound is other than 1-nitrosocycloheptyl acetate, 1-nitrosocycloheptyl benzoate, 9-nitrosobicyclo[3.3.1]nonan-9-yl acetate or 8-methyl-3-nitroso-8-azabicyclo[3.2.1]octan-3-yl acetate; and (i) when X, Y, Z, $R^{11a}$, $R^{11b}$, $R^{12a}$, and $R^{12b}$ are taken together to form an unsubstituted 6-membered carbocyclic moiety, D is other than n-alkyl-C(O)—, $ClCH_2$—C(O)—, $CCl_3$—C(O)—, $CF_3$—C(O)—, $(CH_3)_3C$—C(O)—, alkenyl-C(O)—, substituted alkenyl-C(O)—, unsubstituted aryl-C(O)—, mono-substituted aryl-C(O)— or an NSAID moiety; (ii) when X, Y, Z, $R^{11a}$, $R^{11b}$, $R^{12a}$, and $R^{12b}$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iii) when X, Y, Z, $R^{11a}$, $R^{11b}$, $R^{12a}$, and $R^{12b}$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyran;

or a salt or solvate thereof

In one embodiment, the compound is of the formula (II) or formula (IIa), where X is O, $NR^4$, S, S(O) or $S(O)_2$. In one variation, X is O. In another variation, X is S. In yet another variation, X is $NR^4$, such as where X is an N-unsubstituted $C_1$-$C_8$alkyl, N-carbonyl-$C_1$-$C_4$alkyl or N-carbonyl-aryl.

In one embodiment, the invention embraces a compound of the formula (III):

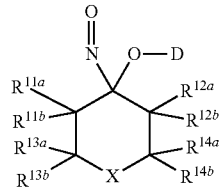

(III)

where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)($OC_1$-$C_8$alkyl)$_2$;

X is O, $NR^4$, $CR^5R^6$, S, S(O) or $S(O)_2$;

$R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl; and each $R^5$, $R^6$, $R^{11a}$, $R^{11b}$, $R^{12a}$, $R^{12b}$, $R^{13a}$, $R^{13b}$, $R^{14a}$ and $R^{14b}$ is independently H, substituted or unsubstituted $C_1$-$C_8$ alkyl, halo, hydroxyl, alkoxy, cyano or nitro, or is taken together with a geminal R group to form a carbonyl moiety, or is taken together with a vicinal R group to form a bond when X is $CR^5R^6$, or is taken together with another R group to form a ring;

provided that the compound is other than 9-nitrosobicyclo[3.3.1]nonan-9-yl acetate or 8-methyl-3-nitroso-8-azabicyclo[3.2.1]octan-3-yl acetate; and (i) when X, $R^{11a}$, $R^{11b}$, $R^{12a}$, $R^{12b}$, $R^{13a}$, $R^{13b}$, $R^{14a}$ and $R^{14b}$ are taken together to form an unsubstituted 6-membered carbocyclic moiety, D is other than n-alkyl-C(O)—, $ClCH_2$—C(O)—, $CCl_3$—C(O)—, $CF_3$—C(O)—, $(CH_3)_3C$—C(O)—, alkenyl-C(O)—, substituted alkenyl-C(O)—, unsubstituted aryl-C(O)—, mono-substituted aryl-C(O)— or an NSAID moiety; (ii) when X, $R^{11a}$, $R^{11b}$, $R^{12a}$, $R^{12b}$, $R^{13a}$, $R^{13b}$, $R^{14a}$ and $R^{14b}$ are taken together to form a substituted 6-membered carbocyclic moiety, the substituted 6-membered carbocyclic moiety is a monocyclic or bicyclic ring that is substituted with a moiety other than alkyl, nitroso, acyl, oxime, and substituted alkenyl; or (iii) when X, $R^{11a}$, $R^{11b}$, $R^{12a}$, $R^{12b}$, $R^{13a}$, $R^{13b}$, $R^{14a}$ and $R^{14b}$ are taken together to form an unsubstituted or substituted 5 or 6-membered heterocyclic moiety, the 5 or 6-membered heterocyclic moiety is a monocyclic or bicyclic ring other than dioxane or acyloxy-substituted tetrahydropyran; or a salt or solvate thereof.

In another embodiment, the compound is of the formula (III), where X is O, $NR^4$, S, S(O) or $S(O)_2$. In one variation, X is O. In another variation, X is $NR^4$, such as where X is an N-unsubstituted $C_1$-$C_8$alkyl, N-carbonyl-$C_1$-$C_4$alkyl or N-carbonyl-aryl.

In one embodiment, the invention embraces a compound of the formula (IV):

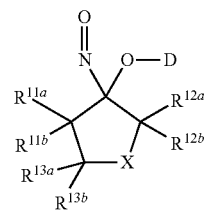

(IV)

where X is O, $NR^4$, S, S(O) or $S(O)_2$;

$R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl; and each $R^5$, $R^6$, $R^{11a}$, $R^{11b}$, $R^{12a}$, $R^{12b}$, $R^{13a}$ and $R^{13b}$ is independently H, substituted or unsubstituted $C_1$-$C_8$ alkyl, halo, hydroxyl, alkoxy, cyano or nitro, or is taken together with a geminal R group to form a carbonyl moiety, or is taken together with a vicinal R group to form a bond when X is $CR^5R^6$, or is taken together with another R group to form a ring;

or a salt or solvate thereof. In formula (IV), D is as defined for formula (I) or any variation thereof.

In some embodiments, the compound is of the formula (IV) where at least one, two, three, four, five or six of $R^{11a}$, $R^{11b}$, $R^{12a}$, $R^{12b}$, $R^{13a}$ and $R^{13b}$ are H. In some embodiments, the compound is of the formula (IV) where one, two, three, four, five or six of $R^{11a}$, $R^{11b}$, $R^{12a}$, $R^{12b}$, $R^{13a}$ and $R^{13b}$ are H. In a specific embodiment, the compound is of the formula (IV) where each $R^{11a}$, $R^{11b}$, $R^{12a}$, $R^{12b}$, $R^{13a}$ and $R^{13b}$ is H.

In another embodiment, the compound is of the formula (IV) where X is S. In some variations of this embodiment, at least one, two, three, four, five or six of $R^{11a}$, $R^{11b}$, $R^{12a}$, $R^{12b}$, $R^{13a}$ and $R^{13b}$ is H. In some variations of this embodiment, one, two, three, four, five or six of $R^{11a}$, $R^{11b}$, $R^{12a}$, $R^{12b}$, $R^{13a}$ and $R^{13b}$ is H. In one particular variation of this embodiment, each $R^{11a}$, $R^{11b}$, $R^{12a}$, $R^{12b}$, $R^{13a}$ and $R^{13b}$ is H.

In one embodiment, the invention embraces a compound of the formula (V):

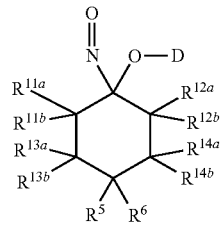

(V)

where D is selected from the group consisting of alkyl-C(O)—, substituted alkyl-C(O)—, perhaloalkyl-C(O)—, alkynyl-C(O)—, substituted alkynyl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$, provided that D is other than n-alkyl-C(O)—, ClCH$_2$—C(O)—, CCl$_3$—C(O)—, CF$_3$—C(O)—, (CH$_3$)$_3$C—C(O)—, mono-substituted aryl-C(O)— or an NSAID moiety; and each $R^5$, $R^6$, $R^{11a}$, $R^{11b}$, $R^{12a}$, $R^{12b}$, $R^{13a}$, $R^{13b}$, $R^{14a}$ and $R^{14b}$ is independently H, substituted or unsubstituted C$_1$-C$_8$ alkyl, halo, hydroxyl, alkoxy, cyano or nitro, or is taken together with a geminal R group to form a carbonyl moiety, or is taken together with a vicinal R group to form a bond, or is taken together with another R group to form a ring; or a salt or solvate thereof.

In some embodiments, the compound is of the formula (V), where at least one, two, three, four, five, six, seven, eight, nine or ten of $R^5$, $R^6$, $R^{11a}$, $R^{11b}$, $R^{12a}$, $R^{12b}$, $R^{13a}$, $R^{13b}$, $R^{14a}$ and $R^{14b}$ are H. In some embodiments, the compound is of the formula (V) where one, two, three, four, five, six, seven, eight, nine or ten of $R^5$, $R^6$, $R^{11a}$, $R^{11b}$, $R^{12a}$, $R^{12b}$, $R^{13a}$, $R^{13b}$, $R^{14a}$ and $R^{14b}$ are H. In one specific embodiment, the compound is of the formula (V), where each $R^5$, $R^6$, $R^{11a}$, $R^{11b}$, $R^{12a}$, $R^{12b}$, $R^{13a}$, $R^{13b}$, $R^{14a}$ and $R^{14b}$ is H.

In one specific embodiment, the compound is of the formula (V), having a structure of formula (Va):

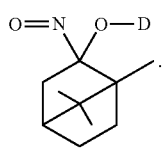

(Va)

In one embodiment, the invention embraces a compound of the formula (V), where D is a moiety of the formula:

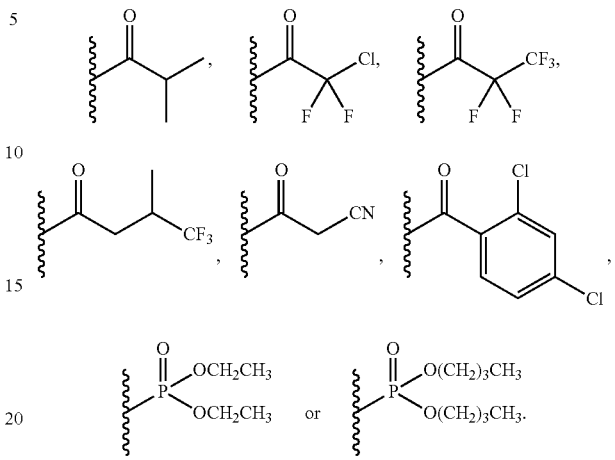

In one variation, the compound is of formula (V), where D is as described in this paragraph and $R^5$, $R^6$, $R^{11a}$, $R^{11b}$, $R^{12a}$, $R^{12b}$, $R^{13a}$, $R^{13b}$, $R^{14a}$ and $R^{14b}$ H. In another variation of this embodiment, each $R^5$, $R^6$, $R^{11a}$, $R^{11b}$, $R^{12a}$, $R^{12b}$, $R^{13a}$, $R^{13b}$, $R^{14a}$ and $R^{14b}$ is H, $R^{12a}$ is CH$_3$, and $R^{12b}$ and $R^{13b}$ are taken together to form C(CH$_3$)$_2$.

In one embodiment, the invention embraces a compound of the formula (VI):

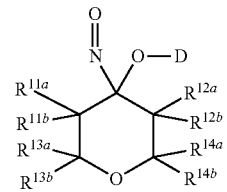

(VI)

where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$; and each $R^{11a}$, $R^{11b}$, $R^{12a}$, $R^{12b}$, $R^{13a}$, $R^{13b}$, $R^{14a}$ and $R^{14b}$ is independently H, substituted or unsubstituted C$_1$-C$_8$ alkyl, halo, hydroxyl, alkoxy, cyano or nitro, or is taken together with a geminal R group to form a carbonyl moiety, or is taken together with another R group to form a ring;

or a salt or solvate thereof

In some embodiments, the compound is of the formula (VI), where at least one, two, three, four, five, six, seven or eight of $R^{11a}$, $R^{11b}$, $R^{12a}$, $R^{12b}$, $R^{13a}$, $R^{13b}$, $R^{14a}$ and $R^{14b}$ are H. In some embodiments, the compound is of the formula (VI), where one, two, three, four, five, six, seven or eight of $R^{11a}$, $R^{11b}$, $R^{12a}$, $R^{12b}$, $R^{13a}$, $R^{13b}$, $R^{14a}$ and $R^{14b}$ are H. In one specific embodiment, the compound is of the formula (VI), where each $R^{11b}$, $R^{12a}$, $R^{12b}$, $R^{13a}$, $R^{13b}$, $R^{14a}$ and $R^{14b}$ is H.

In one embodiment, the compound is of the formula (VI), where D is a moiety of the formula:
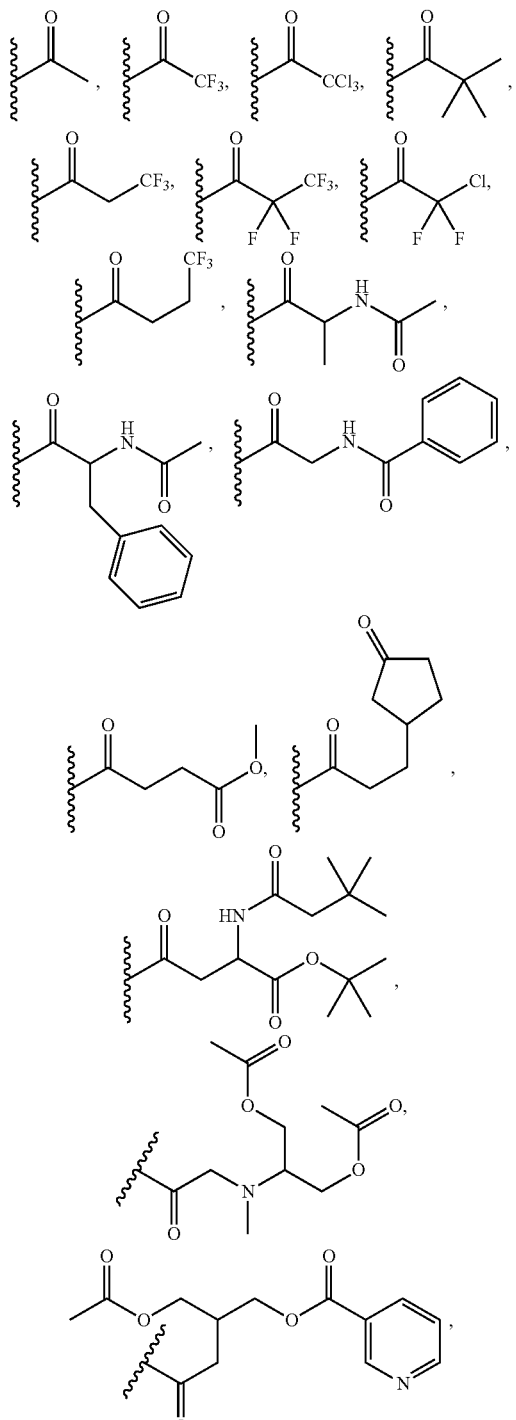
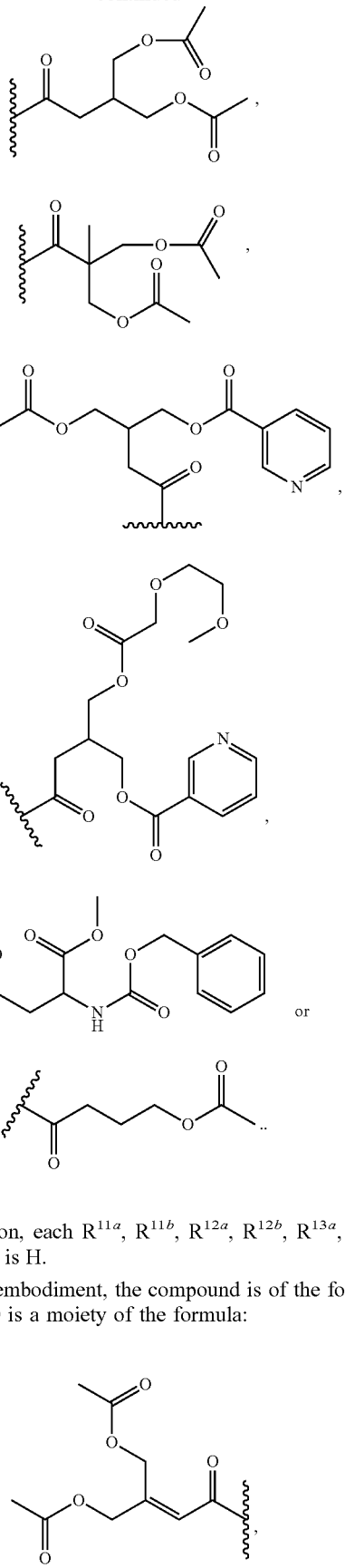
In one variation, each $R^{11a}$, $R^{11b}$, $R^{12a}$, $R^{12b}$, $R^{13a}$, $R^{13b}$, $R^{14a}$ and $R^{14b}$ is H.
In another embodiment, the compound is of the formula (VI), where D is a moiety of the formula:
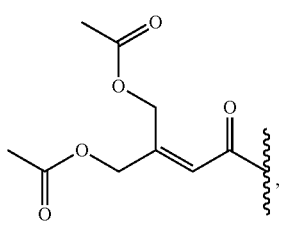

-continued

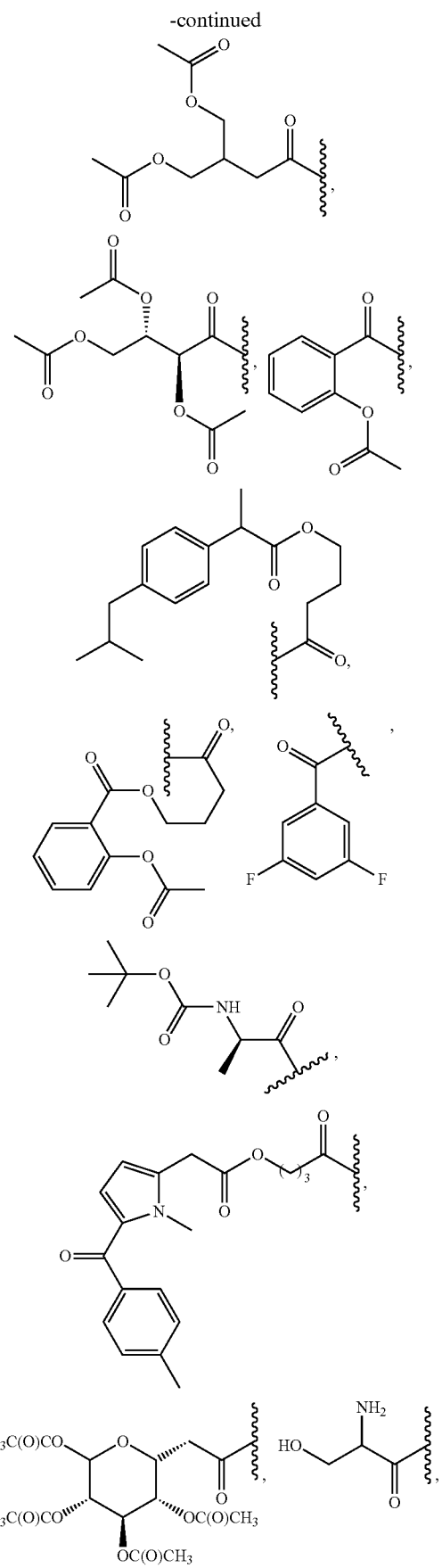

-continued

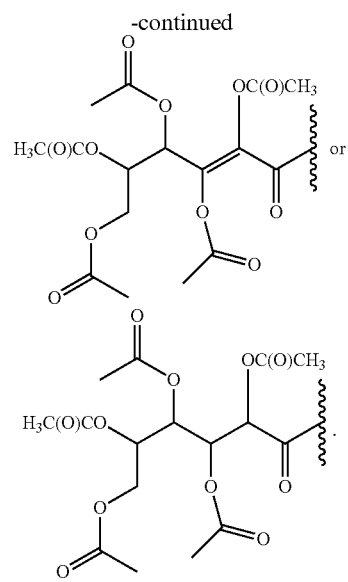

In one variation of this embodiment, each $R^{11a}$, $R^{11b}$, $R^{12a}$, $R^{12b}$, $R^{13a}$, $R^{13b}$, $R^{14a}$ and $R^{14b}$ is H.

In one variation, the compound is of the formula (VI), having a structure of formula (VIa):

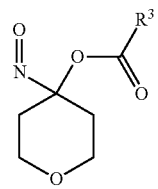

(VIa)

where $R^3$ is unsubstituted or substituted alkyl, perhaloalkyl, unsubstituted or substituted alkenyl, unsubstituted or substituted alkynyl, unsubstituted or substituted aryl, unsubstituted or substituted heteroaryl or heterocyclyl.

In one variation, the compound is of the formula (VIa) where $R^3$ is an unsubstituted $C_1$-$C_8$ alkyl or a $C_1$-$C_8$ alkyl substituted with one or more substituents selected from the group consisting of halo, nitro, cyano, oxo, aryl, alkoxy, alkoxycarbonyl, acyl, acyloxy, acylamino, amino, hydroxyl, carboxyl, carboxylalkyl, thiol, thioalkyl, heterocyclyl, —OS(O)$_2$-alkyl, and the like. In a specific variation, the compound is of the formula (VIa) where $R^3$ is a $C_1$-$C_8$ alkyl substituted with 1 to 5 substituents selected from the group consisting of hydroxyl, alkoxy, acyloxy, acyl, carboxyl, carboxylalkyl, alkoxycarbonyl, and heterocyclyl.

In one specific embodiment, the compound is of the formula (VIb):

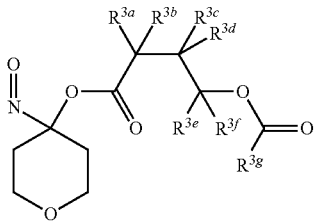

(VIb)

where each $R^{3a}$, $R^{3b}$, $R^{3c}$, $R^{3d}$, $R^{3e}$ and $R^{3f}$ is independently H, halo, hydroxyl, alkoxy, substituted alkoxy, acyl, acyloxy, unsubstituted or substituted alkyl, perhaloalkyl, unsubstituted or substituted alkenyl, unsubstituted or substituted alkynyl, unsubstituted or substituted aryl, unsubstituted or substituted heteroaryl, unsubstituted or substituted heterocyclyl, or is taken together with a geminal $R^{3a-f}$ and the carbon to which they are attached to form a carbonyl; and $R^{3g}$ is H, unsubstituted or substituted alkyl, perhaloalkyl, unsubstituted or substituted alkenyl, unsubstituted or substituted alkynyl, unsubstituted or substituted aryl, unsubstituted or substituted heteroaryl, unsubstituted or substituted heterocyclyl, or is taken together with one of $R^{3e}$ and $R^{3f}$ to form a lactone moiety;

or a salt or solvate thereof.

In some variations, the compound is of the formula (VIb) where each $R^{3a}$, $R^{3b}$, $R^{3c}$, $R^{3d}$, $R^{3e}$ and $R^{3f}$ is independently H, unsubstituted or substituted alkyl, hydroxyl, alkoxy, substituted alkoxy or acyloxy. In some variations, the compound is of the formula (VIb) where each $R^{3a}$, $R^{3b}$, $R^{3c}$, $R^{3d}$, $R^{3e}$ and $R^{3f}$ is independently H, unsubstituted or substituted alkyl, or acyloxy. In some variations, the compound is of the formula (VIb) where each $R^{3a}$, $R^{3b}$, $R^{3c}$, $R^{3d}$, $R^{3e}$ and $R^{3f}$ is independently H, acyloxy (e.g. acetoxy) or alkyl substituted with an acyloxy group (e.g. acetoxymethyl or nicotinoyloxymethyl). In some variations, at least one, two, three, four, five or six of $R^{3a}$, $R^{3b}$, $R^{3c}$, $R^{3d}$, $R^{3e}$ and $R^{3f}$ is H. In some variations, one, two, three, four, five or six of $R^{3a}$, $R^{3b}$, $R^{3c}$, $R^{3d}$, $R^{3e}$ and $R^{3f}$ is H. In some particular variations, one or two of $R^{3a}$, $R^{3b}$, $R^{3c}$, $R^{3d}$, $R^{3e}$ and $R^{3f}$ is independently acyloxy or alkyl substituted with an acyloxy group and each of the remaining $R^{3a}$, $R^{3b}$, $R^{3c}$, $R^{3d}$, $R^{3e}$ and $R^{3f}$ is H. In a particular variation, each $R^{3a}$, $R^{3b}$, $R^{3c}$, $R^{3d}$, $R^{3e}$ and $R^{3f}$ is H.

In some variations, the compound is of the formula (VIb) where $R^{3g}$ is H unsubstituted or substituted alkyl, perhaloalkyl, unsubstituted or substituted alkenyl, unsubstituted or substituted alkynyl, unsubstituted or substituted aryl, unsubstituted or substituted heteroaryl, or unsubstituted or substituted heterocyclyl. In some variations, the compound is of the formula (VIb) where $R^{3g}$ is unsubstituted or substituted alkyl, perhaloalkyl, unsubstituted or substituted aryl, unsubstituted or substituted heteroaryl, or unsubstituted or substituted heterocyclyl. In some variations, the compound is of the formula (VIb) where $R^{3g}$ is unsubstituted alkyl (e.g. methyl). In some variations, the compound is of the formula (VIb) where $R^{3g}$ is an alkyl substituted with alkoxy or substituted alkoxy (e.g. 2-methoxyethoxymethyl), or an alkyl substituted with aryl or substituted aryl (e.g. 1-(4-isobutylphenyl)ethyl). In some variations, the compound is of the formula (VIb) where $R^{3g}$ is a substituted or unsubstituted heteroaryl (e.g. pyridyl). In some specific variations, the compound is of the formula (VIb) where $R^{3g}$ is unsubstituted alkyl, one or two of $R^{3a}$, $R^{3b}$, $R^{3c}$, $R^{3d}$, $R^{3e}$ and $R^{3f}$ is acyloxy and each of the remaining $R^{3a}$, $R^{3b}$, $R^{3c}$, $R^{3d}$, $R^{3e}$ and $R^{3f}$ is H. In a particular variation, the compound is of the formula (VIb) where $R^{3g}$ is unsubstituted alkyl, $R^{3c}$ is acyloxy and each $R^{3a}$, $R^{3b}$, $R^{3d}$, $R^{3e}$ and $R^{3f}$ is H. In another particular variation, the compound is of the formula (VIb) where $R^{3g}$ is unsubstituted alkyl and each $R^{3a}$, $R^{3b}$, $R^{3c}$, $R^{3d}$, $R^{3e}$ and $R^{3f}$ is H.

In some variations, the compound is of the formula (VIb) where $R^{3g}$ is taken together with one of $R^{3e}$ and $R^{3f}$ to form a lactone moiety. In one such variation, $R^{3g}$ is taken together with one of $R^{3e}$ and $R^{3f}$ to form a five-membered lactone moiety (e.g. 5-oxotetrahydrofuan-2-yl). In another such variation, $R^{3g}$ is taken together with one of $R^{3e}$ and $R^{3f}$ to form a lactone moiety and the other one of $R^{3e}$ and $R^{3f}$ is H.

In a particular variation, the compound is of the formula (VIb) where $R^{3g}$ is taken together with one of $R^{3e}$ and $R^{3f}$ to form a lactone moiety and each $R^{3a}$, $R^{3b}$, $R^{3c}$, $R^{3d}$ and the other one of $R^{3e}$ and $R^{3f}$ is H. In a more particular variation, the compound is of the formula (VIb) where $R^{3g}$ is taken together with one of $R^{3e}$ and $R^{3f}$ to form a five-membered lactone moiety and each $R^{3a}$, $R^{3b}$, $R^{3c}$, $R^{3d}$ and the other one of $R^{3e}$ and $R^{3f}$ is H.

In a particular variation, compounds of the formula (VIc) are provided:

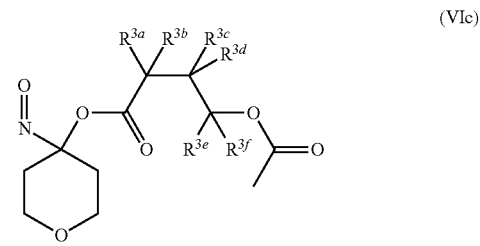

(VIc)

where $R^{3a}$, $R^{3b}$, $R^{3c}$, $R^{3d}$, $R^{3e}$ and $R^{3f}$ are as defined for formula (VIb) or any variation thereof. In one variation of formula (VIc), $R^{3e}$ and $R^{3f}$ are both H and $R^{3a}$, $R^{3b}$, $R^{3c}$, $R^{3d}$ are as defined for formula (VIb). In a further variation of formula (VIc), $R^{3e}$ and $R^{3f}$ are both H and $R^{3a}$, $R^{3b}$, $R^{3c}$, $R^{3d}$ are independently selected from H or a $C_1$-$C_8$ substituted alkyl. In one aspect of formula (VIc), $R^{3e}$ and $R^{3f}$ are both H, $R^{3d}$ is -alkyl-OMe and $R^{3a}$, $R^{3b}$, $R^{3c}$ are as defined for formula (VIb). In one such variation, $R^{3d}$ is —$(CH_2)_n$—OMe where n is an integer from 1 to 5.

In another particular variation, compounds of the formula (VId) are provided:

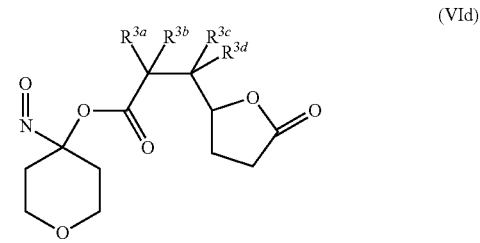

(VId)

where $R^{3a}$, $R^{3b}$, $R^{3c}$ and $R^{3d}$ are as defined for formula (VIb) or any variation thereof In one embodiment, the invention embraces a compound of the formula (VII):

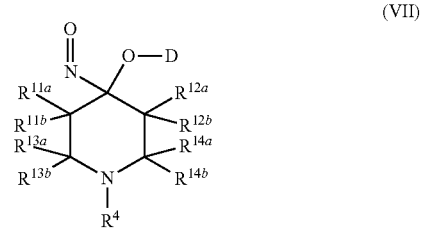

(VII)

where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)— and —P(O)(OC$_1$-C$_8$alkyl)$_2$;

$R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl; and each $R^{11a}$, $R^{11b}$, $R^{12a}$, $R^{12b}$, $R^{13a}$, $R^{13b}$, $R^{14a}$ and $R^{14b}$ is independently H, substituted or unsubstituted $C_1$-$C_8$ alkyl, halo, hydroxyl, alkoxy, cyano or nitro, or is taken together with a geminal R group to form a carbonyl moiety, or is taken together with another R group to form a ring;

provided that the compound is other than 8-methyl-3-nitroso-8-azabicyclo[3.2.1]octan-3-yl acetate;

or a salt or solvate thereof.

In one variation, compounds of the formula (VII) are provided where each $R^{11a}$, $R^{11b}$, $R^{12a}$, $R^{12b}$, $R^{13a}$, $R^{13b}$, $R^{14a}$ and $R^{14b}$ is independently H, substituted or unsubstituted $C_1$-$C_8$ alkyl, halo, hydroxyl, alkoxy, cyano or nitro, or is taken together with a geminal R group to form a carbonyl moiety.

In some embodiments, the compound is of the formula (VII), where at least one, two, three, four, five, six, seven or eight of $R^{11a}$, $R^{11b}$, $R^{12a}$, $R^{12b}$, $R^{13a}$, $R^{13b}$, $R^{14a}$ and $R^{14b}$ are H. In some embodiments, the compound is of the formula (VII), where one, two, three, four, five, six, seven or eight of $R^{11a}$, $R^{11b}$, $R^{12a}$, $R^{12b}$, $R^{13a}$, $R^{13b}$, $R^{14a}$ and $R^{14b}$ are H. In one specific embodiment, the compound is of the formula (VII), where each $R^{11a}$, $R^{11b}$, $R^{12a}$, $R^{12b}$, $R^{13a}$, $R^{13b}$, $R^{14a}$ and $R^{14b}$ is H.

In one embodiment, the compound is of the formula (VII), where $R^4$ is an unsubstituted $C_1$-$C_8$ alkyl or an acyl moiety. In another embodiment, the compound is of the formula (VII), where $R^4$ is an unsubstituted $C_1$-$C_4$ alkyl, $C_1$-$C_8$ alkyl-C(O)— or aryl-C(O)—. In one specific embodiment, the compound of the formula (VII), where $R^4$ is methyl, $CH_3C(O)$— or phenyl-C(O)—. In a further variation, each of $R^{11a}$, $R^{11b}$, $R^{12a}$, $R^{12b}$, $R^{13a}$, $R^{13b}$, $R^{14a}$ and $R^{14b}$ is H and $R^4$ is an unsubstituted $C_1$-$C_8$ alkyl such as methyl.

In another embodiment, the compound is of the formula (VII), where D is a moiety of the formula:

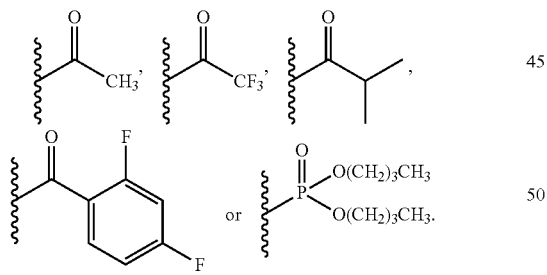

In some embodiments, the compound is of the formula (VII), where D is a moiety of the formula:

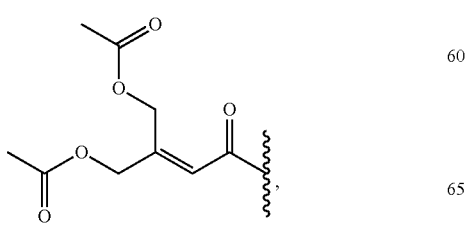

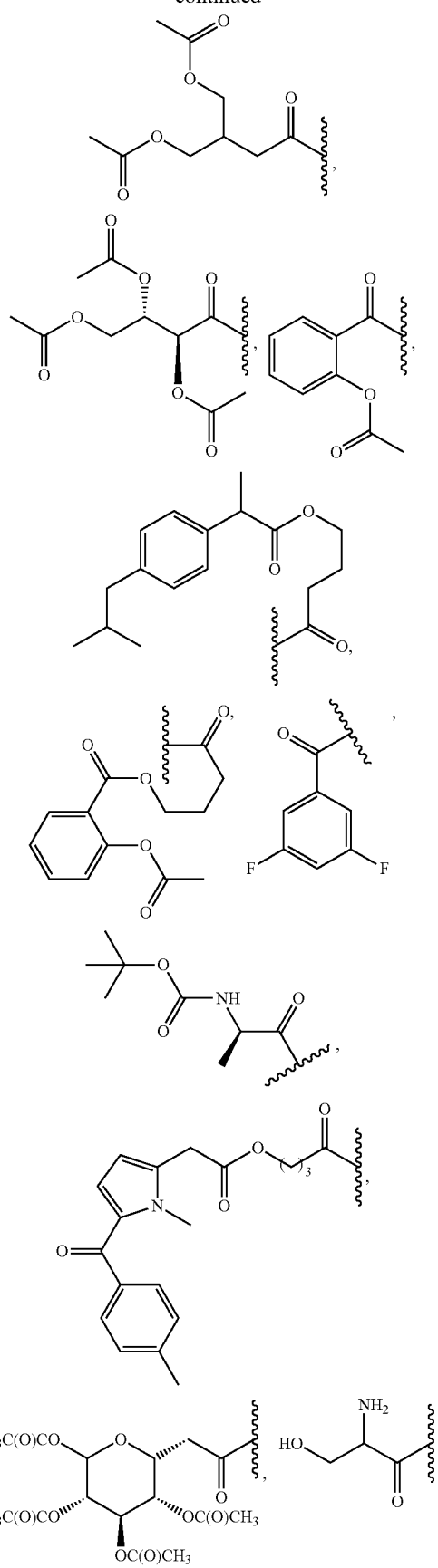

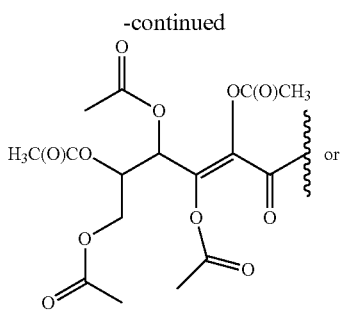

or

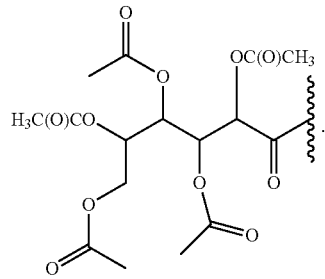

In one variation the compound is of formula (VII), where D is as described in any variations in this paragraph and each $R^{11a}$, $R^{11b}$, $R^{12a}$, $R^{12b}$, $R^{13a}$, $R^{13b}$, $R^{14a}$ and $R^{14b}$ is H. In another variation of this embodiment, $R^4$ is an unsubstituted $C_1$-$C_8$ alkyl or an acyl moiety. In yet another variation of this embodiment, $R^4$ is an unsubstituted $C_1$-$C_4$ alkyl, $C_1$-$C_8$ alkyl-C(O)— or aryl-C(O)—. In one specific variation of this embodiment, $R^4$ is methyl, $CH_3C(O)$— or phenyl-C(O)— and each $R^{11a}$, $R^{11b}$, $R^{12a}$, $R^{12b}$, $R^{13a}$, $R^{13b}$, $R^{14a}$ and $R^{14b}$ is H.

In one variation, the compound is of the formula (VII), having a structure of formula (VIIa):

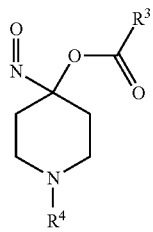

(VIIa)

where $R^3$ is unsubstituted or substituted alkyl, perhaloalkyl, unsubstituted or substituted alkenyl, unsubstituted or substituted alkynyl, unsubstituted or substituted aryl, unsubstituted or substituted heteroaryl or heterocyclyl; and $R^4$ is H, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted acyl, alkoxycarbonyl, substituted or unsubstituted heterocyclyl, substituted or unsubstituted aryl, substituted or unsubstituted aralkyl, or sulfonyl. In a specific such variation, $R^4$ is substituted or unsubstituted $C_1$-$C_8$ alkyl (e.g. methyl) or substituted or unsubstituted acyl (e.g. acetyl or benzoyl).

In another variation, the compound is of the formula (VII), having a structure of formula (VIIb):

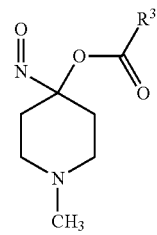

(VIIb)

where $R^3$ is unsubstituted or substituted alkyl, perhaloalkyl, unsubstituted or substituted alkenyl, unsubstituted or substituted alkynyl, unsubstituted or substituted aryl, unsubstituted or substituted heteroaryl or heterocyclyl.

In one embodiment, the invention embraces a compound of formula (III), (IV), (V), (Va), (VI) or (VII), where D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclyl-C(O)—. In another embodiment, the invention embraces a compound of formula (III), (IV), (V), (Va), (VI) or (VII), where D is $P(O)(OC_1$-$C_8alkyl)_2$. In one embodiment, the compound is of the formula (III), (IV), (V), (Va), (VI) or (VII), where D is selected from $P(O)(OCH_2CH_3)_2$ and $P(O)(OCH_2CH_2CH_3)_2$.

In one embodiment, the invention embraces a compound of the formula (III), (IV), (V), (Va), (VI) or (VII), where D is unsubstituted perhaloalkyl-C(O)—, substituted aryl-C(O)—, substituted aralkyl-C(O)—, or substituted $C_1$-$C_4$alkyl-C(O)— where the substitution is one or more substituents selected from the group consisting of halo, cyano, alkoxy, acyloxy, substituted acyloxy [e.g. $CH_3OCH_2CH_2OCH_2C(O)O$—], acylamino, substituted acylamino, alkylamino, substituted alkylamino, dialkylamino, N-acyl-substituted alkylamino [e.g. $(AcOCH_2)_2CHN$ (Ac)—], N-alkyl-substituted alkylamino [e.g. $(AcOCH_2)_2$ $CHN(Me)$-], alkoxycarbonylamino [e.g. t-BuOC(O)NH—], substituted alkoxycarbonylamino [e.g. $PhCH_2OC(O)$ NH—], alkoxycarbonyl, heterocyclyl and substituted heterocyclyl. In one variation, D is a di-substituted $C_1$-$C_4$alkyl-C(O)— where the $C_1$-$C_4$alkyl-C(O)— is of the formula

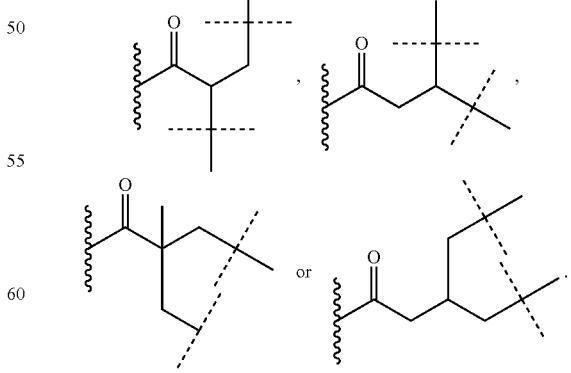

In another embodiment, the invention embraces a compound of formula (III), (IV), (V), (Va), (VI) or (VII), where D is a moiety of the formula:

In another embodiment, the compound is of the formula (III), (IV), (V), (Va), (VI) or (VII), where D is a moiety of the formula:

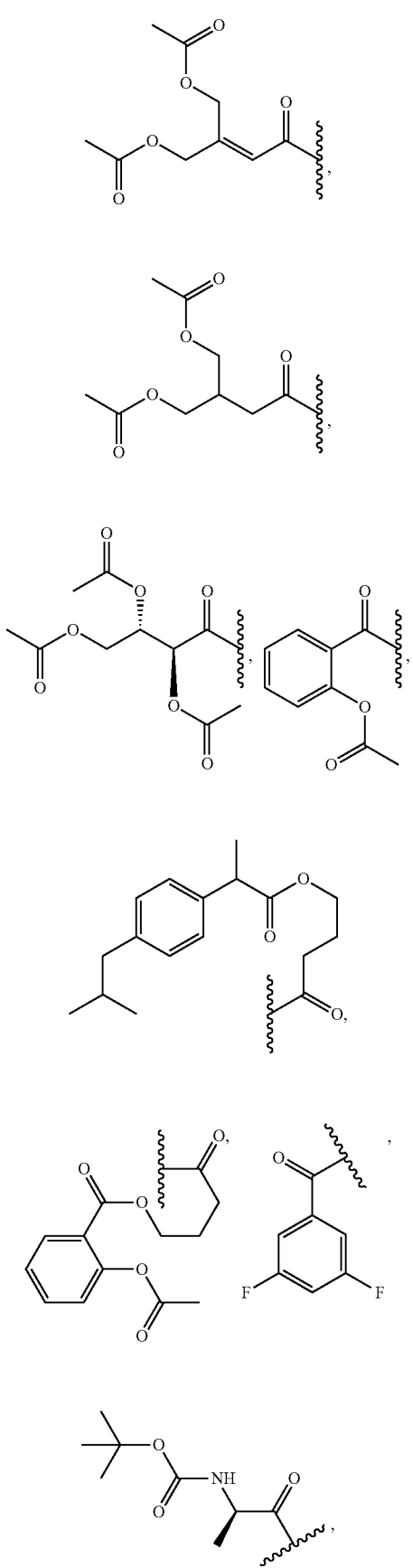
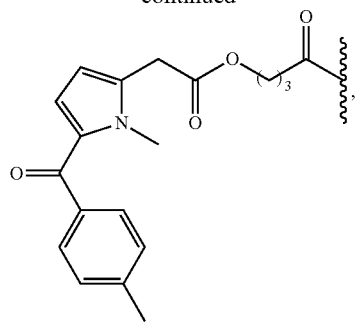
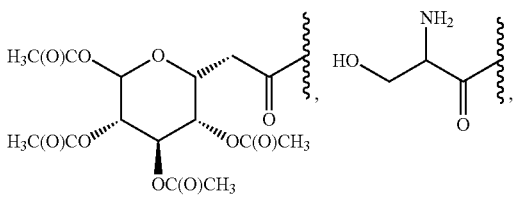
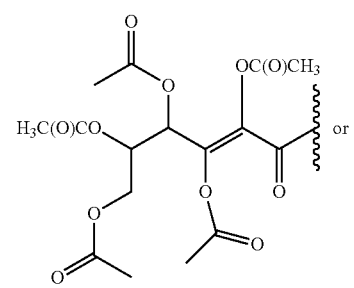
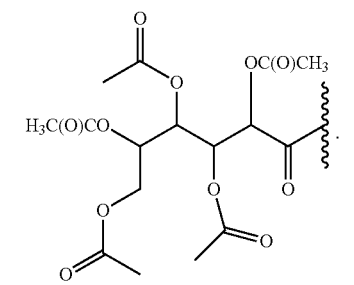

Compounds of formulae (VI) and (VII) have improved water solubility, chemical stability and ability to release HNO in vivo. Ring systems that include a heteroatom in the cyclic ring system result in improved aqueous solubility properties. Aqueous solubility of compounds described herein can be measured using methods known in the art.

For any of the compounds of the invention, such as the compounds of formula (I), (Ia), (II), (IIa), (III), (IV), (V), (Va), (VI) or (VII) or other compounds for use in the methods described herein, recitation or depiction of the parent compound intends and includes all salts and solvates thereof, where applicable. As such, all salts, such as pharmaceutically acceptable salts and solvates (e.g. hydrates) of a compound are embraced by the invention and described herein the same as if each and every salts or solvate were specifically and individually listed.

Representative compounds detailed herein and for use in the methods include, but are not limited to, the compounds listed in Table 1.

TABLE 1

Representative Compounds According to This Invention

| Compound No. | Name (Example) | Structure |
|---|---|---|
| 1 | 1-Methyl-4-nitrosopiperidin-4-yl acetate (Example 3) | 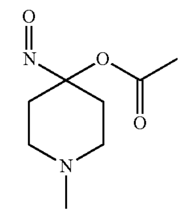 |
| 2 | 4-Nitrosotetrahydro-2H-pyran-4-yl acetate (Example 2) | 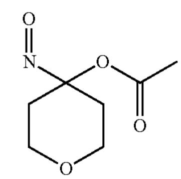 |
| 3 | 1-Acetyl-4-nitrosopiperidin-4-yl acetate (Example 4) | 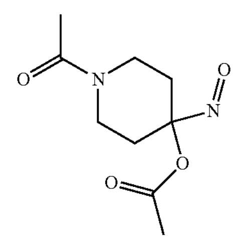 |
| 4 | 1,3-Diethoxy-2-nitrosopropan-2-yl acetate (Example 5) | 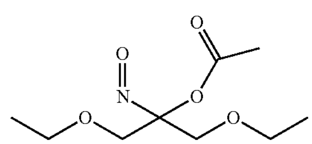 |
| 5 | 3-Nitrosotetrahydrothiophen-3-yl acetate (Example 6) | 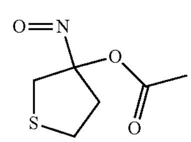 |
| 6 | 1-Benzoyl-4-nitrosopiperidin-4-yl acetate (Example 7) | 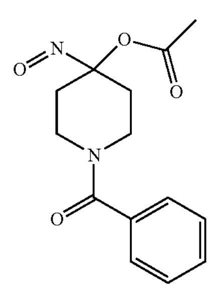 [SMILES: CC(=O)OC1(N=O)CCN(C(=O)c2ccccc2)CC1] |
| 7 | 1,2,2,6,6-Pentamethyl-4-nitrosopiperidin-4-yl acetate (Example 8) | 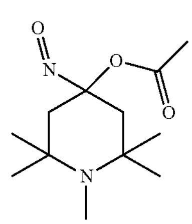 [SMILES: CC(=O)OC1(N=O)CC(C)(C)N(C)C(C)(C)C1] |

TABLE 1-continued

Representative Compounds According to This Invention

| Compound No. | Name (Example) | Structure |
|---|---|---|
| 8 | 2-Nitrosopropane-1,2,3-triyl triacetate (Example 9) | 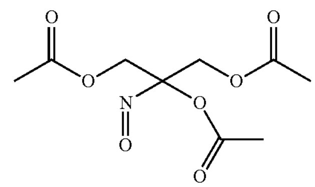 [SMILES: CC(=O)OCC(COC(C)=O)(N=O)OC(C)=O] |
| 9 | 1-Nitrosocyclohexyl 2,4-dichlorobenzoate (Example 11) | 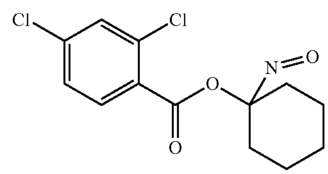 [SMILES: O=NC1(OC(=O)c2ccc(Cl)cc2Cl)CCCCC1] |
| 10 | 1-Nitrosocyclohexyl isobutyrate (Example 12) | 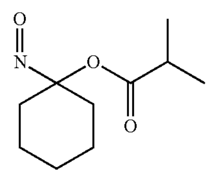 |
| 11 | 1-Methyl-4-nitrosopiperidin-4-yl isobutyrate (Example 13) | 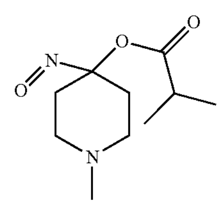 |
| 12 | 1-Methyl-4-nitrosopiperidin-4-yl 2,4-difluorobenzoate (Example 14A) | 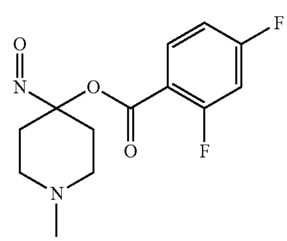 [SMILES: CN1CCC(N=O)(OC(=O)c2ccc(F)cc2F)CC1] |
| 13 | 1-Nitrosocyclohexyl 2-chloro-2,2-difluoroacetate (Example 15) | 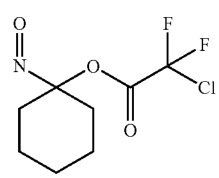 [SMILES: O=NC1(OC(=O)C(F)(F)Cl)CCCCC1] |
| 14 | 1-Nitrosocyclohexyl 4,4,4-trifluoro-3-methylbutanoate (Example 16) | 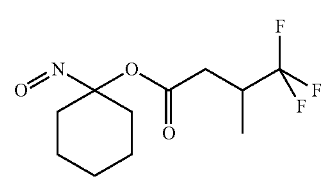 [SMILES: CC(CC(=O)OC1(N=O)CCCCC1)C(F)(F)F] |
| 15 | 4-Nitrosotetrahydro-2H-pyran-4-yl 2,2,2-trifluoroacetate (Example 17) | 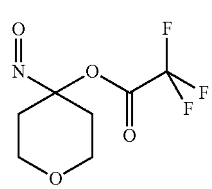 [SMILES: O=NC1(OC(=O)C(F)(F)F)CCOCC1] |

TABLE 1-continued

Representative Compounds According to This Invention

| Compound No. | Name (Example) | Structure |
|---|---|---|
| 16 | 4-Nitrosotetrahydro-2H-pyran-4-yl 3,3,3-trifluoropropanoate (Example 18) | 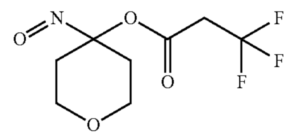 [SMILES: O=NC1(OC(=O)CC(F)(F)F)CCOCC1] |
| 17 | 4-Nitrosotetrahydro-2H-pyran-4-yl 4,4,4-trifluorobutanoate (Example 19) | 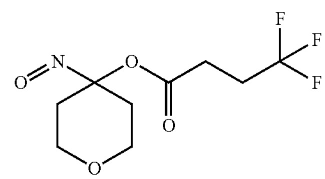 [SMILES: O=NC1(OC(=O)CCC(F)(F)F)CCOCC1] |
| 18 | 1-Nitrosocyclohexyl 2,2,3,3,3-pentafluoropropanoate (Example 20) | 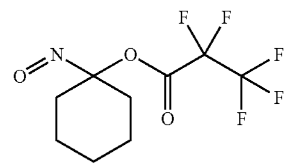 [SMILES: O=NC1(OC(=O)C(F)(F)C(F)(F)F)CCCCC1] |
| 19 | 1-Nitrosocyclohexyl 2-cyanoacetate (Example 21) | 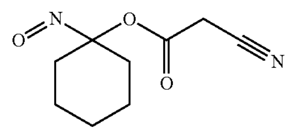 [SMILES: N#CCC(=O)OC1(N=O)CCCCC1] |
| 20 | 4-Nitrosotetrahydro-2H-pyran-4-yl 2,2,2-trichloroacetate (Example 22) | 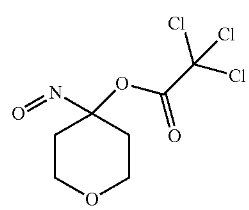 [SMILES: O=NC1(OC(=O)C(Cl)(Cl)Cl)CCOCC1] |
| 21 | 4-Nitrosotetrahydro-2H-pyran-4-yl 2,2,3,3,3-pentafluoropropanoate (Example 23) | 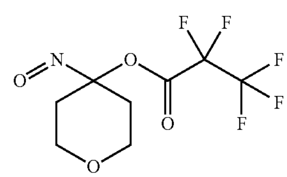 [SMILES: O=NC1(OC(=O)C(F)(F)C(F)(F)F)CCOCC1] |
| 22 | 4-Nitrosotetrahydro-2H-pyran-4-yl 2-chloro-2,2-difluoroacetate (Example 24) | 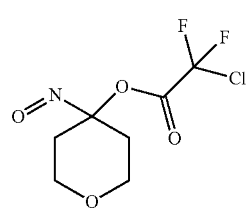 [SMILES: O=NC1(OC(=O)C(F)(F)Cl)CCOCC1] |
| 23 | (S)-4-Nitrosotetrahydro-2H-pyran-4-yl 2-acetamido-3-phenylpropanoate (Example 25) | 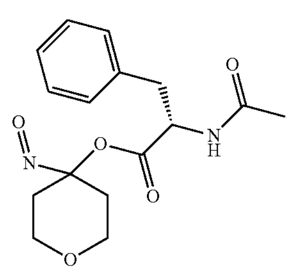 [SMILES: CC(=O)N[C@@H](Cc1ccccc1)C(=O)OC1(N=O)CCOCC1] |

TABLE 1-continued

Representative Compounds According to This Invention

| Compound No. | Name (Example) | Structure |
|---|---|---|
| 24 | 4-Nitrosotetrahydro-2H-pyran-4-yl pivalate (Example 26) | 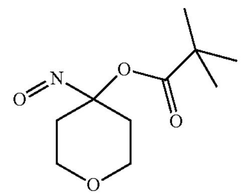 |
| 25 | Diethyl 1-nitrosocyclohexyl phosphate (Example 27) | 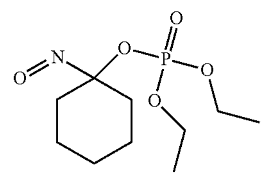 [SMILES: CCOP(=O)(OCC)OC1(N=O)CCCCC1] |
| 26 | Dibutyl 1-nitrosocyclohexyl phosphate (Example 28) | 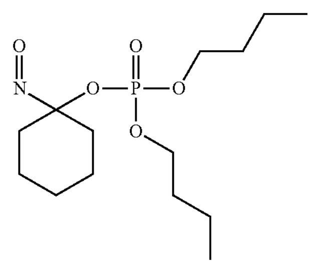 [SMILES: CCCCOP(=O)(OCCCC)OC1(N=O)CCCCC1] |
| 27 | Dibutyl 1-methyl-4-nitrosopiperidin-4-yl phosphate (Example 29) | 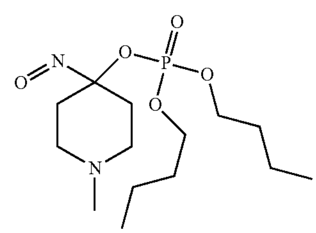 [SMILES: CCCCOP(=O)(OCCCC)OC1(N=O)CCN(C)CC1] |
| 28 | 1-Methyl-4-nitrosopiperidin-4-yl pivalate (Example 30) | 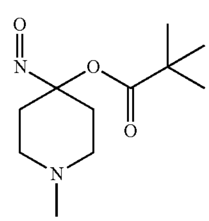 [SMILES: CN1CCC(N=O)(OC(=O)C(C)(C)C)CC1] |
| 29 | 1,2,2,6,6-Pentamethyl-4-nitrosopiperidin-4-yl pivalate (Example 31) | 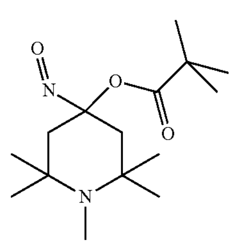 [SMILES: CN1C(C)(C)CC(N=O)(OC(=O)C(C)(C)C)CC1(C)C] |

TABLE 1-continued

Representative Compounds According to This Invention

| Compound No. | Name (Example) | Structure |
|---|---|---|
| 30 | 1-Benzoyl-4-nitrosopiperidin-4-yl 2,2,2-trifluoroacetate (Example 32) | 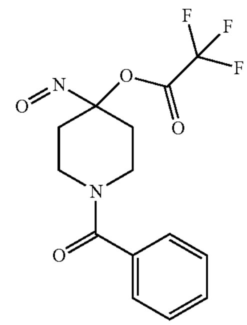 [SMILES: O=NC1(OC(=O)C(F)(F)F)CCN(C(=O)c2ccccc2)CC1] |
| 31 | 4-Nitrosotetrahydro-2H-pyran-4-yl 2-benzamidoacetate (Example 33) | 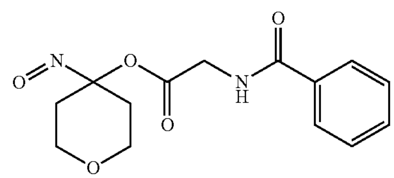 [SMILES: O=NC1(OC(=O)CNC(=O)c2ccccc2)CCOCC1] |
| 32 | 4-Nitrosotetrahydro-2H-pyran-4-yl 2-acetamidopropanoate (Example 34) | 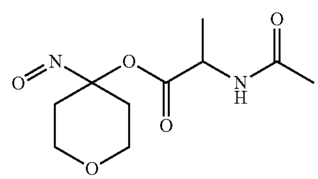 [SMILES: CC(=O)NC(C)C(=O)OC1(N=O)CCOCC1] |
| 33 | 4-Nitrosotetrahydro-2H-pyran-4-yl 3-(5-oxotetrahydrofuran-2-yl)propanoate (Example 35) | 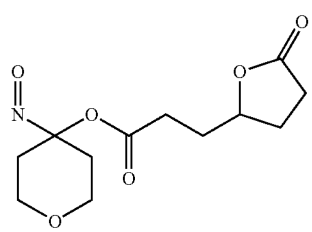 [SMILES: O=NC1(OC(=O)CCC2CCC(=O)O2)CCOCC1] |
| 34 | Methyl 4-nitrosotetrahydro-2H-pyran-4-yl succinate (Example 36) | 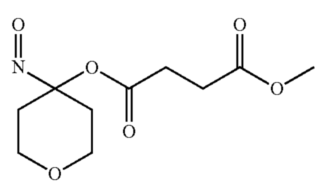 [SMILES: COC(=O)CCC(=O)OC1(N=O)CCOCC1] |
| 35 | 2-Methyl-2-((4-nitrosotetrahydro-2H-pyran-4-yloxy)carbonyl)propane-1,3-diyl diacetate (Example 37) | 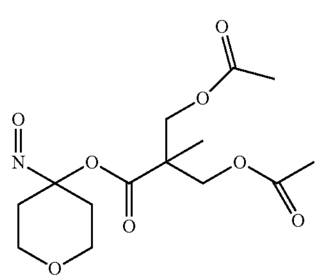 [SMILES: CC(=O)OCC(C)(COC(C)=O)C(=O)OC1(N=O)CCOCC1] |

TABLE 1-continued

Representative Compounds According to This Invention

| Compound No. | Name (Example) | Structure |
|---|---|---|
| 36 | 4-Nitrosotetrahydro-2H-pyran-4-yl 4-acetoxy-3-(acetoxymethyl)butanoate (Example 38) | 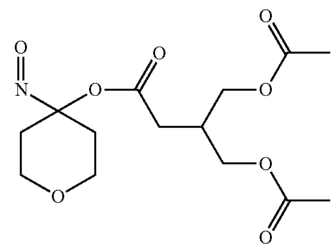 [SMILES: CC(=O)OCC(COC(C)=O)CC(=O)OC1(N=O)CCOCC1] |
| 37 | 1-Methyl 4-(4-nitrosotetrahydro-2H-pyran-4-yl) N-[(benzyloxy)carbonyl]aspartate (Example 39) | 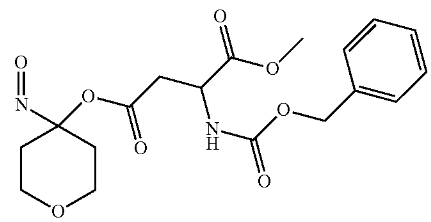 [SMILES: COC(=O)C(CC(=O)OC1(N=O)CCOCC1)NC(=O)OCc1ccccc1] |
| 38 | 1-tert-Butyl 4-(4-nitrosotetrahydro-2H-pyran-4-yl) N-(tert-butoxycarbonyl)aspartate (Example 40) | 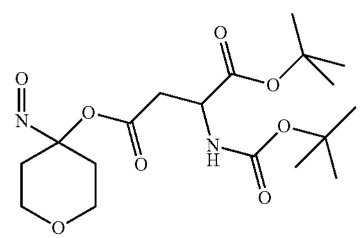 [SMILES: CC(C)(C)OC(=O)NC(CC(=O)OC1(N=O)CCOCC1)C(=O)OC(C)(C)C] |
| 39 | 8-Methyl-3-nitroso-8-azabicyclo[3.2.1]oct-3-yl acetate (Example 10) | 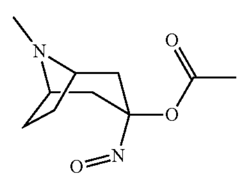 |
| 40 | 2-(Methyl(2-(4-nitrosotetrahydro-2H-pyran-4-yloxy)-2-oxoethyl)amino)propane-1,3-diyl diacetate (Example 49) | 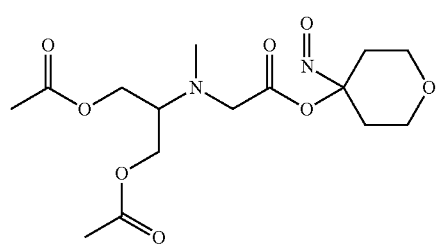 [SMILES: CC(=O)OCC(COC(C)=O)N(C)CC(=O)OC1(N=O)CCOCC1] |
| 41 | 2-(N-(2-(4-Nitrosotetrahydro-2H-pyran-4-yloxy)-2-oxoethyl)acetamido)propane-1,3-diyl diacetate (Example 50) | 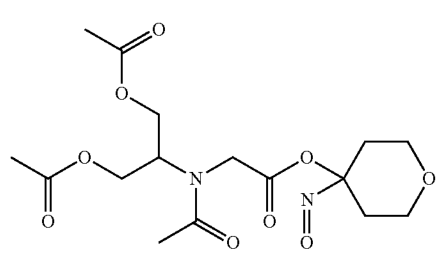 [SMILES: CC(=O)OCC(COC(C)=O)N(CC(=O)OC1(N=O)CCOCC1)C(C)=O] |

TABLE 1-continued

Representative Compounds According to This Invention

| Compound No. | Name (Example) | Structure |
|---|---|---|
| 42 | 2-(Acetoxymethyl)-4-(4-nitrosotetrahydro-2H-pyran-4-yloxy)-4-oxobutyl nicotinate (Example 51) | 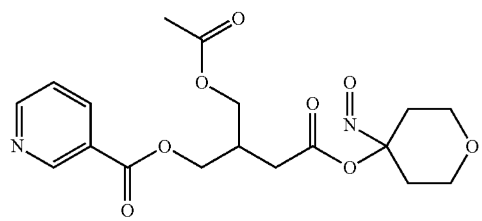 [SMILES: CC(=O)OCC(COC(=O)c1cccnc1)CC(=O)OC1(N=O)CCOCC1] |
| 43 | 2-(2-(4-Nitrosotetrahydro-2H-pyran-4-yloxy)-2-oxoethyl)propane-1,3-diyl dinicotinate (Example 51) | 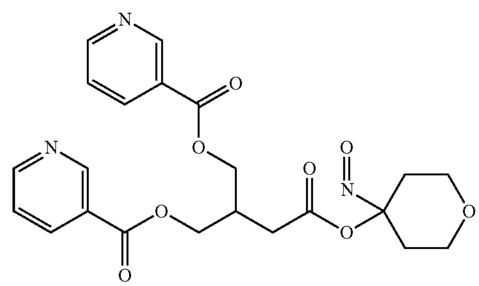 [SMILES: O=NC1(OC(=O)CC(COC(=O)c2cccnc2)COC(=O)c2cccnc2)CCOCC1] |
| 44 | 4-Nitrosotetrahydro-2H-pyran-4-yl 4-acetoxybutanoate (Example 41) | 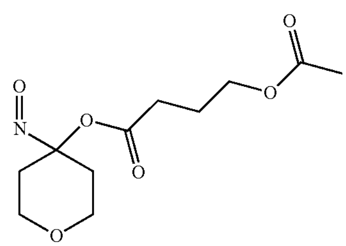 [SMILES: CC(=O)OCCCC(=O)OC1(N=O)CCOCC1] |
| 45 | 2-((2-(2-Methoxyethoxy)acetoxy)methyl)-4-(4-nitrosotetrahydro-2H-pyran-4-yloxy)-4-oxobutyl nicotinate (Example 51) | 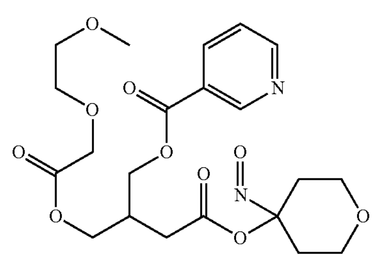 [SMILES: COCCOCC(=O)OCC(COC(=O)c1cccnc1)CC(=O)OC1(N=O)CCOCC1] |
| 46 | 4-Nitrosotetrahydro-2H-pyran-4-yl 4-({2-[4-(2-methylpropyl)phenyl]propanoyl}oxy)butanoate (Example 47) | 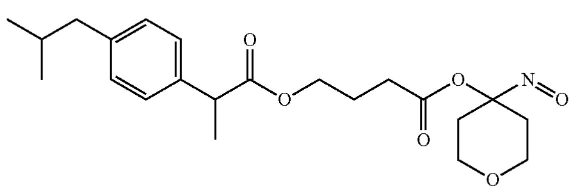 [SMILES: CC(C)Cc1ccc(C(C)C(=O)OCCCC(=O)OC2(N=O)CCOCC2)cc1] |
| 47 | 4-Nitrosooxan-4-yl (2R)-2-{[(tert-butoxy)carbonyl]amino}propanoate (Example 48) | 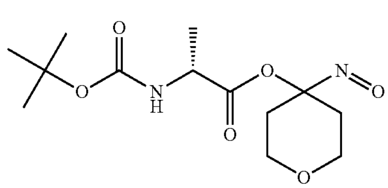 [SMILES: C[C@@H](NC(=O)OC(C)(C)C)C(=O)OC1(N=O)CCOCC1] |

TABLE 1-continued

Representative Compounds According to This Invention

| Compound No. | Name (Example) | Structure |
|---|---|---|
| 48 | 4-Nitrosotetrahydro-2H-pyran-4-yl 4-(acetyloxy)-3-[(acetyloxy)methyl]but-2-enoate (Example 42) | 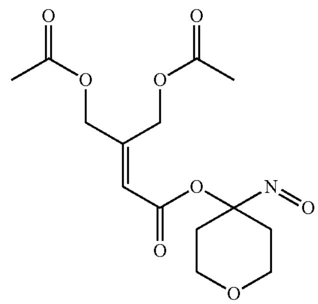 [SMILES: CC(=O)OCC(=CC(=O)OC1(N=O)CCOCC1)COC(C)=O] |
| 49 | 1-Methyl-4-nitrosopiperidin-4-yl 4-(acetyloxy)-3-[(acetyloxy)methyl]butanoate (Example 43) | 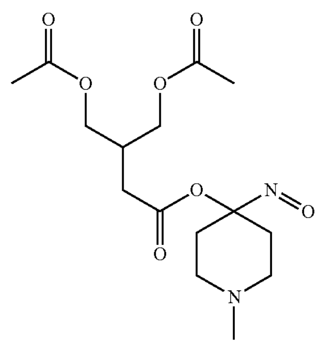 [SMILES: CC(=O)OCC(COC(C)=O)CC(=O)OC1(N=O)CCN(C)CC1] |
| 50 | 4-Nitrosotetrahydro-2H-pyran-4-yl (2S,3S)-2,3,4-tris(acetyloxy)butanoate (Example 44) | 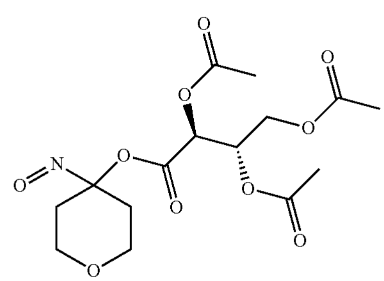 [SMILES: CC(=O)OC[C@H](OC(C)=O)[C@H](OC(C)=O)C(=O)OC1(N=O)CCOCC1] |
| 51 | 4-Nitrosotetrahydro-2H-pyran-4-yl 2-(acetyloxy)benzoate (Example 45) | 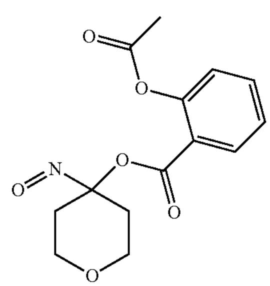 [SMILES: CC(=O)Oc1ccccc1C(=O)OC1(N=O)CCOCC1] |
| 52 | 4-[(4-Nitrosotetrahydro-2H-pyran-4-yl)oxy]-4-oxobutyl 2-(acetyloxy)benzoate (Example 46) | 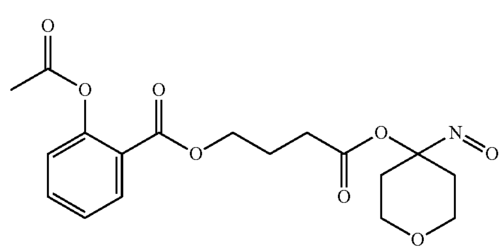 [SMILES: CC(=O)Oc1ccccc1C(=O)OCCCC(=O)OC1(N=O)CCOCC1] |

TABLE 1-continued

Representative Compounds According to This Invention

| Compound No. | Name (Example) | Structure |
|---|---|---|
| 53 | 1-Methyl-4-nitrosopiperidin-4-yl 3,5-difluorobenzoate (Example 14B) | 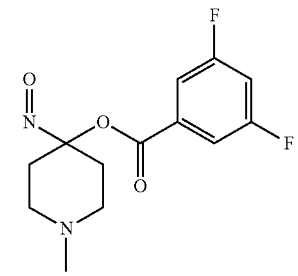 [SMILES: CN1CCC(N=O)(OC(=O)c2cc(F)cc(F)c2)CC1] |
| 54 | 4-nitrosooxan-4-yl 4-[(2-{1-methyl-5-[(4-methylphenyl)carbonyl]-1H-pyrrol-2-yl}acetyl)oxy]butanoate (Example 51) | 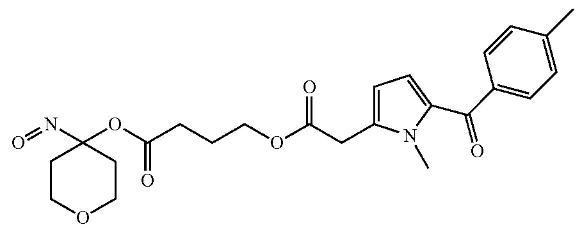 [SMILES: Cc1ccc(C(=O)c2ccc(CC(=O)OCCCC(=O)OC3(N=O)CCOCC3)n2C)cc1] |
| 55 | 4-nitrosooxan-4-yl 2-[(2R,3S,4R,5S)-3,4,5,6-tetrakis(acetyloxy)oxan-2-yl]acetate (Example 51) | 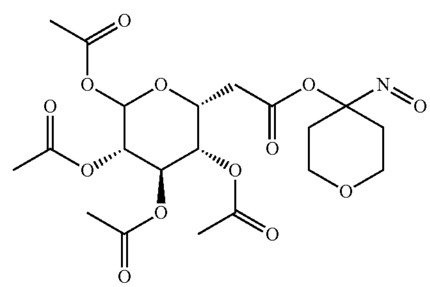 [SMILES: CC(=O)OC1O[C@H](CC(=O)OC2(N=O)CCOCC2)[C@H](OC(C)=O)[C@@H](OC(C)=O)[C@@H]1OC(C)=O] |
| 56 | 4-nitrosooxan-4-yl 2-amino-3-hydroxypropanoate (Example 51) | 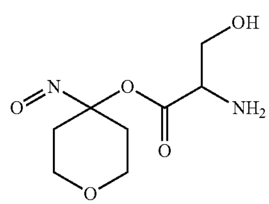 [SMILES: NC(CO)C(=O)OC1(N=O)CCOCC1] |
| 57 | 4-nitrosooxan-4-yl (2E)-2,3,4,5,6-pentakis(acetyloxy)hex-2-enoate (Example 51) | 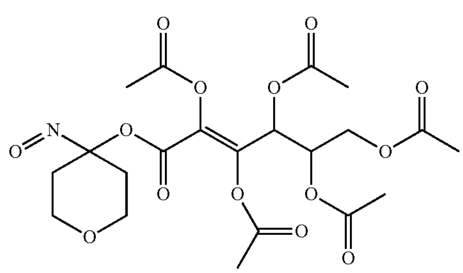 [SMILES: CC(=O)OCC(OC(C)=O)C(OC(C)=O)/C(OC(C)=O)=C(\OC(C)=O)C(=O)OC1(N=O)CCOCC1] |
| 58 | 4-nitrosooxan-4-yl 2,3,4,5,6-pentakis(acetyloxy)hexanoate (Example 51) | 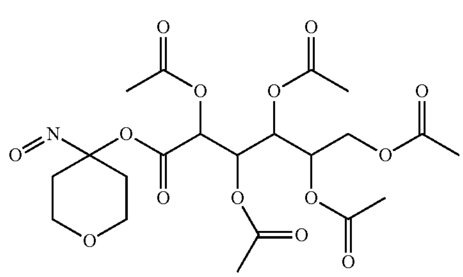 [SMILES: CC(=O)OCC(OC(C)=O)C(OC(C)=O)C(OC(C)=O)C(OC(C)=O)C(=O)OC1(N=O)CCOCC1] |

Compounds for Use in the Methods

The methods described may employ a nitroxyl donor compound described herein. The methods may employ any compounds detailed herein, such as compounds described in the Brief Summary of the Invention and elsewhere. For example, the methods described may employ a nitroxyl donor compound of formula (I). In one variation, the method employs a nitroxyl donor of the formula (I), including any one or more of: 1-nitrosocycloheptyl acetate, 1-nitrosocycloheptyl benzoate, 9-nitrosobicyclo[3.3.1]nonan-9-yl acetate, 8-methyl-3-nitroso-8-azabicyclo[3.2.1]octan-3-yl acetate, and compounds where: (i) $R^1$ and $R^2$ are taken together to form a substituted 6-membered carbocyclic moiety where the substituted 6-membered carbocyclic moiety is a monocyclic or bicyclic ring that is substituted with a moiety selected from the group consisting of alkyl, nitroso, acyl, oxime, and substituted alkenyl; or (ii) $R^1$ and $R^2$ are taken together to form an unsubstituted or substituted 5 or 6-membered heterocyclic moiety where the 5 or 6-membered heterocyclic moiety is dioxane or acyloxy-substituted tetrahydropyan. In addition, the invention embraces pharmaceutical compositions comprising a pharmaceutically acceptable carrier and any compound detailed herein, such as a nitroxyl donor compound of formula (I), which may include 1-nitrosocycloheptyl acetate, 1-nitrosocycloheptyl benzoate, 9-nitrosobicyclo[3.3.1]nonan-9-yl acetate, 8-methyl-3-nitroso-8-azabicyclo[3.2.1]octan-3-yl acetate, and compounds where (i) $R^1$ and $R^2$ are taken together to form a substituted 6-membered carbocyclic moiety, where the substituted 6-membered carbocyclic moiety is a monocyclic or bicyclic ring that is substituted with a moiety selected from the group consisting of alkyl, nitroso, acyl, oxime, and substituted alkenyl; or (ii) $R^1$ and $R^2$ are taken together to form an unsubstituted or substituted 5 or 6-membered heterocyclic moiety, where the 5 or 6-membered heterocyclic moiety is dioxane or acyloxy-substituted tetrahydropyan.

Methods described for treating ischemia/reperfusion injury or cancer may employ a nitroxyl donor compound of formula (I)-(VII), including 1-nitrosocycloheptyl acetate, 1-nitrosocycloheptyl benzoate, 9-nitrosobicyclo[3.3.1] nonan-9-yl acetate or 8-methyl-3-nitro so-8-azabicyclo [3.2.1]octan-3-yl acetate; and compounds where (i) $R^1$ or $R^2$ is an unsubstituted $C_1$-$C_8$ alkyl, e.g. methyl or propyl, and D is an NSAID moiety; (ii) $R^1$ and $R^2$ are taken together to form an unsubstituted 6-membered carbocyclic moiety and D is n-alkyl-C(O)—, $ClCH_2$—C(O)—, $CCl_3$—C(O)—, $CF_3$—C(O)—, $(CH_3)_3C$—C(O)—, alkenyl-C(O)—, substituted alkenyl-C(O)—, unsubstituted aryl-C(O)—, monosubstituted aryl-C(O)— or an NSAID moiety; (iii) $R^1$ and $R^2$ are taken together to form a substituted 6-membered carbocyclic moiety, where the substituted 6-membered carbocyclic moiety is a monocyclic or bicyclic ring that is substituted with a moiety selected from the group consisting of alkyl, nitroso, acyl, oxime, and substituted alkenyl; or (iv) $R^1$ and $R^2$ are taken together to form an unsubstituted or substituted 5 or 6-membered heterocyclic moiety, where the 5 or 6-membered heterocyclic moiety is dioxane or acyloxy-substituted tetrahydropyan.

For all compounds disclosed herein, where applicable due to the presence of a stereocenter, the compound is intended to embrace all possible stereoisomers of the compound depicted or described. Compositions comprising a compound with at least one stereocenter are also embraced by the invention, and include racemic mixtures or mixtures containing an enantiomeric excess of one enantiomer or single diastereomers or diastereomeric mixtures. All such isomeric forms of these compounds are expressly included herein the same as if each and every isomeric form were specifically and individually listed. The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are also expressly included in the present invention. The compounds herein may also be represented in multiple tautomeric forms, in such instances, the invention expressly includes all tautomeric forms of the compounds described herein, even though only a single tautomeric form may be represented.

In one variation, the invention provides for a composition of substantially pure compound. "Substantially pure" intends a preparation of the compound that contains no more than 25% of impurity (e.g. by weight %), which impurity may be another compound altogether or a different form of the compound (e.g. a different salt or isomer). Percent purity may be assessed by methods known in the art. In one variation, a preparation of substantially pure compound is provided where the preparation contains no more than 15% of impurity. In another variation, a preparation of substantially pure compound is provided where the preparation contains no more than 10% impurity. In another variation, a preparation of substantially pure compound is provided where the preparation contains no more than 5% impurity. In another variation, a preparation of substantially pure compound is provided where the preparation contains no more than 3% impurity. In another variation, a preparation of substantially pure compound is provided where the preparation contains no more than 1% impurity.

Preferably, compounds of this invention are provided in purified and isolated forms, for example following column chromatography, high-pressure liquid chromatography, recrystallization, or other purification techniques. Where particular stereoisomers of compounds of this invention are denoted, such stereoisomers preferably are substantially free of other stereoisomers.

General Synthetic Methods

The compounds of this invention may be prepared by a number of processes as generally described below and more specifically in the Examples hereinafter.

The following abbreviations are used herein: dichloromethane (DCM); dimethylsulfoxide (DMSO).

Unless specifically described, starting materials for the reactions are either commercially available or may be prepare by known procedures. For example, many of the starting materials are available from commercial suppliers such as Sigma-Aldrich. Others may be prepared by procedures described in standard reference texts such as March's Advanced Organic Chemistry, (John Wiley and Sons) and Larock's Comprehensive Organic Transformations (VCH Publishers Inc.).

A method of synthesizing an oxime intermediate used in the synthesis of compounds of the invention is shown in General Method 1.

General Method 1

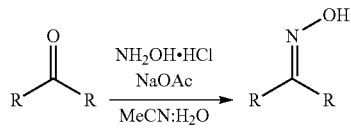

To a solution of hydroxylamine hydrochloride in acetonitrile:water (2:1 v/v) at ambient temperature is added sodium acetate and a ketone with stirring. After about 3 hours or at reaction completion which may be assessed by known method, the solvents are removed in vacuo and the reaction quenched with potassium carbonate solution. The organics are extracted into DCM, combined, dried over Na$_2$SO$_4$ and concentrated in vacuo to afford the oxime without need for further purification.

General Method 1A

To a stirred solution of hydroxylamine hydrochloride (1.1 equiv.) in acetonitrile:water (2:1 v/v) at ambient temperature is added sodium acetate (1.1 equiv.) and a ketone (1 equiv.). The reaction progress is monitored by TLC and LC-MS and on completion the solvents are removed in vacuo and the reaction quenched with potassium carbonate solution. The organics are extracted into DCM, combined, dried over Na$_2$SO$_4$ and concentrated in vacuo to afford the oxime without need for further purification.

A method of synthesizing a compound of the invention from an oxime intermediate is descried in General Methods 2-4.

General Method 2

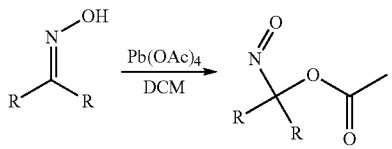

A solution of an oxime in DCM is added dropwise to a solution of lead tetraacetate in DCM at 0° C. A blue colour gradually appears on addition of the oxime solution. Upon complete addition (about 1 hour) the reaction is allowed to warm to ambient temperature and stirring is continued for a further 2-3 hours or until reaction completion. The reaction is quenched by the addition of water, the phases separated and the organics dried over Na$_2$SO$_4$ and concentrated in vacuo to afford the acetoxy-1-nitroso compound which may be purified, e.g. by column chromatography on silica gel with pentane/ether (depending on nature of the oxime) as the eluent to afford the product as a blue oil.

General Method 2A

To a solution of lead tetraacetate (1 equiv.) in DCM (5 vol) at 0° C. is added a solution of the oxime (1 equiv.) in DCM (5 vol) dropwise. A blue color gradually appears on addition of the oxime solution. Upon complete addition (about 1 hour) the reaction is allowed to warm to ambient temperature and stirring continued for a further 2-3 hours or until reaction completion (monitored by TLC and HPLC). The reaction is quenched by the addition of water, the phases separated and the organics dried over Na$_2$SO$_4$ and concentrated in vacuo to afford the acetoxy-1-nitroso compound which is purified, by silica column chromatography using appropriate solvent mixtures as the eluent to afford the product.

General Method 3

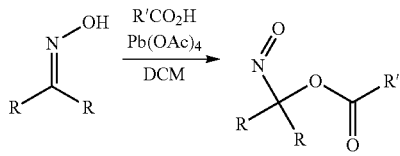

A solution of an oxime in DCM is added dropwise to a solution of lead tetraacetate and an acid in DCM at 0° C. A blue colour gradually appears on addition of the oxime solution. Upon complete addition (about 1 hour) the reaction is allowed to warm to ambient temperature and stirring is continued for a further 2-3 hours or until reaction completion. The reaction is quenched by the addition of water, the phases separated and the organics dried over Na$_2$SO$_4$ and concentrated in vacuo to afford the crude nitroso compound, which is purified, e.g. by column chromatography on silica gel with pentane/ether as the eluent to afford the purified compound as a blue oil.

General Method 3A

To a solution of lead tetraacetate (1 equiv.) and an acid (10 equiv.) in DCM (7 vol) at 0° C. is added a solution of an oxime (1 equiv.) in DCM (3 vol) dropwise. A blue color gradually appears on addition of the oxime solution. Upon complete addition (about 1 hour) the reaction is allowed to warm to ambient temperature and stirring is continued for a further 2-3 hours or until reaction completion (monitored by TLC and HPLC). The reaction is quenched by the addition of water, the phases separated and the organics dried over Na$_2$SO$_4$ and concentrated in vacuo to afford the crude acyloxy-1-nitroso compound, which is purified by silica column chromatography using appropriate solvent mixtures as the eluent to afford the product.

General Method 4

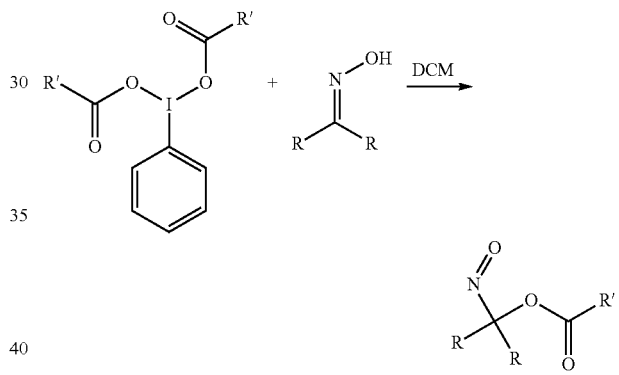

To a solution of bis(acyloxy)iodobenzene (which may be synthesized according to the method described in Org. Lett. 2004, 3613-3615) in DCM cooled to 0° C. is added a solution of an oxime in DCM. After about 2 hours or until reaction completion, the reaction mixture is concentrated in vacuo and purified, e.g. by column chromatography on silica gel with DCM as the eluent to afford the purified compound as a blue oil.

General Method 4A

To a solution of bis(acyloxy)iodobenzene (1 equiv.) (synthesized according to the method described in Org. Lett. 2004, 3613-3615) in DCM (10 vol) cooled to 0° C. is added a solution of an oxime (1 equiv.) in DCM (1 vol). The reaction progress is monitored by TLC and LC-MS and on completion the reaction mixture is concentrated in vacuo and purified, by silica column chromatography using appropriate solvent mixtures as the eluent to afford the product.

Methods of Using the Compounds and Compositions

The compounds and compositions herein may be used to treat and/or prevent the onset and/or development of a disease or condition that is responsive to nitroxyl therapy.

The invention embraces methods of administering to an individual (including an individual identified as in need of such treatment) an effective amount of a compound to produce a desired effect. Identifying a subject in need of such treatment can be in the judgment of a physician, clinical staff, emergency response personnel or other health care professional and can be subjective (e.g. opinion) or objective (e.g. measurable by a test or diagnostic method).

One embodiment provides a method of modulating (including increasing) in vivo nitroxyl levels in an individual in need thereof, the method comprising administering to the individual a compound that donates nitroxyl under physiological conditions or a pharmaceutically acceptable salt thereof. An individual is in need of nitroxyl modulation if they have or are suspected of having or are at risk of having or developing a disease or condition that is responsive to nitroxyl therapy.

Particular diseases or conditions embraced by the methods of the invention include cardiovascular diseases such as heart failure or conditions and diseases or conditions that implicate or may implicate ischemia/reperfusion injury and cancer, e.g. breast, pancreatic, prostate, and colorectal cancer. These methods are described in more detail below.

Compositions comprising a nitroxyl-donating compound of the invention are embraced by the invention. However, the methods described may use more than one nitroxyl donating compound; for example, the methods may employ Angeli's salt and a nitroxyl donor compound of the present invention or two or more nitroxyl donor compounds of the present invention, which may be administered together or sequentially.

Cardiovascular Diseases

Provided herein are methods of treating cardiovascular diseases such as heart failure by administering an effective amount of at least one nitroxyl donor compound to an individual in need thereof. The methods provide for treating a cardiovascular disease, such as heart failure, in an individual in need thereof by administering to the individual a compound according to any formulae detailed herein or a pharmaceutically acceptable salt thereof. Also provided are methods of administering a therapeutically effective dose of at least one nitroxyl donating compound in combination with at least one other positive inotropic agent to an individual in need thereof. Further provided are methods of administering a therapeutically effective amount of at least one nitroxyl donating compound to an individual who is receiving beta-antagonist therapy and who is experiencing heart failure. Methods are provided herein for administering compounds of the invention in combination with beta-adrenergic agonists to treat heart failure. Such agonists include dopamine, dobutamine, and isoproterenol, and analogs and derivatives of such compounds. Also provided are methods of administering nitroxyl donors to individuals receiving treatment with beta-antagonizing agents such as propranolol, metoprolol, bisoprolol, bucindolol, and carvedilol. Further, methods are provided herein for treating specific classifications of heart failure, such as Class III heart failure and acute heart failure.

Also embraced by the invention is a method of treating congestive heart failure (CHF), including acute congestive heart failure, by administering an effective amount at least one nitroxyl donating compound to an individual in need thereof, which individual may be experiencing heart failure. Also disclosed is a method of treating CHF by administering an effective amount of at least one nitroxyl donating compound in combination with an effective amount of at least one other positive inotropic agent to an individual in need thereof, which individual may be experiencing heart failure. In one variation, the other positive inotrope is a beta-adrenergic agonist, such as dobutamine. The combined administration of a nitroxyl donor and at least one other positive inotropic agent comprises administering the nitroxyl donor either sequentially with the other positive inotropic agent for example, the treatment with one agent first and then the second agent, or administering both agents at substantially the same time, wherein there is an overlap in performing the administration. With sequential administration, an individual is exposed to the agents at different times, so long as some amount of the first agent, which is sufficient to be therapeutically effective in combination with the second agent, remains in the subject when the other agent is administered. Treatment with both agents at the same time can involve administration of the agents in the same dose, such as a physically mixed dose, or in separate doses administered at the same time.

In particular an embodiment, a nitroxyl donor is administered to an individual experiencing heart failure that is receiving beta-antagonist therapy. A beta-antagonist (also known as a beta-blocker) includes any compound that effectively acts as an antagonist at a subject's beta-adrenergic receptors, and provides desired therapeutic or pharmaceutical results, such as diminished vascular tone and/or heart rate. A subject who is receiving beta-antagonist therapy is any subject to whom a beta-antagonist has been administered, and in whom the beta-antagonist continues to act as an antagonist at the subject's beta-adrenergic receptors. In particular embodiments a determination of whether a subject is receiving beta-blocking therapy is made by examination of the subject's medical history. In other embodiments the subject is screened for the presence of beta-blocking agents by chemical tests, such as high-speed liquid chromatography as described in Thevis et al., *Biomed. Chromatogr.*, 15:393-402 (2001).

The administration of a nitroxyl donating compound either alone, in combination with a positive inotropic agent, or to a subject receiving beta-antagonist therapy, is used to treat heart failure of all classifications. In particular embodiments a nitroxyl donating compound is used to treat early-stage chronic heart failure, such as Class II heart failure. In other embodiments a nitroxyl donating compound is used in combination with a positive inotropic agent, such as isoproterenol to treat Class IV heart failure. In still other embodiments a nitroxyl donating compound is used in combination with another positive inotropic agent, such as isoproterenol to treat acute heart failure. In some embodiments, when a nitroxyl donor is used to treat early stage heart failure, the dose administered is lower than that used to treat acute heart failure. In other embodiments the dose is the same as is used to treat acute heart failure.

Also provided are methods of treating cardiovascular diseases or conditions that are responsive to nitroxyl therapy, including coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, including but not limited to congestive heart failure such as acute congestive heart failure and acute decompensated heart failure. Methods of treating other cardiovascular diseases or conditions are also provided, such as methods of treating pulmonary hypertension or cardiac hypertrophy. The methods employ a nitroxyl donating compound alone or in combination with another positive inotropic agent, which may in one aspect be another nitroxyl donating compound.

Ischemia/Reperfusion Injury

The invention embraces methods of treating or preventing or protecting against ischemia/reperfusion injury. In particular, compounds of the invention are beneficial for individuals at risk for an ischemic event. Thus, provided herein is a method of preventing or reducing the injury associated with ischemia/reperfusion by administering an effective amount of at least one nitroxyl donating compound to an individual, preferably prior to the onset of ischemia. The methods provide for treating ischemia/reperfusion injury in an individual in need thereof by administering to the individual a compound according to any formulae detailed herein or a pharmaceutically acceptable salt thereof. A compound of the invention may be administered to an individual after ischemia but before reperfusion. A compound of the invention may also be administered after ischemia/reperfusion, but where the administration protects against further injury. Also provided is a method in which the individual is demonstrated to be at risk for an ischemic event. Also disclosed is a method of administering a nitroxyl donating compound to an organ that is to be transplanted in an amount effective to reduce ischemia/reperfusion injury to the tissues of the organ upon reperfusion in the recipient of the transplanted organ.

Nitroxyl donors of the invention may thus be used in methods of preventing or reducing injury associated with future ischemia/reperfusion. For example, administration of a nitroxyl donor prior to the onset of ischemia may reduce tissue necrosis (the size of infarct) in at-risk tissues. In live subjects this may be accomplished by administering an effective amount of a nitroxyl donating compound to an individual prior to the onset of ischemia. In organs to be transplanted this is accomplished by contacting the organ with a nitroxyl donor prior to reperfusion of the organ in the transplant recipient. Compositions comprising more than one nitroxyl-donating compound also could be used in the methods described, for example, Angeli's salt and a nitroso derivative of the present invention or two or more nitroso derivatives of the present invention. The nitroxyl-donating compound also can be used in combination with other classes of therapeutic agents that are designed to minimize ischemic injury, such as beta blockers, calcium channel blockers, anti-platelet therapy or other interventions for protecting the myocardium in individuals with coronary artery disease.

One method of administering a nitroxyl donor to live subjects includes administration of the nitroxyl-donating compound prior to the onset of ischemia. This refers only to the onset of each instance of ischemia and would not preclude performance of the method with subjects who have had prior ischemic events, i.e., the method also contemplates administration of nitroxyl-donating compounds to a subject who has had an ischemic event in the past.

Individuals can be selected who are at risk of a first or subsequent ischemic event. Examples include individuals with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia such as a cerebrovascular accident CVA). In particular examples of the methods, individuals are selected for treatment who are at risk of future ischemia, but who have no present evidence of ischemia (such as electrocardiographic changes associated with ischemia (for example, peaked or inverted T-waves or ST segment elevations or depression in an appropriate clinical context), elevated CKMB, or clinical evidence of ischemia such as crushing sub-sternal chest pain or arm pain, shortness of breath and/or diaphoresis). The nitroxyl-donating compound also could be administered prior to procedures in which myocardial ischemia may occur, for example an angioplasty or surgery (such as a coronary artery bypass graft surgery). Also embraced is a method of administering a nitroxyl-donating compound to an individual at demonstrated risk for an ischemic event. The selection of an individual with such a status could be performed by a variety of methods, some of which are noted above. For example, an individual with one of more of an abnormal EKG not associated with active ischemia, prior history of myocardial infarction, elevated serum cholesterol, etc., would be at risk for an ischemic event. Thus, an at-risk individual could be selected by physical testing or eliciting the potential subject's medical history to determine whether the subject has any indications of risk for an ischemic event. If risk is demonstrated based on the indications discussed above, or any other indications that one skilled in the art would appreciate, then the individual would be considered at demonstrated risk for an ischemic event.

Ischemia/reperfusion may damage tissues other than those of the myocardium and the invention embraces methods of treating or preventing such damage. In one variation, the method finds use in reducing injury from ischemia/reperfusion in the tissue of the brain, liver, gut, kidney, bowel, or in any other tissue. The methods preferably involve administration of a nitroxyl donor to an individual at risk for such injury. Selecting a person at risk for non-myocardial ischemia could include a determination of the indicators used to assess risk for myocardial ischemia. However, other factors may indicate a risk for ischemia/reperfusion in other tissues. For example, surgery patients often experience surgery related ischemia. Thus, individuals scheduled for surgery could be considered at risk for an ischemic event. The following risk factors for stroke (or a subset of these risk factors) would demonstrate a subject's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Ingall, "Preventing ischemic stroke: current approaches to primary and secondary prevention," *Postgrad. Med.*, 107(6):34-50 (2000). Further, complications of untreated infectious diarrhea in the elderly can include myocardial, renal, cerebrovascular and intestinal ischemia. Slotwiner-Nie & Brandt, "Infectious diarrhea in the elderly," *Gastroenterol. Clin. N. Am.*, 30(3): 625-635 (2001). Alternatively, individuals could be selected based on risk factors for ischemic bowel, kidney or liver disease. For example, treatment would be initiated in elderly subjects at risk of hypotensive episodes (such as surgical blood loss). Thus, subjects presenting with such an indication would be considered at risk for an ischemic event. Also embraced is a method of administering a nitroxyl donating compound of the invention to an individual who has any one or more of the conditions listed herein, such as diabetes mellitus or hypertension. Other conditions that may result in ischemia such as cerebral arteriovenous malformation would be considered to demonstrate risk for an ischemic event.

The method of administering nitroxyl to organs to be transplanted includes administration of nitroxyl prior to removal of the organ from the donor, for example through the perfusion cannulas used in the organ removal process. If the organ donor is a live donor, for example a kidney donor, the nitroxyl donor can be administered to the organ donor as described above for a subject at risk for an ischemic event. In other cases the nitroxyl donor can be administered by storing the organ in a solution comprising the nitroxyl donor. For example, the nitroxyl donor can be included in the organ preservation solution, such as University of Wisconsin "UW" solution, which is a solution comprising hydroxyethyl starch substantially free of ethylene glycol, ethylene chlorohydrin and acetone (see U.S. Pat. No. 4,798,824).

Cancer

The invention embraces methods of treating cancer by administering an effective amount of at least one nitroxyl donor compound to an individual having or who is suspected of having a cancerous disease, e.g. cancer. The invention also provides methods of treating cancer by administering a therapeutically effective dose of at least one nitroxyl donor compound in combination with at least another anti-cancer agent to an individual having cancer. The methods provide for treating cancer in an individual in need thereof by administering to the individual a compound according to any formulae detailed herein or a pharmaceutically acceptable salt thereof Cancers that may be treated by the method of this invention include: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomyosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. The method of treating such diseases comprises administering a therapeutically effective amount of a compound of this to a subject. The method may be repeated as necessary.

Compounds of this invention can be administered in combination with other anti-cancer or cytotoxic agents, including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include .beta.-lapachone, ansamitocin P3, auristatin, bicalutamide, bleomycin, bleomycin, bortezomib, busulfan, calicheamycin, callistatin A, camptothecin, capecitabine, cisplatin, cryptophycins, daunorubicin, docetaxel, doxorubicin, duocarmycin, dynemycin A, etoposide, floxuridine, floxuridine, fludarabine, fluoruracil, gefitinib, gemcitabine, hydroxyurea, imatinib, interferons, interleukins, irinotecan, methotrexate, mitomycin C, oxaliplatin, paclitaxel, spongistatins, suberoylanilide hydroxamic acid (SAHA), thiotepa, topotecan, trichostatin A, vinblastine, vincristine and vindesine.

Pharmaceutical Composition, Dosage Forms and Treatment Regimens

Also included are pharmaceutically acceptable compositions comprising a compound of the invention or pharmaceutically acceptable salt thereof and any of the methods may employ the compounds of the invention as a pharmaceutically acceptable composition. A pharmaceutically acceptable composition includes one or more of the compounds of the invention together with a pharmaceutical excipient. The pharmaceutical compositions of the invention include those suitable for oral, rectal, nasal, topical (including buccal and sublingual), vaginal or parenteral (including subcutaneous, intramuscular, intravenous, intraperitoneal, intracardiac, intradermal, transdermal and intra-tumoral) administration.

Compounds of this invention may be used in a pharmaceutical formulation comprising a compound of this invention and an excipient. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in "Remington: The Science and Practice of Pharmacy", 21st Ed. (Lippincott Williams & Wilkins 2005), the disclosure of which is incorporated herein by reference.

The compounds or compositions may be prepared as any available dosage form. Unit dosage forms are also intended, which includes discrete units of the compound or composition such as capsules, sachets or tablets each containing a predetermined amount of the compound; as a powder or granules; as a solution or a suspension in an aqueous liquid or a non-aqueous liquid; or as an oil-in-water liquid emulsion or a water-in-oil liquid emulsion, or packed in liposomes and as a bolus or the like.

A tablet containing the compound or composition may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. Nos. 4,369,174 and 4,842,866, and references cited therein. Coatings can be used for delivery of compounds to the intestine (see, e.g. U.S. Pat. Nos. 6,638,534, 5,217,720 and 6,569,457, and references cited therein). A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. In one variation, the aqueous composition is acidic, having a pH of about 5.5 to about 7.

Extemporaneous injection solutions and suspensions may be prepared from sterile powders, granules and tablets.

Administration of the compounds or compositions to an individual may involve systemic exposure or may be local administration, such as when a compound or composition is to be administered at the site of interest. Various techniques can be used for providing the subject compositions at the site of interest, such as via injection, use of catheters, trocars, projectiles, pluronic gel, stems, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. The methods of the invention embrace administration of the compounds to an organ to be donated (such as to prevent ischemia/reperfusion injury). Accordingly, organs that are removed from one individual for transplant into another individual may be bathed in a medium containing or otherwise exposed to a compound or composition as described herein.

The compounds of the invention, such as those of the formulae herein, may be administered in any suitable dosage amount, which may include dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.1 mg/kg/day and 90 mg/kg/day and the upper end of the range is any amount between 1 mg/kg/day and −32 1 00 mg/kg/day (e.g., 0.5 mg/kg/day and 2 mg/kg/day, 5 mg/kg/day and 20 mg/kg/day). The dosing interval can be adjusted according to the needs of the individual. For longer intervals of administration, extended release or depot formulations can be used. The dosing can be commensurate with intravenous administration. For instance, the compound can be administered, such as in a pharmaceutical composition that is amenable to intravenous administration, in an amount of between about 0.01 µg/kg/min to about 100 µg/kg/min or between about 0.05 µg/kg/min to about 95 µg/kg/min or between about 0.1 µg/kg/min to about 90 µg/kg/min or between about 1.0 µg/kg/min to about 80 µg/kg/min or between about 10.0 µg/kg/min to about 70 µg/kg/min or between about 20 µg/kg/min to about 60 µg/kg/min or between about 30 µg/kg/min to about 50 µg/kg/min or between about 0.01 µg/kg/min to about 1.0 µg/kg/min or between about 0.01 µg/kg/min to about 10 µg/kg/min or between about 0.1 µg/kg/min to about 1.0 µg/kg/min or between about 0.1 µg/kg/min to about 10 µg/kg/min or between about 1.0 µg/kg/min to about 5 µg/kg/min or between about 70 µg/kg/min to about 100 µg/kg/min or between about 80 µg/kg/min to about 90 µg/kg/min. In one variation, the compound is administered to an individual, such as in a pharmaceutical composition that is amenable to intravenous administration, in an amount of at least about 0.01 µg/kg/min or at least about 0.05 µg/kg/min or at least about 0.1 µg/kg/min or at least about 0.15 µg/kg/min or at least about 0.25 µg/kg/min or at least about 0.5 µg/kg/min or at least about 1.0 µg/kg/min or at least about 1.5 µg/kg/min or at least about 5.0 µg/kg/min or at least about 10.0 µg/kg/min or at least about 20.0 µg/kg/min or at least about 30.0 µg/kg/min or at least about 40.0 µg/kg/min or at least about 50.0 µg/kg/min or at least about 60.0 µg/kg/min or at least about 70.0 µg/kg/min or at least about 80.0 µg/kg/min or at least about 90.0 µg/kg/min or at least about 100.0 µg/kg/min or more. In another variation, the compound is administered to an individual, such as in a pharmaceutical composition that is amenable to intravenous administration, in an amount of less than about 100.0 µg/kg/min or less than about 90.0 µg/kg/min or less than about 80.0 µg/kg/min or less than about 80.0 µg/kg/min or less than about 70.0 µg/kg/min or less than about 60.0 µg/kg/min or less than about 50.0 µg/kg/min or less than about 40.0 µg/kg/min or less than about 30.0 µg/kg/min or less than about 20.0 µg/kg/min or less than about 10.0 µg/kg/min or less than about 5.0 µg/kg/min or less than about 2.5 µg/kg/min or less than about 1.0 µg/kg/min or less than about 0.5 µg/kg/min or less than about 0.05 µg/kg/min or less than about 0.15 µg/kg/min or less than about 0.1 µg/kg/min or less than about 0.05 µg/kg/min or less than about 0.01 µg/kg/min.

The invention further provides kits comprising one or more compounds as described herein. The kits may employ any of the compounds disclosed herein and instructions for use. The compound may be formulated in any acceptable form. The kits may be used for any one or more of the uses described herein, and, accordingly, may contain instructions for any one or more of the stated uses (e.g., treating and/or preventing and/or delaying the onset and/or the development of a disease or condition that is responsive to nitroxyl therapy, e.g. heart failure, ischemia/reperfusion injury or cancer).

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention (e.g., treating, preventing and/or delaying the onset and/or the development of heart disease or ischemia/reperfusion injury). The instructions included with the kit generally include information as to the components and their administration to an individual.

EXAMPLES

The practice of this invention can be further understood by reference to the following examples, which are provided by way of illustration and not of limitation.

All NMR were recorded on one of the following instruments; Bruker AVANCE 400 MHz spectrometer, Bruker 250 or Bruker 360 operating at ambient probe temperature using an internal deuterium lock. Chemical shifts are reported in parts per million (ppm) at lower frequency relative to tetramethylsilane (TMS). Standard abbreviations are used throughout (s: singlet; br. s: broad singlet; d: doublet; dd: doublet of doublets; t: triplet; q: quartet; quin: quintet; m: multiplet). Coupling constants are reported in Hertz (Hz).

Example 1

Synthesis of Oxime Intermediates

The following oximes were prepared according to General Method 1:

Example 1A

Tetrahydro-pyran-4-one oxime: To a solution of hydroxylamine hydrochloride (1.53 g, 22 mmol) in acetonitrile: water (10 ml:5 ml) at ambient temperature was added sodium acetate (1.8 g, 22 mmol) and tetrahydro-pyran-4-one (2.0 g, 20 mmol) with stirring. After 3 hours the solvents were removed in vacuo and the reaction quenched with potassium carbonate solution (10 ml). The organics were extracted into DCM (3×50 ml), combined, dried over $Na_2SO_4$ and concentrated in vacuo to afford tetrahydro-pyran-4-one oxime without need for further purification (1.72 g, 75% yield). $^1H$ NMR (360 MHz, DMSO-$d_6$) δδ 10.38 (1H, s), 3.67 (2H, t, 5.7 Hz), 3.60 (2H, t, 5.9 Hz), 2.48 (2H, t, 5.9 Hz), 2.23 (2H, t, 5.7 Hz).

Example 1B

1-Methyl-piperidin-4-one oxime was prepared from 1-methyl-piperidin-4-one and hydroxylamine hydrochloride using conditions of General Method 1. $^1H$ NMR (400 MHz, DMSO-$d_6$) δ 10.31 (1H, s), 2.45 (2H, t, 6.1 Hz), 2.38 (2H, t, 5.9 Hz), 2.31 (2H, t, J=6.0 Hz), 2.20 (2H, t, 6.4 Hz), 2.18 (3H, s).

Example 1C

1-Acetyl-piperidin-4-one oxime was prepared from 1-acetyl-piperidin-4-one and hydroxylamine using conditions of General Method 1. $^1H$ NMR (400 MHz, DMSO-$d_6$) δ 10.48 (1H, d, 3.2 Hz), 3.43-3.56 (4H, m), 2.48-2.56 (1H, m), 2.42 (1H, t, 6.2 Hz), 2.29-2.34 (1H, m), 2.17-2.26 (1H, m), 2.03 (3H, d, 4.2 Hz).

Example 1D

1-Benzoyl-piperidin-4-one oxime was prepared from 1-benzoyl-piperidin-4-one and hydroxylamine hydrochloride using conditions of General Method 1. $^1H$ NMR (400 MHz, DMSO-$d_6$) δ 10.53 (1H, br. s.), 7.29-7.54 (5H, m), 3.49-3.81 (4H, m), 2.44-2.66 (2H, m), 2.17-2.42 (2H, m).

Example 1E 1,3-Diethoxy-propan-2-one oxime was prepared from 1,3-diethoxy-propan-2-one and hydroxylamine hydrochloride using conditions of General Method 1. $^1H$ NMR (400 MHz, DMSO-$d_6$) δ 11.06 (1H, s), 4.18 (2H, s), 3.96 (2H, s), 3.41 (4H, quin, 7.0 Hz), 1.10 (6H, q, 7.1 Hz).

Example 1F 1,2,2,6,6-Pentamethyl-piperidin-4-one oxime was prepared from 1,2,2,6,6-pentamethyl-piperidin-4-one and hydroxylamine hydrochloride using conditions of General Method 1. 1H NMR (250 MHz, CHLOROFORM-d) δ 2.52 (2H, s), 2.28 (3H, s), 2.21 (2H, s), 1.12 (6H, s), 1.11 (6H, s).

Example 1G ({8-Methyl-8-azabicyclo[3.2.1]octan-3-ylidene}amino) ol was prepared from tropinone and hydroxylamine hydrochloride using conditions of General Method 1. $^1H$ NMR (250 MHz, CHLOROFORM-d) δ 3.20-3.42 (2H, m), 2.90-3.10 (1H, m), 2.59 (1H, dd, 15.0, 3.4 Hz), 2.39 (3H, s), 2.08-2.29 (2H, m), 1.91-2.08 (2H, m), 1.41-1.72 (2H, m).

Example 1H 3-(Acetyloxy)-2-(hydroxyimino)propyl acetate was prepared from 3-(acetyloxy)-2-oxopropyl acetate (*Tetrahedron Lett.*, 2001; 3331-3334) and hydroxylamine hydrochloride using conditions of General Method 1. 1H NMR (250 MHz, CHLOROFORM-d) δ 8.32 (1H, br. s.), 5.02 (2H, s), 4.75 (2H, s), 2.11 (3H, s), 2.10 (3H, s).

Example 2

Preparation of 4-nitrosotetrahydro-2H-pyran-4-yl acetate

4-Nitrosotetrahydro-2H-pyran-4-yl acetate was prepared according to General Method 2. A solution of tetrahydro-pyran-4-one oxime (3.0 g, 26.1 mmol) in DCM (50 ml) was added dropwise to a solution of lead tetraacetate (11.57 g, 26.1 mmol) in DCM (100 ml) at 0° C. A blue color gradually appears on addition of the oxime solution. Upon complete addition (1 hour) the reaction was allowed to warm to ambient temperature and stirring was continued for a further 2-3 hours. The reaction was quenched by the addition of water, the phases separated and the organics dried over $Na_2SO_4$ and concentrated in vacuo to afford 4-nitrosotetrahydro-2H-pyran-4-yl acetate which was purified by column chromatography on silica gel with a gradient of pentane: EtOAc as the eluent to afford the title compound as a blue oil in 56% yield. $^1H$ NMR (250 MHz, CHLOROFORM-d) δ 1.84 (2H, m), 2.18 (2H, m), 2.25 (3H, s), 3.71 (2H, m), 4.03 (2H, m).

Example 3

Preparation of 1-methyl-4-nitrosopiperidin-4-yl acetate

1-Methyl-4-nitrosopiperidin-4-yl acetate was prepared from 1-methyl-piperidin-4-one oxime and lead tetraacetate using conditions of General Method 2. $^1H$ NMR (400 MHz, chloroform-d) δ 2.86-2.91 (2H, m), 2.36 (3H, s), 2.29 (2H, s), 2.27 (2H, t, 2.2 Hz), 2.22 (3H, s), 1.85-1.91 (2H, m).

Example 4

Preparation of 1-acetyl-4-nitrosopiperidin-4-yl acetate

1-Acetyl-4-nitrosopiperidin-4-yl acetate was prepared from 1-acetyl-piperidin-4-one oxime and lead tetraacetate using conditions of General Method 2. $^1H$ NMR (400 MHz, chloroform-d) δ 4.51 (1H, ddd, 9.8, 8.3, 4.4 Hz), 3.87 (1H, ddd, 10.0, 8.7, 5.0 Hz), 3.41 (1H, dd, 11.5, 3.2 Hz), 3.05 (1H, dd, 13.4, 7.8 Hz), 2.26 (3H, s), 2.15 (3H, s), 2.10-2.18 (1H, m), 1.94-2.02 (2H, m), 1.81-1.90 (1H, m).

Example 5

Preparation of 1,3-diethoxy-2-nitrosopropan-2-yl acetate 1,3-Diethoxy-2-nitrosopropan-2-yl acetate was prepared from 1,3-diethoxy-propan-2-one oxime and lead tetraacetate using conditions of General Method 2. $^1$H NMR (250 MHz, chloroform-d) δ 4.09 (4H, q), 3.16-3.68 (4H, m), 2.17 (3H, s), 1.06 (6H, t).

Example 6

Preparation of 3-nitrosotetrahydrothiophen-3-yl acetate

3-Nitrosotetrahydrothiophen-3-yl acetate was prepared from tetrahydrothiophen-3-one oxime and lead tetraacetate using conditions of General Method 2. $^1$H NMR (400 MHz, chloroform-d) δ 3.69 (1H, d, 13.2 Hz), 3.11 (1H, d, 13.2 Hz), 2.99-3.05 (2H, m), 2.50-2.61 (1H, m), 2.22-2.29 (1H, m), 2.22 (3H, s).

Example 7

Preparation of 1-benzoyl-4-nitrosopiperidin-4-yl acetate

1-Benzoyl-4-nitrosopiperidin-4-yl acetate was prepared from 1-benzoyl-piperidin-4-one oxime and lead tetraacetate using conditions of General Method 2. $^1$H NMR (400 MHz, chloroform-d) δ 7.42-7.48 (5H, m), 4.40-4.86 (1H, m), 3.63-4.13 (1H, m), 3.14-3.52 (2H, m), 2.26 (3H, s), 2.05-2.19 (2H, m), 1.80-2.04 (2H, m).

Example 8

Preparation of 1,2,2,6,6-pentamethyl-4-nitrosopiperidin-4-yl acetate 1,2,2,6,6-Pentamethyl-4-nitrosopiperidin-4-yl acetate was prepared from 1,2,2,6,6-pentamethyl-piperidin-4-one oxime and lead tetraacetate using conditions of General Method 2. 1H NMR (500 MHz, CHLOROFORM-d) δ 2.43 (3H, s), 2.29-2.40 (2H, m), 2.20 (3H, s), 1.81 (2H, d, 13.9 Hz), 1.28 (6H, s), 1.23 (6H, s).

Example 9

Preparation of 2-nitrosopropane-1,2,3-triyl triacetate

2-Nitrosopropane-1,2,3-triyl triacetate was prepared from 3-(acetyloxy)-2-(hydroxyimino)propyl acetate and lead tetraacetate using conditions of General Method 2. 1H NMR (250 MHz, CHLOROFORM-d) δ 4.50-4.92 (4H, m), 2.21 (3H, s), 2.06 (6H, s).

Example 10

Preparation of 8-methyl-3-nitroso-8-azabicyclo[3.2.1]oct-3-yl acetate

8-Methyl-3-nitroso-8-azabicyclo[3.2.1]oct-3-yl acetate was prepared from ({8-methyl-8-azabicyclo[3.2.1]octan-3-ylidene}amino)ol and lead tetraacetate using conditions of General Method 2. 1H NMR (500 MHz, CHLOROFORM-d) δ 3.49-3.55 (2H, m), 2.63 (2H, d, 15.3 Hz), 2.50 (3H, s), 2.21 (3H, s), 2.12-2.19 (2H, m), 2.07 (3H, s), 1.92-2.01 (2H, m), 1.79-1.88 (2H, m).

Example 11

Preparation of 1-nitrosocyclohexyl 2,4-dichlorobenzoate

1-Nitrosocyclohexyl 2,4-dichlorobenzoate was prepared according to General Method 3. A solution of cyclohexanone oxime (2.66 g, 23.5 mmol) in DCM (50 ml) was added dropwise to a solution of lead tetra acetate (10.42 g, 23.5 mmol) and 2,4 dichlorobenzoic acid (45.0 g, 235 mmol) in DCM (300 ml) at 0° C. A blue color gradually appears on addition of the oxime solution. Upon complete addition (1 hour) the reaction was allowed to warm to ambient temperature and stirring was continued for a further 2-3 hours. The reaction was quenched by the addition of water, the phases separated and the organics dried over $Na_2SO_4$ and concentrated in vacuo to afford 1-nitrosocyclohexyl 2,4-dichlorobenzoate which was purified by column chromatography on silica gel with hexane:EtOAc as the eluent to afford the title compound as a blue oil in 9% yield. $δ_H$ (400 MHz, DMSO-$d_6$) δ 8.02 (1H, d, 8.4 Hz), 7.85 (1H, d, 2.0 Hz), 7.64 (1H, dd, 8.4, 2.0 Hz), 2.03-2.12 (2H, m), 1.38-1.93 (8H, m).

Example 12

Preparation of 1-nitrosocyclohexyl isobutyrate

1-Nitrosocyclohexyl isobutyrate was prepared from cyclohexanone oxime, lead tetraacetate and isobutyric acid using conditions of General Method 3. $^1$H NMR (400 MHz, chloroform-d) δ 2.68-2.79 (1H, sept, 7.0 Hz), 1.71-1.93 (8H, m), 1.48-1.62 (2H, m), 1.29 (3H, s), 1.27 (3H, s).

Example 13

Preparation of 1-methyl-4-nitrosopiperidin-4-yl isobutyrate

1-Methyl-4-nitrosopiperidin-4-yl isobutyrate was prepared from 1-methyl-piperidin-4-one oxime, lead tetraacetate and isobutyric acid using conditions of General Method 3. $^1$H NMR (400 MHz, chloroform-d) δ 2.82-2.94 (2H, m), 2.65 (1H, sept, 7.0 Hz), 2.36 (3H, s), 2.23-2.35 (4H, m), 1.83-1.92 (2H, m), 1.28 (3H, s), 1.27 (3H, s).

Example 14A

Preparation of 1-methyl-4-nitrosopiperidin-4-yl 2,4-difluorobenzoate

1-Methyl-4-nitrosopiperidin-4-yl 2,4-difluorobenzoate was prepared from 1-methyl-piperidin-4-one oxime, lead tetraacetate and 2,4-difluorobenzoic acid using conditions of General Method 3. $^1$H NMR (400 MHz, chloroform-d) δ 7.59 (2H, dd, 7.5, 2.3 Hz), 7.09 (1H, tt, 8.6, 2.4 Hz), 2.98 (2H, dt, 11.7, 3.6 Hz), 2.32-2.50 (7H, m), 2.04 (2H, dd, 14.2, 2.7 Hz).

Example 14B

Preparation of 1-methyl-4-nitrosopiperidin-4-yl 3,5-difluorobenzoate

1-Methyl-4-nitrosopiperidin-4-yl 3,5-difluorobenzoate is prepared from 1-methyl-piperidin-4-one oxime, lead tetraacetate and 3,5-difluorobenzoic acid using conditions of General Method 3.

Example 15

Preparation of 1-nitrosocyclohexyl 2-chloro-2,2-difluoroacetate

1-Nitrosocyclohexyl 2-chloro-2,2-difluoroacetate was prepared from cyclohexanone oxime, lead tetraacetate and 2-chloro-2,2-difluoroacetic acid using conditions of General Method 3. $^1$H NMR (250 MHz, chloroform-d) δ 2.13-2.42 (3H, m), 1.79-1.99 (4H, m), 1.51-1.74 (3H, m).

Example 16

Preparation of 1-nitrosocyclohexyl 4,4,4-trifluoro-3-methylbutanoate

1-Nitrosocyclohexyl 4,4,4-trifluoro-3-methylbutanoate was prepared from cyclohexanone oxime, lead tetraacetate and 4,4,4-trifluoro-3-methyl butanoic acid using conditions of General Method 3. $^1$H NMR (250 MHz, chloroform-d) δ 2.69-2.92 (1H, m), 2.69-2.92 (1H, m), 2.47 (1H, d, 6.5 Hz), 1.71-2.05 (4H, m), 1.42-1.63 (2H, m), 1.27 (3H, d, 6.9 Hz), 1.10-1.39 (2H, m), 0.87 (1H, d, 7.0 Hz), 0.78-0.99 (1H, m).

Example 17

Preparation of 4-nitrosotetrahydro-2H-pyran-4-yl 2,2,2-trifluoroacetate

4-Nitrosotetrahydro-2H-pyran-4-yl 2,2,2-trifluoroacetate was prepared from tetrahydro-pyran-4-one oxime, lead tetraacetate and trifluoroacetic acid using conditions of General Method 3. $^1$H NMR (250 MHz, chloroform-d) δ 4.18 (2H, m), 3.75 (2H, m), 2.53 (2H, m), 1.92 (2H, m).

Example 18

Preparation of 4-nitrosotetrahydro-2H-pyran-4-yl 3,3,3-trifluoropropanoate

4-Nitrosotetrahydro-2H-pyran-4-yl 3,3,3-trifluoropropanoate was prepared from tetrahydro-pyran-4-one oxime, lead tetraacetate and 3,3,3-trifluoropropionic acid using conditions of General Method 3. $^1$H NMR (360 MHz, chloroform-d) δ 3.94-4.17 (2H, m), 3.54-3.79 (2H, m), 3.37 (2H, q), 2.23-2.43 (2H, m), 1.65-1.96 (2H, m).

Example 19

Preparation of 4-nitrosotetrahydro-2H-pyran-4-yl 4,4,4-trifluorobutanoate

4-Nitrosotetrahydro-2H-pyran-4-yl 4,4,4-trifluorobutanoate was prepared from tetrahydro-pyran-4-one oxime, lead tetraacetate and 4,4,4,-trifluorobutyric acid using conditions of General Method 3. $^1$H NMR (250 MHz, chloroform-d) δ 3.91-4.19 (2H, m), 3.48-3.83 (2H, m), 2.71-2.94 (2H, m), 2.36-2.67 (2H, m), 2.15-2.34 (2H, m), 1.63-1.96 (2H, m).

Example 20

Preparation of 1-nitrosocyclohexyl 2,2,3,3,3-pentafluoropropanoate

1-Nitrosocyclohexyl 2,2,3,3,3-pentafluoropropanoate was prepared from cyclohexanone oxime, lead tetraacetate and pentafluoropropionic acid using conditions of General Method 3. $^1$H NMR (360 MHz, chloroform-d) δ 2.35-2.31 (2H, m), 1.77-2.00 (4H, m), 1.49-1.72 (4H, m).

Example 21

Preparation of 1-nitrosocyclohexyl 2-cyanoacetate

1-Nitrosocyclohexyl 2-cyanoacetate was prepared from cyclohexanone oxime, lead tetraacetate and cyanoacetic acid using conditions of General Method 3. $^1$H NMR (250 MHz, chloroform-d) δ 3.62 (2H, s), 2.01-2.21 (2H, m), 1.70-1.97 (5H, m), 1.41-1.69 (3H, m).

Example 22

Preparation of 4-nitrosotetrahydro-2H-pyran-4-yl 2,2,2-trichloroacetate

4-Nitrosotetrahydro-2H-pyran-4-yl 2,2,2-trichloroacetate was prepared from tetrahydro-pyran-4-one oxime, lead tetraacetate and trichloroacetic acid using conditions of General Method 3. $^1$H NMR (360 MHz, chloroform-d) δ 3.99-4.19 (2H, m), 3.61-3.94 (2H, m), 2.30-2.61 (2H, m), 1.58-2.03 (2H, m).

Example 23

Preparation of 4-nitrosotetrahydro-2H-pyran-4-yl 2,2,3,3,3-pentafluoropropanoate 4-Nitrosotetrahydro-2H-pyran-4-yl 2,2,3,3,3-pentafluoropropanoate was prepared from tetrahydro-pyran-4-one oxime, lead tetraacetate and pentafluoropropionic acid using conditions of General Method 3. $^1$H NMR (250 MHz, chloroform-d) δ 4.11-4.30 (2H, m), 3.46-3.83 (2H, m), 2.45-2.73 (2H, m), 1.68-2.02 (2H, m).

Example 24

Preparation of 4-nitrosotetrahydro-2H-pyran-4-yl 2-chloro-2,2-difluoroacetate

4-Nitrosotetrahydro-2H-pyran-4-yl 2-chloro-2,2-difluoroacetate was prepared from tetrahydro-pyran-4-one oxime, lead tetraacetate and chlorodifluoroacetic acid using conditions of General Method 3. $^1$H NMR (360 MHz, chloroform-d) δ 4.06-4.23 (2H, m), 3.52-3.86 (2H, m), 2.27-2.70 (2H, m), 1.72-2.07 (2H, m).

Example 25

Preparation of (S)-4-nitrosotetrahydro-2H-pyran-4-yl 2-acetamido-3-phenylpropanoate (S)-4-Nitrosotetrahydro-2H-pyran-4-yl 2-acetamido-3-phenyl propanoate was prepared from tetrahydro-pyran-4- one oxime, lead tetraacetate and (S)-2-acetylamino-3-phenyl-propionic acid using conditions of General Method 3. $^1$H NMR (400 MHz, chloroform-d) δ 7.09-7.46 (5H, m), 5.92 (1H, d, 7.3 Hz), 4.93-5.12 (1H, m), 3.86-4.10 (2H, m), 3.43-3.68 (2H, m), 3.19-3.36 (2H, m), 2.06-2.68 (2H, m), 1.93-2.08 (3H, m), 1.81-1.93 (1H, m), 1.47-1.69 (1H, m).

Example 26

Preparation of 4-nitrosotetrahydro-2H-pyran-4-yl pivalate

4-Nitrosotetrahydro-2H-pyran-4-yl pivalate was prepared from tetrahydro-pyran-4-one oxime, lead tetraacetate and trimethylacetic acid using conditions of General Method 3. $^1$H NMR (360 MHz, chloroform-d) δ 3.91-4.14 (2H, m), 3.57-3.77 (2H, m), 2.10-2.29 (2H, m), 1.75-1.93 (2H, m), 1.34 (9H, s).

Example 27

Preparation of diethyl 1-nitrosocyclohexyl phosphate

Diethyl 1-nitrosocyclohexyl phosphate was prepared from cyclohexanone oxime, lead tetraacetate and diethyl phosphate using conditions of General Method 3. $^1$H NMR (400 MHz, benzene-d$_6$) δ 3.90-4.15 (3H, m), 1.24-1.78 (10H, m), 0.88-1.10 (7H, m)

Example 28

Preparation of dibutyl 1-nitrosocyclohexyl phosphate

Dibutyl 1-nitrosocyclohexyl phosphate was prepared from cyclohexanone oxime, lead tetraacetate and dibutyl phosphate using conditions of General Method 3. $^1$H NMR (400 MHz, chloroform-d) δ 4.12-4.21 (1H, m), 4.00 (3H, q, 6.7 Hz), 1.61-1.79 (6H, m), 1.36-1.48 (5H, m), 1.25-1.35 (4H, m), 0.86-0.97 (9H, m).

Example 29

Preparation of dibutyl 1-methyl-4-nitrosopiperidin-4-yl phosphate

Dibutyl 1-methyl-4-nitrosopiperidin-4-yl phosphate was prepared from 1-methyl-piperidin-4-one oxime, lead tetraacetate and dibutyl phosphate using conditions of General Method 3. $^1$H NMR (360 MHz, chloroform-d) δ 4.03-4.17 (4H, m), 2.77-2.88 (2H, m), 2.27-2.40 (6H, m), 2.12-2.24 (4H, m), 1.59-1.83 (6H, m), 1.38 (4H, q, 7.2 Hz).

Example 30

Preparation of 1-methyl-4-nitrosopiperidin-4-yl pivalate

1-Methyl-4-nitrosopiperidin-4-yl pivalate was prepared from 1-methyl piperidin-4-one oxime, lead tetraacetate and trimethylacetic acid using conditions of General Method 3. 1H NMR (400 MHz, CHLOROFORM-d) δ 2.86-3.00 (2H, m), 2.37 (3H, s), 2.21-2.35 (4H, m), 1.82-1.94 (2H, m), 1.32 (9H, s).

Example 31

Preparation of 1,2,2,6,6-pentamethyl-4-nitrosopiperidin-4-yl pivalate 1,2,2,6,6-Pentamethyl-4-nitrosopiperidin-4-yl pivalate was prepared from 1,2,2,6,6-pentamethyl-piperidin-4-one oxime, lead tetraacetate and trimethylacetic acid using conditions of General Method 3. 1H NMR (250 MHz, CHLOROFORM-d) δ 2.43-2.64 (5H, m), 2.09 (3H, s), 1.91 (2H, d, 14.2 Hz), 1.39 (6H, d, 5.9 Hz), 1.30 (9H, s), 1.25 (6H, d, 2.6 Hz).

Example 32

Preparation of 1-benzoyl-4-nitrosopiperidin-4-yl 2,2,2-trifluoroacetate

1-Benzoyl-4-nitrosopiperidin-4-yl 2,2,2-trifluoroacetate was prepared according to General Method 4. To a solution of bis(trifluoroacetoxy)iodobenzene (990 mg, 2.3 mmol) in DCM (25 ml) cooled to 0° C. was added a solution of 1-benzoyl-piperidin-4-one oxime (500 mg, 2.3 mmol) in DCM (20 ml). After 2 hours the reaction was concentrated in vacuo and purified by column chromatography on silica gel with DCM as the eluent to afford the title compound as a blue oil in 32% yield. $^1$H NMR (400 MHz, chloroform-d) δ 7.43-7.53 (5H, m), 4.90-4.64 (1H, m), 4.19-3.89 (1H, m), 3.49-3.28 (2H, m), 2.64-2.34 (2H, m), 2.11-1.84 (2H, m).

Example 33

Preparation of 4-nitrosotetrahydro-2H-pyran-4-yl 2-benzamidoacetate

4-Nitrosotetrahydro-2H-pyran-4-yl 2-benzamidoacetate was prepared from tetrahydro-pyran-4-one oxime and bis(benzoylaminoacetoxy)iodobenzene (synthesized from iodobenzene diacetate and benzoylaminoacetic acid) using conditions of General Method 4. $^1$H NMR (400 MHz, chloroform-d) δ 7.15-7.28 (5H, m), 4.39 (2H, d, 5.4 Hz), 4.03 (2H, m), 3.71 (2H, m), 2.18 (2H, m), 1.84 (2H, m).

Example 34

Preparation of 4-nitrosotetrahydro-2H-pyran-4-yl 2-acetamidopropanoate

4-Nitrosotetrahydro-2H-pyran-4-yl 2-acetamidopropanoate was prepared from tetrahydro-pyran-4-one oxime and bis(2-acetylamino-propionate)iodobenzene (synthesized from iodobenzene diacetate and 2-acetylamino-propionic acid) using conditions of General Method 4. $^1$H NMR (250 MHz, chloroform-d) δ 6.04 (1H, d, 6.9 Hz), 4.54-4.85 (1H, m), 3.60-3.91 (4H, m), 2.68 (2H, t, 5.8 Hz), 2.38 (2H, t, 5.6 Hz), 2.03 (3H, s), 1.50-1.63 (3H, m).

Example 35

Preparation of 4-nitrosotetrahydro-2H-pyran-4-yl 3-(5-oxotetrahydrofuran-2-yl)propanoate 4-Nitrosotetrahydro-2H-pyran-4-yl-3-(5-oxotetrahydrofuran-2-yl)propanoate was prepared from tetrahydro-pyran-4-one oxime and bis(3-(5-oxo-tetrahydro-furan-2-yl)-propanato) iodobenzene (synthesized from iodobenzene diacetate and 3-(5-oxo-tetrahydro-furan-2-yl)-propionic acid) using conditions of General Method 4. 1H NMR (250 MHz, CHLOROFORM-d) δ 4.46-4.71 (1H, m), 3.92-4.15 (2H, m), 3.62-3.84 (2H, m), 1.77-2.80 (12H, m).

Example 36

Preparation of methyl 4-nitrosotetrahydro-2H-pyran-4-yl succinate

Methyl 4-nitrosotetrahydro-2H-pyran-4-yl succinate was prepared from tetrahydro-pyran-4-one oxime and bis(methyl succinate) iodobenzene (synthesized from iodobenzene diacetate and methyl succinic acid) using conditions of General Method 4. 1H NMR (250 MHz, CHLOROFORM-d) δ 3.94-4.12 (2H, m), 3.59-3.80 (5H, m), 2.79-2.94 (2H, m), 2.62-2.75 (2H, m), 2.09-2.30 (2H, m), 1.73-1.90 (2H, m).

Example 37

Preparation of 2-methyl-2-(4-nitrosotetrahydro-2H-pyran-4-yloxy)carbonyl)propane-1,3-diyl diacetate 2-Methyl-2-((4-nitrosotetrahydro-2H-pyran-4-yloxy)carbonyl)propane-1,3-diyl diacetate was prepared from tetrahydro-pyran-4-one oxime and bis(3-acetoxy-2-acetoxymethyl-2-methyl-propionate) iodobenzene (synthesized from iodobenzene diacetate and 3-acetoxy-2-acetoxymethyl-2-methyl-propionic acid which was in turn synthesized using the reported method J. Am. Chem. Soc., 118, 1996, 6388-6395) using conditions of General Method 4. 1H NMR (250 MHz, CHLOROFORM-d) δ 4.32 (4H, s), 3.98-4.17 (2H, m), 3.54-3.74 (2H, m), 2.28-2.46 (2H, m), 2.13 (6H, s), 1.77-1.94 (2H, m), 1.40 (3H, s).

Example 38

Preparation of 4-nitrosotetrahydro-2H-pyran-4-yl 4-acetoxy-3-(acetoxymethyl)butanoate 4-Nitrosotetrahydro-2H-pyran-4-yl 4-acetoxy-3-(acetoxymethyl) butanoate was prepared from tetrahydro-pyran-4-one oxime and bis(4-acetoxy-3-acetoxymethyl-butyrate) iodobenzene using conditions of General Method 4. (4-acetoxy-3-acetoxymethyl-butyric acid was synthesized according to the methods in Tetrahedron: Asymmetry, 1997, 4079-4088 and Sov. J. Bioorg. Chem. 1977, 323-324), 1H NMR (250 MHz, CHLOROFORM-d) δ 4.83 (2H, m), 4.63 (2H, m), 2.21 (3H, s), 2.06 (6H, s).

Example 39

Preparation of 1-methyl 4-(4-nitrosotetrahydro-2H-pyran-4-yl) N-[(benzyloxy)carbonyl]aspartate 1-Methyl 4-(4-nitrosotetrahydro-2H-pyran-4-yl)N-[(benzyloxy)carbonyl] aspartate was prepared from tetrahydro-pyran-4-one oxime and bis((S)-(+)-3-(benzyloxycarbonyl)-5-oxo-4-oxazolidine) iodobenzene using conditions of General Method 4. 1H NMR (500 MHz, CHLOROFORM-d) δ 7.31-7.42 (4H, m), 5.73 (1H, d, 8.1 Hz), 5.16 (2H, s), 4.68-4.74 (1H, m), 4.00-4.08 (2H, m), 3.81 (2H, s), 3.63-3.72 (2H, m), 3.06-3.26 (2H, m), 2.20-2.30 (2H, m), 1.75-1.86 (2H, m).

Example 40

Preparation of 1-tert-butyl 4-(4-nitrosotetrahydro-2H-pyran-4-yl)N-(tert-butoxycarbonyl)aspartate 1-tert-Butyl 4-(4-nitrosotetrahydro-2H-pyran-4-yl)N-(tert-butoxycarbonyl)aspartate was prepared from tetrahydropyran-4-one oxime and bis(Boc-Asp-O$^t$Bu)-iodobenzene using conditions of General Method 4. 1H NMR (500 MHz, CHLOROFORM-d) δ 5.42 (1H, d, 7.7 Hz), 4.45-4.53 (1H, m), 3.99-4.09 (2H, m), 3.68-3.76 (2H, m), 3.02-3.18 (2H, m), 2.15-2.30 (2H, m), 1.74-1.93 (2H, m), 1.48 (9H, s), 1.46 (9H, s).

Example 41

Preparation of 4-nitrosotetrahydro-2H-pyran-4-yl 4-(acetoxy)butanoate

Benzyl-4-bromobutanoate was synthesized according to the methods in J. Med. Chem., 1996, 39, 5176-5182.

Benzyl-4-(acetoxy)butanoate was synthesized from 4-bromobenzylbutyrate and potassium acetate. To a solution of 4-bromobenzylbutyrate (1.0 g, 3.89 mmol) in acetonitrile (25 ml) was added potassium acetate (5.94 g, 7.78 mmol). The reaction was heated to 90° C. for 18 hours and monitored by TLC (4:1 heptane:EtOAc) The mixture was allowed to cool to room temperature and concentrated in vacuo. The crude product was extracted with water:EtOAc and the organic phase was separated, dried over $Na_2SO_4$, filtered and concentrated in vacuo. The title compound was isolated in sufficient purity without need for further purification. (0.8 g, 87% yield). $^1$H NMR (250 MHz, DMSO-$d_6$) δ 7.29-7.41 (5H, m), 5.09 (2H, s), 4.01 (2H, t, 6.5 Hz), 2.44 (2H, t, 7.3 Hz), 1.97 (3H, s), 1.85 (2H, quin, 6.9 Hz).

4-Acetoxy-butyric acid was synthesized from 4-acetoxybenzylbutyrate. To a solution of 4-acetoxybenzylbutyrate (1 g, 4.3 mmol) in EtOH (10 ml) was added palladium on charcoal (50 mg, 10% w:w) under an atmosphere of $H_2$. After 30 minutes at atmospheric temperature/pressure complete saponification of the benzyl ester was observed. The compound was isolated by filtration and concentration in vacuo. (0.66 g, 100% yield). $^1$H NMR (500 MHz, CHLOROFORM-d) δ 4.13 (2H, t, 6.3 Hz,), 2.46 (2H, t, 7.3 Hz), 2.06 (3H, s), 1.98 (2H, quin, 6.8 Hz).

4-Nitrosotetrahydro-2H-pyran-4-yl 4-acetoxybutanoate was prepared from tetrahydropyran-4-one oxime and bis(4-acetoxy-butyrate) iodobenzene (synthesized from iodobenzene diacetate and 4-acetoxy-butyric acid) and using conditions of General Method 4. $^1$H NMR (500 MHz, CHLOROFORM-d) δ 4.18 (2H, t, 6.3 Hz), 4.05 (2H, dt, 4.2, 11.6 Hz), 3.71 (2H, td, 2.6, 11.4 Hz), 2.62 (2H, t, 7.4 Hz), 2.17-2.27 (2H, m), 2.08 (3H, s), 2.01-2.08 (2H, m), 1.85 (2H, dd, 2.4, 14.3 Hz).

Example 42

Preparation of 4-nitrosotetrahydro-2H-pyran-4-yl 4-(acetyloxy)-3-[(acetyloxy)methyl]but-2-enoate tert-Butyl 4-(acetyloxy)-3-[(acetyloxy)methyl]but-2-enoate was synthesized according to the methods in Tetrahedron: Asymmetry, 1997, 4079-4088 and Sov. J. Bioorg. Chem. 1977, 323-324.

4-Acetoxy-3-acetoxymethyl-but-2-enoic acid was synthesized from tert-butyl 4-(acetyloxy)-3-[(acetyloxy)methyl] but-2-enoate. tert-Butyl 4-(acetyloxy)-3-[(acetyloxy)

methyl]but-2-enoate (1.3 g, 4.8 mmol) was stirred in a 20% solution of TFA in DCM (20 ml) for 4 hours at ambient temperature. The title compound was isolated by concentration of the solution in vacuo as the TFA salt. (1 g, 4.7 mmol). $^1$H NMR (500 MHz, CHLOROFORM-d) δ 6.04 (1H, t, 1.6 Hz), 5.27 (2H, s), 4.78 (2H, s), 2.15 (3H, s), 2.11 (3H, s).

4-Nitrosotetrahydro-2H-pyran-4-yl 4-(acetyloxy)-3-[(acetyloxy)methyl]but-2-enoate was prepared from tetrahydropyran-4-one oxime and {[4-(acetyloxy)-3-[(acetyloxy) methyl]but-2-enoyl]oxy}(phenyl)-λ$^3$-iodanyl 4-(acetyloxy)-3-[(acetyloxy)methyl]but-2-enoate (synthesized from iodobenzene diacetate and 4-acetoxy-3-acetoxymethyl-but-2-enoic acid) and using conditions of General Method 4. $^1$H NMR (500 MHz, CHLOROFORM-d) δ 6.20 (1H, s), 5.21 (2H, s), 4.81 (2H, s), 4.05 (2H, dt, 4.0, 11.6 Hz), 3.74 (2H, td, 2.4, 11.4 Hz), 2.19-2.26 (2H, m), 2.18 (3H, s), 2.10 (3H, s), 1.89 (2H, d, 12.3 Hz).

Example 43

Preparation of 1-methyl-4-nitrosopiperidin-4-yl 4-(acetyloxy)-3-[(acetyloxy)methyl]butanoate 1-Methyl-4-nitrosopiperidin-4-yl 4-(acetyloxy)-3-[(acetyloxy)methyl]butanoate was prepared from 1-methyl-piperidin-4-one oxime and bis(4-acetoxy-3-acetoxymethylbutyrate) iodobenzene using conditions of General Method 4. $^1$H NMR (250 MHz, CHLOROFORM-d) δ 4.13-4.24 (4H, m), 2.36-2.63 (14H, m), 2.10 (3H, s), 2.88-2.94 (1H, m), 2.08 (3H, s), 1.92-1.96 (1H, m).

Example 44

Preparation of 4-nitrosotetrahydro-2H-pyran-4-yl (2S,3S)-2,3,4-tris(acetyloxy)butanoate Triacetyl-eryhronic acid was synthesized according to the method detailed in *J. Am. Chem. Soc.*, 1939, 61, 1720-1725

4-Nitrosotetrahydro-2H-pyran-4-yl (2S,3S)-2,3,4 tris (acetyloxy)butanoate enoate was prepared from tetrahydropyran-4-one oxime and bis ((2S,3S)-2,3,4 tris(acetyloxy) butanoate) iodobenzene (synthesized from iodobenzene diacetate and triacetyl-eryhronic acid) using conditions of General Method 4. NMR (500 MHz, CHLOROFORM-d) δ 5.54-5.58 (1H, m), 5.31 (1H, d, 4.1 Hz), 4.36-4.47 (2H, m), 3.92-4.07 (2H, m), 3.57-3.82 (2H, m), 2.44-2.31 (1H, m), 2.10-2.27 (1H, m), 2.11 (3H, s), 2.10 (3H, s), 2.01 (3H, s), 1.84-1.86 (1H, m), 1.70-1.73 (1H, m).

Example 45

Preparation of 4-nitrosotetrahydro-2H-pyran-4-yl 2-(acetyloxy)benzoate

4-Nitrosotetrahydro-2H-pyran-4-yl 2-(acetyloxy)benzoate was prepared from tetrahydro-pyran-4-one oxime, lead tetraacetate and Aspirin using conditions of General Method 3. $^1$H NMR (500 MHz, CHLOROFORM-d) δ 8.15 (1H, dd, 7.8, 1.5 Hz), 7.65 (1H, td, 7.8, 1.5 Hz), 7.40 (1H, t, 7.6 Hz), 7.17 (1H, d, 8.1 Hz), 4.08 (2H, dt, 11.6, 4.1 Hz), 3.79 (2H, td, 11.5, 2.4 Hz), 2.21-2.29 (5H, m), 1.96-1.99 (2H, m).

Example 46

Preparation of 4-[(4-nitrosotetrahydro-2H-pyran-4-yl)oxy]-4-oxobutyl 2-(acetyloxy)benzoate Benzyl 4-{[2-(acetyloxy)phenyl]carbonyloxy}butanoate was synthesized from benzyl-4-bromo)butanoate, 2-(acety-loxy)benzoic acid and potassium carbonate. To a solution of benzyl-4-bromobutanoate (0.5 g, 1.9 mmol) in acetonitrile (5 ml) at ambient temperature was added potassium carbonate (0.28 g, 2.0 mmol) and 2-(acetyloxy)benzoic acid (0.35 g, 1.9 mmol). The reaction was heated to 90° C. for 18 hours and monitored by TLC (4:1 heptane:EtOAc) The mixture was allowed to cool to room temperature and concentrated in vacuo. The crude product was partitioned between water and EtOAc and the organic phase was separated, dried over $Na_2SO_4$, filtered and concentrated in vacuo. The title compound was purified by silica column chromatography eluting with heptane:EtOAc (4:1, v:v) and isolated as a clear, colorless oil (0.556 g, 81% yield). $^1$H NMR (250 MHz, DMSO-$d_6$) δ 7.29-7.41 (5H, m), 5.09 (2H, s), 4.01 (2H, t, 6.5 Hz), 2.44 (2H, t, 7.3 Hz), 1.97 (3H, s), 1.85 (2H, quin, 6.9 Hz).

4-{[2-(Acetyloxy)phenyl]carbonyloxy}butanoic acid was synthesized from benzyl 4-{[2-(acetyloxy)phenyl] carbonyloxy}butanoate. To a solution of benzyl 4-{[2-(acetyloxy)phenyl]carbonyloxy}butanoate (1.13 g, 3.1 mmol) in EtOH (10 ml) at ambient temperature was added palladium on charcoal (50 mg, 10% w:w) under an atmosphere of $H_2$. After 3 hours at atmospheric temperature/pressure complete saponification of the benzyl ester was observed. The mixture was filtered, and the filtrate was concentrated in vacuo to provide the title compound. (0.83 g, 98% yield). $^1$H NMR (500 MHz, DMSO-$d_6$) δ ppm 7.95 (1H, dd, 7.9, 1.6 Hz), 7.68 (1H, td, 7.7, 1.6 Hz), 7.41 (1H, t, 7.6 Hz), 7.24 (1H, d, 8.1 Hz), 4.23 (2H, t, 6.5 Hz), 2.35 (2H, t, 7.2 Hz), 2.27 (3H, s), 1.90 (2H, quin, 6.9 Hz).

4-[(4-Nitrosotetrahydro-2H-pyran-4-yl)oxy]-4-oxobutyl 2-(acetyloxy)benzoate was prepared from tetrahydropyran-4-one oxime and bis (4-{[2-(acetyloxy)phenyl] carbonyloxy}butanoate) iodobenzene (synthesized from 4-{[2-(acetyloxy)phenyl]carbonyloxy}butanoic acid and iodobenzene diacetate) and using conditions of General Method 4. H NMR (250 MHz, MeOD) δ ppm 8.00 (1H, dt, 7.9, 2.0 Hz), 7.53-7.70 (1H, m), 7.30-7.46 (1H, m), 7.15 (1H, dd, 8.1, 1.2 Hz), 4.32-4.46 (2H, m), 3.88-3.97 (2H, m), 3.54-3.76 (2H, m), 2.63-2.77 (2H, m), 2.25-2.36 (4H, m), 1.97-2.21 (4H, m), 1.69-1.88 (1H, m).

Example 47

Preparation of 4-nitrosotetrahydro-2H-pyran-4-yl 4-({2-[4-(2-methylpropyl)phenyl]propanoyl}oxy) butanoate Benzyl 4-({2-[4-(2-methylpropyl)phenyl]propanoyl}oxy) butanoate was synthesized from benzyl-4-bromo)butanoate, 2-[4-(2-methylpropyl)phenyl]propanoic acid and potassium carbonate. To a solution of benzyl-4-bromobutanoate (2.0 g, 7.8 mmol) in acetonitrile (20 ml) at ambient temperature was added potassium carbonate (1.13 g, 8.2 mmol) and 2-[4-(2-methylpropyl)phenyl]propanoic acid (1.6 g, 7.8 mmol). The reaction was heated to 90° C. for 18 hours and monitored by TLC (4:1 heptane:EtOAc) The mixture was allowed to cool to room temperature and concentrated in vacuo. The crude product was partitioned between water and EtOAc and the organic phase was separated, dried over $Na_2SO_4$, filtered and concentrated in vacuo. The title compound was purified by silica column chromatography eluting with heptane: EtOAc (4:1, v:v) and isolated as a clear, colorless oil (2.5 g, 84% yield). $^1$H NMR (250 MHz, CHLOROFORM-d) δ ppm 7.30-7.46 (5H, m), 7.02-7.23 (4H, m), 5.11 (2H, s), 3.99-

4.21 (2H, m), 3.68 (1H, q, 7.2 Hz), 2.43 (2H, d, 7.2 Hz), 2.27-2.39 (2H, m), 1.73-2.04 (3H, m), 1.48 (3H, d, 7.2 Hz) 0.89 (6H, d, 6.6 Hz).

4-({2-[4-(2-Methylpropyl)phenyl]propanoyl}oxy)butanoic acid was synthesized from benzyl 4-({2-[4-(2-methylpropyl)phenyl]propanoyl}oxy)butanoate. To a solution of benzyl 4-({2-[4-(2-methylpropyl)phenyl]propanoyl}oxy)butanoate (2.5 g, 6.5 mmol) in EtOH (25 ml) at ambient temperature was added palladium on charcoal (80 mg, 10% w:w) under an atmosphere of $H_2$. After 3 hours at atmospheric temperature/pressure complete saponification of the benzyl ester was observed. The mixture was filtered, and the filtrate was concentrated in vacuo to provide the title compound. (1.89 g, 99% yield). $^1$H NMR (250 MHz, CHLOROFORM-d) δ 7.02-7.24 (4H, m), 4.12 (2H, t, 6.2 Hz), 3.62-3.76 (1H, m), 2.45 (2H, d, 7.2 Hz), 2.26-2.37 (2H, m), 1.77-1.99 (3H, m), 1.49 (3H, d, 7.2 Hz) 0.90 (6H, d, 6.9 Hz).

4-Nitrosotetrahydro-2H-pyran-4-yl 4-({2-[4-(2-methylpropyl)phenyl]propanoyl}oxy)butanoate was prepared from tetrahydropyran-4-one oxime and bis 4-({2-[4-(2methylpropyl)phenyl]propanoyl}oxy)butanoate) iodobenzene (synthesized from 4-({2-[4-(2-methylpropyl)phenyl]propanoyl}oxy)butanoic acid and iodobenzene diacetate) and using conditions of General Method 4. $^1$H NMR (250 MHz, CHLOROFORM-d) δ 7.16-7.25 (2H, m), 7.03-7.14 (2H, m), 4.15 (2H, dt, 12.3, 6.2 Hz), 3.98-4.09 (2H, m), 3.59-3.79 (3H, m), 2.40-2.53 (4H, m), 2.27-2.37 (1H, m), 2.11-2.28 (1H, m), 1.74-2.07 (5H, m), 1.50 (3H, dd, 7.2, 4.3 Hz), 0.90 (6H, d, 6.2 Hz).

Example 48

Preparation of 4-Nitrosooxan-4-yl (2R)-2-{[(tert-butoxy)carbonyl]amino}propanoate 4-Nitrosooxan-4-yl (2R)-2-{[(tert-butoxy)carbonyl]amino}propanoate was prepared from tetrahydropyran-4-one oxime and bis (2R)-2-{[(tert-butoxy)carbonyl]amino}propanoate) iodobenzene (synthesized from (2R)-2-{[tert-butoxy)carbonyl]amino}propanoic acid) and iodobenzene diacetate) and using conditions of General Method 4. $^1$H NMR (250 MHz, DMSO-d$_6$) δ 7.51 (1H, d, 7.0 Hz), 4.18 (1H, q, 7.2 Hz), 3.85-3.98 (2H, m), 3.59 (2H, m), 1.98-2.20 (2H, m), 1.58-1.81 (2H, m), 1.32-1.47 (12H, m).

Example 49

Preparation of 4-nitrosooxan-4-yl 2-{[1,3-bis(acetyloxy)propan-2-yl](methyl)amino}acetate 3-(Acetyloxy)-2-oxopropyl acetate was prepared according to the method detailed in *J. Am. Chem. Soc.*, 118, 1996, 6388-6395)

Tert-butyl 2-{[1,3-bis(acetyloxy)propan-2-yl](methyl)amino}acetate. To a solution of 3-(acetyloxy)-2-oxopropyl acetate (4.54 g, 26 mmol) in dichloroethane (75 ml) was added tert-butyl 2-(methylamino)acetate HCl. After stirring for 10 minutes sodium triacetoxyborohydride (8.3 g, 39 mmol) was added and stirring was continued for 18 hours and monitored by TLC (1:1 heptane:EtOAc). The reaction was quenched by the addition of saturated sodium hydrogen carbonate solution and the crude product was extracted into dichloromethane. The organic phase was separated, dried over MgSO$_4$, filtered and concentrated in vacuo. The title compound was purified by silica column chromatography eluting with 0-20% EtOAc:Hept to yield the title compound (1.32 g, 17% yield). $^1$H NMR (250 MHz, CHLOROFORM-d) δ 4.07-4.33 (4H, m), 3.34 (2H, s), 3.23 (1H, t, 5.9 Hz), 2.49 (3H, s), 1.99-2.19 (6H, m), 1.33-1.55 (9H, m).

2-{[1,3-bis(acetyloxy)propan-2-yl](methyl)amino}acetic acid. Tert-butyl 2-{[1,3-bis(acetyloxy)propan-2-yl](methyl)amino}acetate (1.32 g, 4.3 mmol) was stirred in a solution of 20% TFA:dichloromethane (20 ml) for 5 hours. Upon completion of reaction (assessed by LC-MS) the reaction was concentrated in vacuo and re-dissolved in dichloromethane (10 ml). The HCl salt was treated with polymer supported-diisopropylamine (3.5 g) for 18 hours and the resin removed by filtration. The resin was washed with MeCN (3×10 ml) and the title compound isolated by concentration in vacuo. (1.0 g, 93%)$^1$H NMR (500 MHz, CHLOROFORM-d) δ 4.18 (4H, d, 6.4 Hz), 3.41 (2H, s), 3.17-3.29 (1H, m), 2.50 (3H, s), 2.11 (6H, s).

4-Nitrosooxan-4-yl-2-{[1,3-bis(acetyloxy)propan-2-yl](methyl)amino}acetate could be synthesized from tetrahydropyran-4-one oxime and bis(2-{[1,3-bis(acetyloxy)propan-2-yl](methyl)amino}acetic acid) iodobenzene (synthesized from iodobenzene diacetate and 2-{[1,3-bis(acetyloxy)propan-2-yl](methyl)amino}acetic acid) and using conditions of General Method 4.

Example 50

Preparation of 4-nitrosooxan-4-yl 2-{N-[1,3-bis(acetyloxy)propan-2-yl]acetamido}acetate 3-(Acetyloxy)-2-oxopropyl acetate was prepared according to the method detailed in *J. Am. Chem. Soc.*, 118, 1996, 6388-6395)

Tert-butyl 2-{[1,3-bis(acetyloxy)propan-2-yl]amino}acetate. To a solution of 3-(acetyloxy)-2-oxopropyl acetate (3.0 g, 17.24 mmol) on dichloroethane (70 ml) was added tert-butyl 2-aminoacetate (2.35 ml, 17.24 mmol). The reaction was stirred for 90 minutes before sodium triacetoxyborohydride (5.5 g, 25.86 mmol) was added and stirring was continued for 18 hours. The reaction was quenched by the addition of saturated sodium hydrogen carbonate solution and the crude product was extracted into dichloromethane. The organic phase was separated, dried over MgSO$_4$, filtered and concentrated in vacuo. The title compound was purified by silica column chromatography eluting with 0-40% EtOAc:Hept to yield the title compound (1.93 g, 38% yield). $^1$H NMR (250 MHz, CHLOROFORM-d) δ 3.96-4.26 (4H, m), 3.30-3.45 (2H, m), 3.06 (1H, quin, 5.4 Hz), 2.09 (6H, s), 1.47 (9H, s).

Tert-butyl 2-{N-[1,3-bis(acetyloxy)propan-2-yl]acetamido}acetate. Acetyl chloride (0.357 ml, 5.0 mmol) was added dropwise to a stirred solution of tert-butyl 2-{[1,3-bis(acetyloxy)propan-2-yl]amino}acetate (1.22 g, 4.2 mmol) and triethylamine (0.696 ml, 5.0 mmol). After 2 hours the reaction was quenched by the addition of water. The organic phase was separated and washed with further aliquots of water before being dried over MgSO$_4$, filtered and concentrated in vacuo. The title compound was purified by silica column chromatography eluting with 25% EtOAc:Hept to yield the title compound (0.7 g, 50%). $^1$H NMR (250 MHz, CHLOROFORM-d) δ 4.04-4.44 (5H, m), 3.98 (1H, s), 3.88 (1H, s), 2.08 (3H, s), 2.05 (6H, s), 1.47 (9H, s).

2-{N-[1,3-bis(acetyloxy)propan-2-yl]acetamido}acetic acid. Tert-butyl 2-{N-[1,3-bis(acetyloxy)propan-2-yl]acetamido}acetate (1.32 g, 3.9 mmol) was stirred in a solution of 20% TFA:dichloromethane (20 ml) for 4 hours. Upon completion of reaction (assessed by LC-MS) the reaction was concentrated in vacuo and azeotroped with dichloroethane to remove any residual TFA. (0.95 g, 87%). $^1$H NMR (500 MHz, CHLOROFORM-d) δ 4.27-4.41 (2H, m), 4.12-4.26 (3H, m), 4.07 (1H, s), 3.74 (1H, s), 2.28 (3H, s) 2.10 (3H, s) 2.07 (3H, s).

4-nitrosooxan-4-yl 2-{N-[1,3-bis(acetyloxy)propan-2-yl]acetamido}acetate was synthesized from tetrahydropyran- 4-one oxime and bis(2-{N-[1,3-bis(acetyloxy)propan-2-yl]acetamido}acetic acid) iodobenzene and using conditions of General Method 4. $^1$H NMR (500 MHz, CHLOROFORM-d) δ 4.29-4.47 (2H, m), 4.10-4.25 (5H, m), 3.65-3.83 (2H, m), 2.47-2.58 (1H, m), 2.34-2.45 (1H, m), 2.21-2.31 (2H, m), 2.20 (3H, s), 2.13 (6H, s), 2.04-2.09 (2H, m).

Example 51

Preparation of Compounds 54, 55, 56, 57, 58, 43, 42 and 45

Title compounds may be prepared according to General Method 4. The title compounds may also be prepared according to literature methods.

Example 52

HNO Production Via $N_2O$ Quantification

HNO production of the compounds may be determined by UV-Vis spectroscopy.

Nitrous oxide is produced via the dimerization and dehydration of HNO, and is the most common marker for HNO production (Fukuto, J. M.; Bartberger, M. D.; Dutton, A. S.; Paolocci, N.; Wink, D. A.; Houk, K. N. Chem. Res. Toxicol. 2005, 18, 790-801). HNO, however, can also be partially quenched by oxygen to yield a product that does not produce $N_2O$ (See, (a) Mincione, F.; Menabuoni, L.; Briganti, F.; Mincione, G.; Scozzafava, A.; Supuran, C. T. J. Enzyme Inhibition 1998, 13, 267-284 and (b) Scozzafava, A.; Supuran, C. T. J. Med. Chem. 2000, 43, 3677-3687.) Using Angeli's salt (AS) as a benchmark, the relative amounts of $N_2O$ released from compounds are examined via GC headspace analysis. The ability of compounds to donate nitroxyl at pH 7.4 in PBS buffer at 37° C. is assessed based on the levels of $N_2O$ released.

Example 52A

HNO Production Via $N_2O$ Quantification

Compounds were tested in the assay described in Example 52, with the following modification. Test compounds were assessed with and also without the addition of Pig Liver Esterase (PLE) at 37° C. for 90 minutes in PBS buffer at pH 7.4. Certain compounds of Table 1 (e.g., compounds 1, 5, 7, 10, 15, 16, 17, 18, 20, 21, 22, 23, 25, 26, 31, 33, 35, 36, 37, 38, 39, 44, 48, 49 and 50) were tested and showed detectable levels of HNO. Certain compounds of Table 1 exhibited enhanced HNO production in the presence of PLE. Compound stability was also determined by assessing the half-life of the compounds in PBS at 37° C. at pH 7.4 with and without the addition of PLE according to methods known in the art, e.g., in PCT publication No. PCT/US2007/006710.

Example 53

Use of an In Vitro Model to Determine the Ability of Compounds of the Invention to Treat, Prevent and/or Delay the Onset and/or the Development of a Disease or Condition Responsive to Nitroxyl Therapy a. Cardiovascular Diseases or Conditions.

In vitro models of cardiovascular disease can also be used to determine the ability of any of the compounds described herein to treat, prevent and/or delay the onset and/or the development of a cardiovascular disease or condition in an individual. An exemplary in vitro model of heart disease is described below.

In-vitro models could be utilized to assess vasorelaxation properties of the compounds. Isometric tension in isolated rat thoracic aortic ring segment can be measured as described previously by Crawford, J. H., Huang, J, Isbell, T. S., Shiva, S., Chacko, B. K., Schechter, A., Darley-Usmar, V. M., Kerby, J. D., Lang, J. D., Krauss, D., Ho, C., Gladwin, M. T., Patel, R. P., Blood 2006, 107, 566-575. Upon sacrifice aortic ring segments are excised and cleansed of fat and adhering tissue. Vessels are then cut into individual ring segments (2-3 mm in width) and suspended from a force-displacement transducer in a tissue bath. Ring segments are bathed at 37° C. in a bicarbonate-buffered, Krebs-Henseleit (K-H) solution of the following composition (mM): NaCl 118; KCl 4.6; $NaHCO_3$ 27.2; $KH_2PO_4$ 1.2; $MgSO_4$ 1.2; $CaCl_2$ 1.75; $Na_2EDTA$ 0.03; and glucose 11.1 and perfused continuously with 21% $O_2$/5% $CO_2$/74% $N_2$. A passive load of 2 g is applied to all ring segments and maintained at this level throughout the experiments. At the beginning of each experiment, indomethacin-treated ring segments are depolarized with KCl (70 mM) to determine the maximal contractile capacity of the vessel. Rings are then washed extensively and allowed to equilibrate. For subsequent experiments, vessels are submaximally contracted (50% of KCl response) with phenylephrine (PE, $3\times10^{-8}$-$10^{-7}$ M), and L-NMMA, 0.1 mM, is also added to inhibit eNOS and endogenous NO production. After tension development reaches a plateau, nitroxyl donating compounds are added cumulatively to the vessel bath and effects on tension monitored.

In vitro models can be utilized to determine the effects of nitroxyl donating compounds in changes in developed force and intracellular calcium in heart muscles. Developed force and intracellular calcium can be measured in rat trabeculae from normal or diseased (i.e. rats with congestive heart failure or hypertrophy) as described previously (Gao W D, Atar D, Backx P H, Marbán E. Circ Res. 1995; 76:1036-1048). Rats (Sprague-Dawley, 250-300 g) are used in these experiments. The rats are anesthetized with pentobarbital (100 mg/kg) via intra-abdominal injection, the heart exposed by mid-sternotomy, rapidly excised and placed in a dissection dish. The aorta is cannulated and the heart perfused retrograde (~15 mM/min) with dissecting Krebs-Henseleit (H-K) solution equilibrated with 95% $O_2$ and 5% $CO_2$. The dissecting K-H solution is composed of (mM): NaCl 120, $NaHCO_3$ 20, KCl 5, $MgCl_2$ 1.2, glucose 10, $CaCl_2$ 0.5, and 2,3-butanedione monoximine (BDM) 20, pH 7.35-7.45 at room temperature (21-22° C.). Trabeculae from the right ventricle of the heart are dissected and mounted between a force transducer and a motor arm and superfused with normal K-H solution (KCl, 5 mM) at a rate of ~10 ml/min and stimulated at 0.5 Hz. Dimensions of the muscles are measured with a calibration reticule in the ocular of the dissection microscope (×40, resolution ~10 μm).

Force is measured using a force transducer system and is expressed in millinewtons per square millimeter of cross-sectional area. Sarcomere length is measured by laser diffraction. Resting sarcomere length is set at 2.20-2.30 μm throughout the experiments.

Intracellular calcium is measured using the free acid form of fura-2 as described in previous studies (Gao et al., 1994; Backx et al., 1995; Gao et al., 1998). Fura-2 potassium salt is microinjected iontophoretically into one cell and allowed to spread throughout the whole muscle (via gap junctions). The tip of the electrode (~0.2 μm in diameter) is filled with fura-2 salt (1 mM) and the remainder of the electrode was filled with 150 mM KCl. After a successful impalement into a superficial cell in non-stimulated muscle, a hyperpolarizing current of 5-10 nA is passed continuously for ~15 min. Fura-2 epifluorescence is measured by exciting at 380 and 340 nm. Fluorescent light is collected at 510 nm by a photomultiplier tube. The output of photomultiplier is collected and digitized. Ryanodine (1.0 µM) is used to enable steady-state activation. After 15 min of exposure to ryanodine, different levels of tetanizations are induced briefly (~4-8 seconds) by stimulating the muscles at 10 Hz at varied extracellular calcium (0.5-20 mM). All experiments are performed at room temperature (20-22° C.).

b. Diseases or Conditions Implicating Ischemia/Reperfusion.

In vitro models can also be used to determine the ability of any of the compounds described herein to treat, prevent and/or delay the onset and/or the development of a disease or condition implicating ischemia/reperfusion injury in an individual.

c. Cancer

Antitumor activities of the compounds described herein can be assessed using in vitro proliferation assays of tumor cells using well-known methods, such as described in Norris A. J. et al. *Intl. J Cancer* 2008, 122:1905-1910.

Cells of an appropriate cell line, e.g. human breast cancer cell line MCF-7, are seeded in 96-well tissue culture microtiter plates at ~4000 cells per well for an overnight incubation. Serial 10-fold dilutions of test compounds are added, and the cells are incubated for 72 h. The cell viability is determined using the CellTiter-Glo™ Luminescent Cell Viability Assay (Promega; Madison, Wis.). The $IC_{50}$ is measured as the concentration of drug required for inhibiting cell growth by 50%.

Example 54

Use of In Vivo and/or Ex Vivo Models to Determine the Ability of Compounds of the Invention to Treat, Prevent and/or Delay the Onset and/or the Development of a Disease or Condition Responsive to Nitroxyl Therapy a. Cardiovascular Diseases or Conditions.

In vivo models of cardiovascular disease can also be used to determine the ability of any of the compounds described herein to treat, prevent and/or delay the onset and/or the development of a cardiovascular disease or condition in an individual. An exemplary animal model of heart disease is described below.

In vivo cardiovascular effects obtained with a nitroxyl donor compound may be assessed in a control (normal) dog. The study is conducted in adult (25 kg) mongrel (male) dogs chronically instrumented for conscious hemodynamic analysis and blood sampling, as previously described (Katori, T.; Hoover, D. B.; Ardell, J. L.; Helm, R. H.; Belardi, D. F.; Tocchetti, C. G.; Forfia, P. R.; Kass, D. A.; Paolocci, N. *Circ. Res.* 2005; 96: 234-243.). Micromanometer transducers in the left ventricle provide pressure, while right atrial and descending aortic catheters provide fluid-pressures and sampling conduits. Endocardial sonomicrometers (anteriorposterior, septal-lateral) measure short-axis dimensions, a pneumatic occluder around the inferior vena cave facilitated pre-load manipulations for pressure-relation analysis. Epicardial pacing leads are placed on the right atrium, and another pair is placed on the right ventricle free wall linked to a permanent pacemaker to induce rapid pacing-cardiac failure. After 10 days of recovery, animals are evaluated at baseline sinus rhythm and with atrial pacing (120-160 bpm). Measurements include conscious hemodynamic recordings for cardiac mechanics.

Compounds of the invention are administrated to a healthy control dog at the dose of 1-5 µg/kg/min and the resulting cardiovascular data is obtained.

Demonstration that a compound of the invention improves cardiac hemodynamics in hearts with congestive failure: After completing protocols under baseline conditions, congestive heart failure is induced by tachypacing (210 bpm×3 weeks, 240 bpm×1 week), as previously described (Katori, T.; et al. *Circ. Res.* 2005; 96: 234-243.). Briefly, end-diastolic pressure and $dP/dt_{max}$ are measured weekly to monitor failure progression. When animals demonstrate a rise in EDP more than 2×, and $dP/dt_{max}$ of >50% baseline, they are deemed ready for congestive heart failure studies.

The values for test compounds are obtained after 15 min continuous i.v. infusion (2.5 or 1.25 µg/kg/min) in control and heart failure preparations, respectively, both in the absence and in the presence of volume restoration. For comparison, the same hemodynamic measurements are obtained with AS in heart failure preparations.

b. Diseases or Conditions Implicating Ischemia/Reperfusion

Ex-vivo models of ischemia/reperfusion can also be used to determine the ability of any of the compounds described herein to treat, prevent and/or delay the onset and/or the development of a disease or condition implicating ischemia/reperfusion injury in an individual. An exemplary ex vivo model of ischemia/reperfusion injury is described below.

Male Wistar rats are housed in identical cages and allowed access to tap water and a standard rodent diet ad libitum. Each animal is anesthetized with 1 g/kg urethane i.p. 10 min after heparin (2,500 U, i.m.) treatment. The chest is opened, and the heart is rapidly excised, placed in ice-cold buffer solution and weighed. Isolated rat hearts are attached to a perfusion apparatus and retrogradely perfused with oxygenated buffer solution at 37° C. The hearts are instrumented as previously described in Rastaldo et al., "P-450 metabolite of arachidonic acid mediates bradykinin-induced negative inotropic effect," *Am. J. Physiol.*, 280:H2823-H2832 (2001), and Paolocci et al. "cGMP-independent inotropic effects of nitric oxide and peroxynitrite donors: potential role for nitrosylation," *Am. J. Physiol.*, 279: H1982-H1988 (2000). The flow is maintained constant (approximately 9 mL/min/g wet weight) to reach a typical coronary perfusion pressure of 85-90 mm Hg. A constant proportion of 10% of the flow rate is applied by means of one of two perfusion pumps (Terumo, Tokyo, Japan) using a 50 mL syringe connected to the aortic cannula. Drug applications are performed by switching from the syringe containing buffer alone to the syringe of the other pump containing the drug (nitroxyl donating compound) dissolved in a vehicle at a concentration 10× to the desired final concentration in the heart. A small hole in the left ventricular wall allows drainage of the thebesian flow, and a polyvinylchloride balloon is placed into the left ventricle and connected to an electromanometer for recording of left ventricular pressure (LVP). The hearts are electrically paced at 280-300 bpm and kept in a temperature-controlled chamber (37° C.). Coronary perfusion pressure (CPP) and coronary flow are monitored with a second electromanometer and an electromagnetic flow-probe, respectively, both placed along the perfusion line. Left ventricular pressure, coronary flow and coronary perfusion pressure are recorded using a TEAC R-71 recorder, digitized at 1000 Hz and analyzed off-line with DataQ-Instruments/CODAS software, which allow quantification of the maximum rate of increase of LVP during systole ($dP/dt_{max}$).

Hearts are perfused with Krebs-Henseleit solution gassed with 95% $O_2$ and 5% $CO_2$ of the following composition: 17.7 mM sodium bicarbonate, 127 mM NaCl, 5.1 mM KCl, 1.5 mM $CaCl_2$, 1.26 mM $MgCl_2$, 11 mM D-glucose, supplemented with 5 μg/mL lidocaine.

Experimental Compounds. The nitroxyl donors are diluted in buffer immediately prior to use.

Experimental Protocols. Hearts are allowed to stabilize for 30 min, and baseline parameters are recorded. Typically, coronary flow is adjusted within the first 10 min and kept constant from thereon. After 30 min stabilization, hearts are randomly assigned to one of the treatment groups, and subjected to 30 min global, no-flow ischemia, followed by 30 min of reperfusion (I/R). Pacing of the hearts is stopped at the beginning of the ischemic period and restarted after the third minute of reperfusion.

Hearts in a control group are perfused with buffer for an additional 29 min after stabilization. Treated hearts are exposed to a nitroxyl donor (e. g., 1 μM final concentration for about 20 min followed by a 10 min buffer wash-out period).

In all hearts pacing is suspended at the onset of ischemia and restarted 3 minutes following reperfusion. As isolated heart preparations may deteriorate over time (typically after 2-2.5 hrs perfusion), the re-flow duration is limited to 30 min in order to minimize the effects produced by crystalloid perfusion on heart performance, and consistently with other reports.

Assessment of ventricular function. To obtain the maximal developed LVP, the volume of the intra-ventricular balloon is adjusted to an end-diastolic LVP of 10 mm Hg during the stabilization period, as reported in Paolocci, supra, and Hare et al., "Pertussis toxin-sensitive G proteins influence nitric oxide synthase III activity and protein levels in rat hearts," *J. Clin. Invest.*, 101:1424-31 (1998). Changes in developed LVP, $dP/dt_{max}$ and the end-diastolic value induced by the I/R protocol are continuously monitored. The difference between the end-diastolic LVP (EDLVP) before the end of the ischemic period and during pre-ischemic conditions is used as an index of the extent of contracture development. Maximal recovery of developed LVP and $dP/dt_{max}$ during reperfusion is compared with respective pre-ischemic values.

Assessment of myocardial injury. Enzyme release is a measure of severe myocardial injury that has yet to progress to irreversible cell injury. Samples of coronary effluent (2 mL) are withdrawn with a catheter inserted into the right ventricle via the pulmonary artery. Samples are taken immediately before ischemia and at 3, 6, 10, 20 and 30 min of reperfusion. LDH release is measured as previously described by Bergmeyer & Bernt, "Methods of Enzymatic Analysis," *Verlag Chemie* (1974). Data are expressed as cumulative values for the entire reflow period.

To corroborate the data relative to myocardial injury, determined by LDH release, infarct areas are also assessed in a blinded fashion. At the end of the course (30 min reperfusion), each heart is rapidly removed from the perfusion apparatus, and the LV dissected into 2-3 mm circumferential slices. Following 15 min of incubation at 37° C. in 0.1% solution of nitro blue tetrazolium in phosphate buffer as described in Ma et al., "Opposite effects of nitric oxide and nitroxyl on postischemic myocardial injury," *Proc. Natl. Acad. Sci.*, 96:14617-14622 (1999), unstained necrotic tissue is separated from the stained viable tissue. The areas of viable and necrotic tissue are carefully separate by and independent observer who is not aware of the origin of the hearts. The weight of the necrotic and non-necrotic tissues is then determined and the necrotic mass expressed as a percentage of total left ventricular mass.

Data may be subjected to statistical methods such as ANOVA followed by the Bonferroni correction for post hoc t tests.

c. Cancer

Anticancer activities of compounds described herein can be assessed using in vivo mouse xenograft models using methods described in Norris A. J. et al (*Intl. J. Cancer* 2008, 122, 1905-1910) and Stoyanovsky, D. A. et al (*J. Med. Chem.* 2004, 47, 210-217).

Mice are inoculated with appropriate tumor cells by subcutaneous injection into the lower flank. Therapy can be started after 1-3 weeks when the tumors have reached an average volume of ~50-60 $mm^3$. Tumor diameters are measured with digital calipers, and the tumor volume is calculated. The anti-tumor efficacy of test compounds is assessed by comparison of tumor size in test group to that in the control group.

Example 55

Use of Human Clinical Trials to Determine the Ability to Combination Therapies of the Invention to Treat, Prevent and/or Delay the Onset and/or the Development of a Disease or Condition Responsive to Nitroxyl Therapy If desired, any of the compounds described herein can also be tested in humans to determine the ability of the compound to treat, prevent and/or delay the onset and/or the development of a disease or condition responsive to nitroxyl therapy. Standard methods can be used for these clinical trials. In one exemplary method, subjects with such a disease or condition, such as congestive heart failure, are enrolled in a tolerability, pharmacokinetics and pharmacodynamics phase I study of a therapy using the compounds of the invention in standard protocols. Then a phase II, double-blind randomized controlled trial is performed to determine the efficacy of the compounds using standard protocols.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

All references, publications, patents, and patent applications disclosed herein are hereby incorporated by reference in their entireties.

What is claimed is:
1. A compound of the formula I:

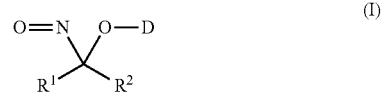

or a pharmaceutically acceptable salt thereof,
wherein:
each $R^1$ and $R^2$ is independently a moiety of the formula $C_1$-$C_4$alkyl-O—$C_1$-$C_4$alkyl- or acyl-O—$C_1$-$C_4$alkyl;

D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, and heterocyclyl-C(O)—.

2. A compound of claim 1 or a pharmaceutically acceptable salt thereof, wherein D is selected from the group consisting of alkyl-C(O)—, substituted alkyl-C(O)—, perhaloalkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, and heterocyclyl-C(O)—.

3. A compound of claim 1 or a pharmaceutically acceptable salt thereof, wherein $R^1$ and $R^2$ are each of the formula $CH_3CH_2$—O—$CH_2$— or $CH_3C(O)$—O—$CH_2$—.

4. A compound of claim 1 or a pharmaceutically acceptable salt thereof, wherein D is $C_1$-$C_8$ alkyl-C(O)—.

5. A compound of claim 4 or a pharmaceutically acceptable salt thereof, wherein D is $CH_3$—C(O)—.

6. A pharmaceutical composition comprising (i) a compound according to claim 1 or a pharmaceutically acceptable salt thereof, and (ii) a pharmaceutically acceptable carrier.

7. The pharmaceutical composition of claim 6 wherein the composition is amenable to parenteral administration.

8. A method of treating a condition selected from the group consisting of coronary obstructions, coronary artery disease (CAD), angina, heart attack, myocardial infarction, high blood pressure, ischemic cardiomyopathy and infarction, diastolic heart failure, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, congestive heart failure, acute congestive heart failure, acute decompensated heart failure, pulmonary hypertension and cardiac hypertrophy comprising administering to an individual in need thereof a therapeutically effective amount of a compound according to claim 1 or a pharmaceutically acceptable salt thereof.

9. The method of claim 8 wherein the condition is heart failure.

10. A compound or a pharmaceutically acceptable salt thereof, wherein the compound is

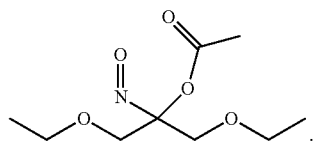

11. A compound or a pharmaceutically acceptable salt thereof, wherein the compound is

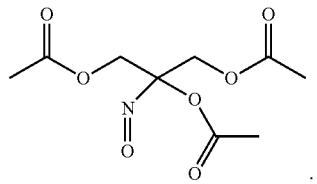 [SMILES: CC(=O)OCC(COC(C)=O)(N=O)OC(C)=O]

* * * * *